(12) United States Patent
Blackwell et al.

(10) Patent No.: US 10,526,278 B2
(45) Date of Patent: Jan. 7, 2020

(54) INHIBITORS OF QUORUM SENSING RECEPTOR LASR

(71) Applicant: Wisconsin Alumni Research Foundation, Madison, WI (US)

(72) Inventors: Helen Blackwell, Middleton, WI (US); Daniel Manson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/157,855

(22) Filed: Oct. 11, 2018

(65) Prior Publication Data

US 2019/0119201 A1 Apr. 25, 2019

Related U.S. Application Data

(60) Provisional application No. 62/574,348, filed on Oct. 19, 2017, provisional application No. 62/650,329, filed on Mar. 30, 2018.

(51) Int. Cl.
 C07C 235/74 (2006.01)
 A61P 31/04 (2006.01)
 C07D 307/33 (2006.01)
(52) U.S. Cl.
 CPC ............ *C07C 235/74* (2013.01); *A61P 31/04* (2018.01); *C07D 307/33* (2013.01)
(58) Field of Classification Search
 CPC .............................. C07C 235/74; A61P 31/04
 See application file for complete search history.

(56) References Cited

U.S. PATENT DOCUMENTS

| | | | |
|---|---|---|---|
| 4,072,703 A | 2/1978 | Blum | |
| 5,278,326 A | 1/1994 | Angelli-Szafran et al. | |
| 5,410,049 A | 4/1995 | Chambers | |
| 5,593,827 A | 1/1997 | Bycroft et al. | |
| 5,776,974 A | 7/1998 | Bycroft et al. | |
| 6,555,356 B2 | 4/2003 | Kjelleberg et al. | |
| 6,559,176 B1 | 5/2003 | Bassler et al. | |
| 6,756,404 B2 | 6/2004 | Livinghouse | |
| 6,780,890 B2 | 8/2004 | Bassler et al. | |
| 6,855,513 B1 | 2/2005 | Whitely et al. | |
| 6,958,145 B2 | 10/2005 | Kumar et al. | |
| 7,026,353 B2 | 4/2006 | Kjelleberg et al. | |
| 7,074,776 B2 | 7/2006 | Cooper et al. | |
| 7,078,435 B2 | 7/2006 | Livinghouse | |
| 7,094,394 B2 | 8/2006 | Davies et al. | |
| 7,332,509 B2 | 2/2008 | Shaper et al. | |
| 7,335,779 B2 | 2/2008 | Ammendola | |
| 7,338,969 B2 | 3/2008 | Ammendola | |
| 7,498,292 B2 | 3/2009 | Suga et al. | |
| 7,642,285 B2 | 1/2010 | Blackwell et al. | |
| 7,659,409 B2 | 2/2010 | Takehara et al. | |
| 7,737,164 B2 | 6/2010 | Blackwell et al. | |
| 7,883,720 B2 | 2/2011 | Lynn et al. | |
| 7,910,622 B2 | 3/2011 | Blackwell et al. | |
| 8,071,210 B2 | 12/2011 | Lynn et al. | |
| 8,227,616 B2 | 7/2012 | Blackwell et al. | |
| 8,247,443 B2 | 8/2012 | Bassler et al. | |
| 8,269,024 B2 | 9/2012 | Blackwell et al. | |
| 8,350,061 B2 | 1/2013 | Iyer et al. | |
| 8,367,680 B2 | 2/2013 | Blackwell et al. | |
| 8,618,327 B2 | 12/2013 | Blackwell et al. | |
| 8,624,063 B2 | 1/2014 | Blackwell et al. | |
| 8,815,943 B2 | 8/2014 | Blackwell et al. | |
| 8,877,940 B2 | 11/2014 | Rahme et al. | |
| 9,758,472 B2 | 9/2017 | Blackwell et al. | |

(Continued)

FOREIGN PATENT DOCUMENTS

| | | |
|---|---|---|
| DE | 2513842 | 9/1975 |
| EP | 1 431 280 | 6/2004 |

(Continued)

OTHER PUBLICATIONS

Amara N. et al. (2009) "Covalent Inhibition of Bacterial Quorum Sensing," J. Am. Chem. Soc. 131:10610-10619.
Bottomley et al. (May 2007) "Molecular Insights into Quorum Sensing in the Human Pathogen Pseudomonas aeruginosa from the Structure of the Virulence Regulator LasR Bound to Its Autoinducer," J. Biol. Chem. 282(18):13592-13600.
Castang et al. (Oct. 2004) "N-Sulfonyl Homoserine Lactone as Antagonists of Bacterial Quorum Sensing," *Bioorg. Med. Chem. Lett.* 14(20):5145-5149.
Chhabra, S.R. et al. (Nov. 2002) "Synthetic Analogues of the Bacterial Signal (Quorum Sensing) Molecule N-(3-Oxododecanoyl)-L-homoserine Lactone as Immune Modulators," J. Med. Chem. (2003) 46, 97-104.

(Continued)

*Primary Examiner* — Golam M Shameem
(74) *Attorney, Agent, or Firm* — Leydig, Voit & Mayer. Ltd.

(57) ABSTRACT

Modulation of quorum sensing in Gram-negative bacteria, particularly strains of *Pseudomonas* which form biofilms, by compounds including those of formula I and formula II:

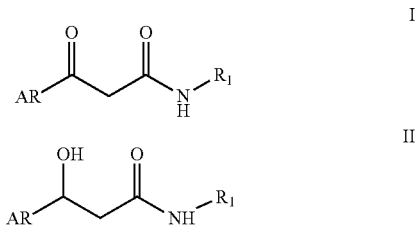

where:
AR is optionally substituted phenyl, cycloalkyl or cycloalkenyl or heterocyclic, and $R_1$ is optionally substituted alkyl, alkenyl, alkoxyalkyl, or alkylthioalkyl or alkyl substituted at the omega position with optionally substituted phenyl, cyclohexyl or cyclohexenyl. In particular compounds inhibit quorum sensing and biofilm formation. Pharmaceutical compositions for treatment of bacterial infections and methods of treatment of such infections are provided.

20 Claims, 19 Drawing Sheets

(56) References Cited

U.S. PATENT DOCUMENTS

| | | | |
|---|---|---|---|
| 9,796,694 B2 | 10/2017 | Blackwell et al. | |
| 10,322,112 B2 * | 6/2019 | Blackwell | A61K 31/4184 |
| 2002/0037578 A1 | 2/2002 | Kjellberg et al. | |
| 2002/0177715 A1 | 10/2002 | Pesci et al. | |
| 2003/0105143 A1 | 4/2003 | Ammendola et al. | |
| 2003/0125381 A1 | 5/2003 | England et al. | |
| 2003/0198692 A1 | 9/2003 | Holmstrom et al. | |
| 2003/0224032 A1 | 10/2003 | Read et al. | |
| 2004/0072898 A1 | 2/2004 | Kjellberg et al. | |
| 2004/0110966 A1 | 4/2004 | Kumar et al. | |
| 2004/0115732 A1 | 4/2004 | Suga et al. | |
| 2004/0147595 A1 | 6/2004 | Kjellberg et al. | |
| 2004/0180829 A1 | 7/2004 | Bassler et al. | |
| 2004/0180936 A1 | 9/2004 | Auvin et al. | |
| 2004/0235914 A1 | 10/2004 | Ammendola et al. | |
| 2005/0054722 A1 | 1/2005 | England et al. | |
| 2005/0215772 A1 | 8/2005 | Kumar | |
| 2006/0052425 A1 | 1/2006 | Handelsman et al. | |
| 2006/0178430 A1 | 6/2006 | Blackwell et al. | |
| 2006/0264641 A1 | 11/2006 | Berendes et al. | |
| 2007/0054883 A1 | 1/2007 | Cooper et al. | |
| 2007/0093534 A1 | 3/2007 | Ammendola et al. | |
| 2007/0128658 A1 | 4/2007 | Blackwell et al. | |
| 2007/0155698 A1 | 7/2007 | Steinberg et al. | |
| 2007/0184014 A1 | 8/2007 | Ammendola et al. | |
| 2007/0196340 A1 | 8/2007 | Ammendola et al. | |
| 2007/0197492 A1 | 8/2007 | Ammendola et al. | |
| 2007/0203128 A1 | 8/2007 | Ammendola et al. | |
| 2007/0208012 A1 | 9/2007 | Ammendola et al. | |
| 2007/0264715 A1 | 11/2007 | Robinson et al. | |
| 2008/0009528 A1 | 1/2008 | Blackwell et al. | |
| 2008/0027115 A1 | 1/2008 | Suga et al. | |
| 2008/0176938 A1 | 7/2008 | Ammendola et al. | |
| 2008/0182878 A1 | 7/2008 | Ammendola et al. | |
| 2008/0188491 A1 | 8/2008 | Ammendola et al. | |
| 2008/0188535 A1 | 8/2008 | Ammendola et al. | |
| 2008/0188536 A1 | 8/2008 | Ammendola et al. | |
| 2008/0194588 A1 | 8/2008 | Ammendola et al. | |
| 2008/0194607 A1 | 8/2008 | Ammendola et al. | |
| 2008/0214635 A1 | 9/2008 | Ammendola et al. | |
| 2008/0286345 A1 | 11/2008 | Lynn et al. | |
| 2008/0312319 A1 | 12/2008 | Blackwell et al. | |
| 2009/0105375 A1 | 4/2009 | Lynn et al. | |
| 2009/0123512 A1 | 5/2009 | Muh et al. | |
| 2009/0163545 A1 | 6/2009 | Goldfarb | |
| 2009/0192192 A1 | 7/2009 | Ammendola et al. | |
| 2009/0270423 A1 | 10/2009 | Blackwell et al. | |
| 2010/0056602 A1 | 3/2010 | Salman et al. | |
| 2010/0160423 A1 | 6/2010 | Bassler et al. | |
| 2010/0261763 A1 | 10/2010 | Blackwell et al. | |
| 2010/0305182 A1 | 12/2010 | Blackwell et al. | |
| 2011/0046195 A1 | 2/2011 | Blackwell et al. | |
| 2011/0212860 A1 | 9/2011 | Blackwell et al. | |
| 2014/0142156 A1 | 5/2014 | Blackwell et al. | |
| 2015/0080349 A1 | 3/2015 | Blackwell et al. | |
| 2017/0231962 A1 | 8/2017 | Blackwell et al. | |
| 2017/0334835 A1 | 11/2017 | Blackwell et al. | |
| 2017/0369462 A1 | 12/2017 | Blackwell et al. | |
| 2019/0144407 A1 | 5/2019 | Blackwell et al. | |

FOREIGN PATENT DOCUMENTS

| | | |
|---|---|---|
| EP | 2 078 713 | 7/2009 |
| EP | 2 100 602 | 9/2009 |
| JP | S49-020492 | 5/1974 |
| JP | H02-235850 | 9/1990 |
| JP | H03-031245 | 2/1991 |
| JP | H03-232849 | 10/1991 |
| JP | H04-279568 | 10/1992 |
| WO | 1992/018614 | 10/1992 |
| WO | 1996/029392 | 9/1996 |
| WO | 1998/015532 | 4/1998 |
| WO | 1999/027786 | 6/1999 |
| WO | 1999/053915 | 10/1999 |
| WO | 2001/043739 | 6/2001 |
| WO | 2001/068090 | 9/2001 |
| WO | 2001/068091 | 9/2001 |
| WO | 2001/076594 | 10/2001 |
| WO | 2001/085664 | 11/2001 |
| WO | 2002/000639 | 1/2002 |
| WO | 2002/018342 | 3/2002 |
| WO | 2002/047681 | 6/2002 |
| WO | 2002/052949 | 7/2002 |
| WO | 2002/102370 | 12/2002 |
| WO | 2003/039529 | 5/2003 |
| WO | 2003/039549 | 5/2003 |
| WO | 2003/106445 | 12/2003 |
| WO | 2004/016213 | 2/2004 |
| WO | 2004/016588 | 2/2004 |
| WO | 2004/106299 | 12/2004 |
| WO | 2006/079015 | 7/2006 |
| WO | 2006/084056 | 8/2006 |
| WO | 2006/125262 | 11/2006 |
| WO | 2008/016738 | 2/2008 |
| WO | 2008/116029 | 9/2008 |
| WO | 2009/050575 | 4/2009 |
| WO | 2009/077844 | 6/2009 |
| WO | 2010/010380 | 1/2010 |
| WO | 2015/042363 | 3/2015 |

OTHER PUBLICATIONS

Eibergen, N. R., Moore, J. D., Mattmann, M. E. & Blackwell, H. E. (2015) "Potent and selective modulation of the RhIR quorum sensing receptor by using non-native ligands: an emerging target for virulence control in Pseudomonas aeruginosa," ChemBioChem, 16, 2348-2356.

Frezza et al. (2006) "Synthesis and Biological Evaluation of Homoserine Lactone Derived Ureas as Antagonists of Bacterial Quorum Sensing," *Bioorg. Med. Chem*. 14:4781-4791.

Galloway, W. R. J. D., Hodgkinson, J. T., Bowden, S. D., Welch, M. & Spring, D. R. (2011) "Quorum sensing in Gram-negative bacteria: small-molecule modulation of AHL and AI-2 quorum sensing pathways," Chem. Rev., 111, 28-67.

Gerdt et al (2015) "Unraveling the contributions of hydrogen-bonding interactions to the activity of native and non-native ligands in the quorum-sensing receptor LasR," Org. Biomol. Chem. 13(5):1453-1462.

Geske et al. (2005) "Small Molecule Inhibitors of Bacterial Quorum Sensing and Biofilm Formation," J. Am. Chem. Soc. 127:12762-12763.

Geske et al. (2007) "N-Phenylacetanoyl-L-Homoserine Lactones Can Strongly Antagonize or Superagonize Quorum Sensing in Vibrio fischeri," Chem. Biol. 2(5):315-320.

Geske et al. (2007)"Modulation of Bacterial Quorum Sensing with Synthetic Ligands: Systematic Evaluation of N-Acylated Homoserine Lactones in Multiple Species and New Insights into Their Mechanisms of Action," J. Am. Chem. Soc. 129: 13613-13625.

Geske et al. (2008) "Evaluation of a Focused Library of N-aryl L-Homoserine Lactones Reveals a New Set of Potent Quorum Sensing Modulators," Bioorg. Med. Chem. Lett. 18:5978-5981.

Geske et al. (2008) "Expanding Dialogues: From Natural Autoinducers to Non-Natural Analogues that Modulate Quorum Sensing in Gram-Negative Bacteria," Chem. Soc. Rev. 37:1432-1447.

Geske et al. (2008) "Comparative Analyses of N-Acylated Homoserine Lactones Reveal Unique Structural Features that Dictate Their Ability to Activate or Inhibit Quorum Sensing," ChemBioChem 9:389-400.

Gonzalez et al. (2006) "Messing with Bacterial Quorum Sensing," *Microbiol. Mol. Biol. Rev*. 70(4):859-875.

Hodgkinson et al. (2012) "Design, Synthesis and Biological Evaluation of Non-Natural Modulators of Quorum Sensing Pseudomonas aeruginosa," Org. Biomol. Chem. 10:6032-6044.

Ishida, T.; Ikeda, T.; Takiguchi, N.; Kuroda, A.; Ohtake, H.; Kato, J. (2007) "Inhibition of Quorum Sensing in Pseudomonas aeruginosa by N-Acyl Cyclopentylamides," Appl. Environ. Microbiol. 73, 3183-3188.

Janssens et al. (Jan. 2007) "Synthesis of N-Acyl Homoserine Lactone Analogues Reveals Strong Activators of SdiA, the *Salmo*-

(56) References Cited

OTHER PUBLICATIONS nella enterica Serovar Typhimurium LuxR Homologue," *Appl. Environ. Microbiol.* 73(2):535-544.

Jog et al. (Feb. 2006) "Stereoisomers of *P. aeruginosa* Autoinducer Analog to probe the Regulator Binding Site," *Chem. Biol.* 13:123-128.

Manson, D. E. et al. PERLMAN Symposium Mar. 31, 2017, Ebling Symposium Center Microbial Sciences Building University of Wisconsin Madison, WI, 12 pages.

Manson, D. E. et al. (Oct. 16-19, 2017) 6th American Society for Microbiology (ASM) Conference on Cell-Cell Coi-Communication in Bacteria, American Society of Microbiology, Athens, GA, 29 pages.

Mattmann et al. (2008) "Synthetic Ligands that Activate and Inhibit a Quorum-Sensing Regulator in Pseudomonas aeruginosa," *Biorg. Med. Chem. Lett.* 18(10):3072-3075.

Mattmann et al. (2011) "Potent and Selective Synthetic Modulators of a Quorum Sensing Repressor in Pseudomonas aeruginosa Identified from Second-Generation Libraries of N-Acylated L-Homoserine Lactones," *ChemBioChem.* 12:942-949.

McInnis, C. E.; Blackwell, H. E. (2011) "Thiolactone modulators of quorum sensing revealed through library design and screening," *Biorgan. Med. Chem.* 19, 4820-4828.

McInnis, C. E.; Blackwell, H. E. (2011) "Design, synthesis, and biological evaluation of abiotic, non-lactone modulators of LuxR-type quorum sensing," *Biorgan. Med. Chem.* 19, 4812-4819.

Moore, J.D., Gerdt, J.P., Eibergen, N.R., Blackwell, H.E. (2014) "Active efflux influences the potency of quorum sensing inhibitors in Pseudomonas aeruginosa," *Chem Bio Chem* 15, 435-442.

Moore, J. D., Rossi, F. M., Welsh, M. A., Nyffeler, K. E. & Blackwell, H. E. (2015) "A comparative analysis of synthetic quorum sensing modulators in Pseudomonas aeruginosa: New insights into mechanism, active efflux susceptibility, phenotypic response, and next-generation ligand design," *J. Am. Chem. Soc.*, 137(46), 14626-14639.

Morkunas, B et al. (2012) "Inhibition of the production of the Pseudomonas aeruginosa virulence factor pyocyanin in wild-type cells by quorum sensing autoinducer-mimics," *Org. Biomol.*, 42, 8452-8464.

Muh, U., Schuster, M., Heim, R., Singh, A., Olson, E. R. & Greenberg, E. P. (2006) "Novel Pseudomonas aeruginosa quorum-sensing inhibitors identified in an ultra-high-throughput scree," *Antimicrob. Agents Chemother.*, 50, 3674-3679.

Muh et al. (2006) "A Structurally Unrelated Mimic of a Pseudomonas aeruginosa Acyl-Homoserine Lactone Quorum-Sensing Signal," *Proc. Nat. Acad. Sci. USA* 103(45):16948-16952.

Oinuma et al. (2011) "Acyl-Homoserine Lactone Binding to and Stability of the Orphan *Pseudomonas aeruginosa* Quorum-Sensing Signal Receptor QscR_," *J. Bact.* 193(2):421-428.

O'Brien, K.T.;Noto, J.G.; Nichols-O'Neill, L.; Perez, L.J. (2015) "Potent Irreversible Inhibitors of LasR Quorum Sensing in Pseudomonas aeruginosa," *ACS Medicinal Chemistry Letters*, 6, 162-167.

O'Loughlin, C. T., Miller, L. C., Siryaporn, A., Drescher, K., Semmelhack, M. F. & Bassler, B. L. (2013) "A quorum-sensing inhibitor blocks Pseudomonas aeruginosa virulence and biofilm formation," *Proc. Natl. Acad. Sci. U. S. A.*, 110, 17981-17986.

O'Reilly, M. C. and Blackwell, H. E. (2015) "Structure-Based Design and Biological Evaluation of Triphenyl Scaffold-Based Hybrid Compounds as Hydrolytically Stable Modulators of a LuxR-Type Quorum Sensing Receptor," *ACS Infect. Dis*, 2, 32-38.

Pearson et al. (1997) "Roles of *Pseudomonas aeruginosa* las and rhl Quorum-Sensing Systems in Control of Elastase and Rhamnolipid Biosynthesis Genes," *J. Bacteriol.* 179(18):5756-5767.

Pearson, J.P., et al. (1999) "Active Efflux and Diffusion Are Involved in Transport of Pseudomonas aeruginosa Cell-to-Cell Signals," *J. Bacteriology*, 181(4):1203-1210.

Persson, T.; Hansen, T. H.; Rasmussen, T. B.; Skinderso, M. E.; Givskov, M.; Nielsen, J. (2005) "Rational design and synthesis of new quorum-sensing inhibitors derived from acylated homoserine lactones and natural products from garlic," *Org. Biomol. Chem.* 3, 253-262.

Reverchon, S.; Chantegrel, B.; Deshayes, C.; Doutheau, A.; Cotte-Pattat, N. (2002) "New synthetic analogues of N-acyl homoserine lactones as agonists or antagonists of transcriptional regulators involved in bacterial quorum sensing," *Bioorg. Med. Chem. Lett.* 12, 1153-1157.

Rutherford, S. T. & Bassler, B. L. (2012) "Bacterial quorum sensing: its role in virulence and possibilities for its control," *Cold Spring Harb. Perspect. Med.*, 2, a012427.

Smith, K. M.; Bu, Y.; Suga, H. (2003) "Library screening for synthetic agonists and antagonists of a Pseudomonas aeruginosa autoinducer," *Chem. Biol.* 10, 563-571.

Smith, K. M.; Bu, Y.; Suga, H. (2003) "Induction and inhibition of Pseudomonas aeruginosa quorum sensing by synthetic autoinducer analogs," *Chem. Biol.* 10, 81-89.

Starkey, M., et al. (2014) "Identification of anti-virulence compounds that disrupt quorum sensing regulated acute and persistent pathogenicity," *PLoS Pathog.*, 10, e1004321.

Welsh et al. (2015) "Small Molecule Disruption of Quorum Sensing Cross-Regulation in Pseudomonas Aeruginosa Causes Major and Unexpected Alterations to Virulence Phenotypes," *J. Am. Chem. Soc.* 137:1510-1519.

Welsh et al. (Feb. 2016) "Chemical Genetics Reveals Environment-Specific Roles for Quorum Sensing Circuits in Pseudomonas aeruginosa," *Cell Chem Biol* 23(3):361-369.

Welsh et al. (Jun. 2016) "Chemical Probes of Quorum Sensing: From Compound Development to Biological Discovery," *FEMS Microbiol. Rev* 40(5):774-794.

Williams, P., et al. (2007) "Look who's talking: communication and quorum sensing in the bacterial world," *Philosophical Transactions Royal Society B*, 362:119-1134.

Zhu et al. (1998) "Analogs of the Autoinducer 3-Oxooctanoyl-Homoserine Lactone Strongly Inhibit Activity of the TraR Protein of *Agrobacterium tumerfaciens*," *J. Bacteriol.* 180(20):5398-5405.

Gupta et al. (Dec. 2018) "Catalytic Asymmetric Epoxidation of Aldehydes with Two VANOL-Derived Chiral Borate Catalysts," *Angewandte Chemie, Int'l Edition* (2019) 58(11):3361-3367, Amer. Chem. Soc. Abstract Only, with structures of compounds with ACS Reg. No.

Hishmat, et al. (1977) "Synthesis and biological activity of some coumarin and furocoumarin derivatives," *Pharmaceutica Acta Helvetiae*, 52(10): 252-255, Amer. Chem. Soc. Abstract Only, with structure of compound.

Ino et al. (2003) PCT Int. Appl. WO200302069 "Preparation of 4-(2-carbamoylethenyl)phenyl sulfamate derivatives as steroid sulphatase inhibitors for treatment of breast cancer, endometrial carcinoma, ovarian cancer, and prostatic cancer," Amer. Chem. Soc. Abstract Only (English) with structure of compound with ACS Reg. No.

Mironescu et al. (1935) "Reactions of β-ketonic esters of the furan ring," *Bul. Soc. Chim. Romania* 17:107-29, Amer. Chem. Soc. Abstract Only with structures of compounds with ACS Reg. No.

\* cited by examiner

INHIBITORS OF QUORUM SENSING RECEPTOR LASR

CROSS-REFERENCE TO RELATED APPLICATIONS

This application claims the benefit of U.S. provisional application 62/574,348, filed Oct. 19, 2017 and U.S. provisional application 62/650,329, filed Mar. 30, 2018, each of which is incorporated by reference herein in its entirety.

STATEMENT REGARDING FEDERALLY SPONSORED RESEARCH OR DEVELOPMENT

This invention was made with government support under GM109403 awarded by the National Institutes of Health. The government has certain rights in the invention.

BACKGROUND

Quorum sensing (QS) is a method of intercellular communication in certain microorganisms which assesses local population density and coordinates the expression of phenotypes beneficial to the microorganism population. QS involves the release of a chemical signal, typically a small molecule or peptide autoinducer, into the environment at a concentration proportional to cell density. At a threshold signal concentration, the autoinducer binds a cognate receptor protein initiating changes in gene expression.

For example, the Gram-negative, opportunistic pathogen *Pseudomonas aeruginosa* uses QS to regulate biofilm formation, group motility, and various excreted virulence factors to overwhelm host defenses and establish chronic infections. Often these infections occur in immunocompromised individuals, for example, those having cystic fibrosis or HIV or suffering from chronic wounds.

Multidrug resistance to antibiotics is an emerging global threat and is a particular concern with pathogenic *Pseudomonas* strains and more particularly with *Pseudomonas aeruginosa*. In response to this threat, there has been increasing clinical interest in the development of antivirulence therapeutics with the development of chemical agents that can attenuate bacterial virulence phenotypes without generating a strong selective pressure to evolve resistance. QS circuits are particularly attractive targets for development of such chemical agents and anti-QS agents hold significant promise as resistance-robust drugs.

The exemplary Gram-negative bacterial, opportunistic pathogen *Pseudomonas aeruginosa* uses three interacting QS circuits—Las, Rhl, and Pq, see FIG. 1—to regulate the global expression of myriad virulence-associated genes. See: Welsh M. et al. (2015) for an overview of QS in *P. aeruginosa*. Interception of these signaling networks with small molecules represents an emerging strategy for the development of anti-infective agents against this bacterium. N-acyl L-homoserine lactones (AHLs) act as autoinducers for QS in the LasR and the RhlR circuits (natural autoinducers are illustrated in FIG. 1). The AHL signal is synthesized by a LuxI-type synthase and is recognized by an intracellular LuxR-type receptor. LasI and RhlI produce the autoinducers N-(3-oxododecanoyl)-L-homoserine lactone (OdDHL) and N-butyryl-L-homoserine lactone (BHL), respectively. The native signals activate LasR and RhlR which homodimerize and act as transcription factors to regulate a specific set of genes. In turn, LasR and RhlR are repressed by the "orphan" LuxR-type receptor QscR, which also binds OdDHL. A third QS system in *P. aeruginosa*, Pqs, does not respond to AHLs, but to the autoinducer, 2-heptyl-3-hydroxy-4(1H)-quinolone, known as *Pseudomonas* quinolone signal (PQS). The LysR-type transcriptional regulator PqsR binds PQS and controls a separate regulon. Under standard laboratory conditions, Las induces expression of both the Rhl and Pqs systems. Once active, the Pqs system positively regulates Rhl and Rhl represses Pqs. Las has typically been viewed as the master regulator of the QS systems; however, studies have indicated that this regulatory scheme is nutritionally and environmentally dependent.

Many research groups have targeted the individual QS systems in *P. aeruginosa* to identify non-native small molecules and macromolecules that attenuate certain virulence phenotypes in the wild-type bacterium. Most studies have focused on LasR and reported compounds that inhibit LasR at low micromolar concentrations and reduce the production of various virulence factors, Muh et al. (2006), Amara et al. (2009), Hodgkinson et al. 2012, Geske et al. (2005), Geske et al. (2007), Geske et al. (2008a), Geske et al. (2008b), and Mattmann et al. (2011). See FIG. 2 for exemplary LasR inhibitors.

The present invention relates to certain compounds which exhibit potent and efficient inhibition of QS in Gram-negative bacteria, particularly of *Pseudomonas* strains and more particularly of *P. aeruginosa* strains.

U.S. published application US 2009/0123512 (May 2009) relates to QS modulators of formula:

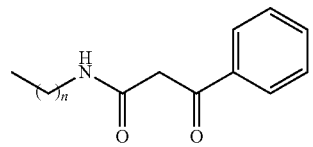

where n is 3-13.

U.S. Pat. No. 7,659,409 relates to a method for synthesis of 3-hydroxy 3-(2-thienyl)propionamides which are reported to be useful as synthetic intermediates of pharmaceutical preparations and a method for obtaining optically active 3-amino-1-(2-thienyl)-1-propanols. The patent reports the asymmetric reduction of a compound of generic formula:

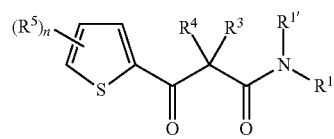

to produce compounds of formula:

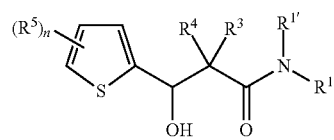

where
$R^1$ and $R^{1'}$ each independently represents hydrogen, alkyl, aryl or aralkyl,
$R^3$ and $R^4$ each independently represents hydrogen, or alkyl and may together form a carbon ring, $R^5$ represents a halogen, nitro, hydroxyl, alkyl which may be substituted, an aryl group which may be substituted, or an alkoxy which may be substituted, and n is 0 to 3.

U.S. published patent application 2006/0264641 relates to a process for preparing enantiomer-enriched 3-heteroaryl-1-aminopropan-3-ols which are said to have industrial significance as intermediates for preparation of medicaments. The process involves reaction of a compound of formula:

Heteroaryl-CO—CH$_2$—W, where W is among others $C(O)YR^1{}_n$, where Y is oxygen and n is 1 or Y is nitrogen and n is 2; and each $R^1$ independently is hydrogen C1-C8 alkyl, C4-C10 aryl, or C5-C11-arylalkyl or when Y is N, the two $R^1$ together are C3-C5 alkylene with certain amines in the presence of a microorganism.

SUMMARY OF THE INVENTION

The invention relates generally to compounds which modulate quorum sensing in Gram-negative bacteria. More specifically, compounds of the invention inhibit quorum sensing. More specifically, compounds of the invention inhibit LasR. More specifically, compounds of the invention inhibit quorum sensing in strains of *Pseudomonas*, and particularly in pathogenic strains of *Pseudomonas*. More specifically, compounds of the invention inhibit quorum sensing in strains of *Pseudomonas* which form biofilms. More specifically, compounds of the invention inhibit quorum sensing in strains of *Pseudomonas aeruginosa* and *Pseudomonas putida* which form biofilms. More specifically, compounds of the invention inhibit quorum sensing in strains of *Pseudomonas aeruginosa*.

Compounds of the invention include those of formula I and formula II:

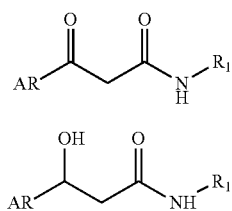

where:

AR is an optionally substituted phenyl, an optionally substituted cycloalkyl or cycloalkenyl or an optionally substituted heterocyclic group; and $R_1$ is an optionally substituted straight-chain or branched alkyl group or alkenyl group having 3-18 carbon atoms or is an optionally substituted straight-chain or branched alkyl group having 2-18 carbon atoms wherein one or more non-adjacent —CH$_2$— moieties are replaced with —O— or —S—, with the exception that for compounds of formula I, AR is not unsubstituted phenyl; or R1 is a C1-C4 alkyl group substituted at the omega position in the alkyl chain with an optionally substituted phenyl, cyclohexyl or cyclohexenyl group.

In an embodiment of formula I, AR is a substituted phenyl. In an embodiment of formula I, AR is hydroxyl- or fluoro-substituted phenyl.

In an embodiment of formula II, AR is an unsubstituted phenyl group. In a specific embodiment of formula II, AR is a substituted phenyl group.

In an embodiment, $R_1$ is a straight-chain or branched alkyl group having 6-13 carbon atoms. In an embodiment, $R_1$ is a straight-chain or branched alkyl group having 8-13 carbon atoms. In an embodiment, $R_1$ is a straight-chain or branched alkyl group having 9-13 carbon atoms. In an embodiment, $R_1$ is a straight-chain alkyl or branched alkyl group having 9-12 carbon atoms. In an embodiment, $R_1$ is a straight-chain alkyl having 6-13 carbon atoms. In an embodiment, $R_1$ is a straight-chain alkyl having 9-13 carbon atoms. In an embodiment, $R_1$ is a straight-chain alkyl group having 9-12 carbon atoms.

In an embodiment, $R_1$ is an unsubstituted straight-chain or branched alkyl group having 3-16 carbon atoms. In an embodiment, $R_1$ is an unsubstituted straight-chain or branched alkyl group having 3-13 carbon atoms. In an embodiment, $R_1$ is an unsubstituted straight-chain or branched alkyl group having 6-13 carbon atoms. In an embodiment, $R_1$ is an unsubstituted straight-chain or branched alkyl group having 6-12 carbon atoms. In an embodiment, $R_1$ is an unsubstituted straight-chain or branched alkyl group having 8-11 carbon atoms. In an embodiment, $R_1$ is an unsubstituted straight-chain or branched alkyl group having 8-10 carbon atoms. In an embodiment, $R_1$ is an unsubstituted straight-chain or branched alkyl group having 8-13 carbon atoms. In an embodiment, $R_1$ is an unsubstituted straight-chain or branched alkyl group having 9-13 carbon atoms. In an embodiment, $R_1$ is an unsubstituted straight-chain alkyl or branched alkyl group having 9-12 carbon atoms. In an embodiment, $R_1$ is an unsubstituted straight-chain alkyl having 6-13 carbon atoms. In an embodiment, $R_1$ is an unsubstituted straight-chain alkyl having 9-13 carbon atoms. In an embodiment, $R_1$ is an unsubstituted straight-chain alkyl group having 9-12 carbon atoms.

In an embodiment, $R_1$ is other than an alkoxy or alkylthio (alkyl-S—) group.

In an embodiment, $R_1$ is a straight-chain or branched alkenyl group having 5-12 carbon atoms. In an embodiment, $R_1$ is a straight-chain or branched alkenyl group having 9-12 carbon atoms. In an embodiment, $R_1$ is a straight-chain alkenyl having 5-12 carbon atoms. In an embodiment, $R_1$ is a straight-chain alkenyl having 9-12 carbon atoms. In an embodiment, $R_1$ is a straight-chain alkenyl having 5-12 carbon atoms having one double bond at the 3-4, 4-5, 5-6 or 6-7 positions of the alkenyl group.

In an embodiment, $R_1$ is an optionally substituted straight-chain or branched alkyl group having 2-18 carbon atoms wherein one or more non-adjacent —CH$_2$— moieties are replaced with —O— or —S—, except that $R_1$ is not an alkoxy or an alkyl thio group. Such groups can be designated ether groups or thioether groups, respectively, herein. Alternatively, such groups can be designated alkoxyalkyl groups or alkylthioalkyl groups, respectively. In embodiments, such groups have 1-4 oxygens or 1-4 sulfur atoms.

In an embodiment, $R_1$ is an unsubstituted straight-chain or branched alkyl group having 3-16 carbon atoms wherein one or more non-adjacent —CH$_2$— moieties are replaced with —O—. In an embodiment, $R_1$ is an unsubstituted straight-chain or branched alkyl group having 3-16 carbon atoms wherein one or more non-adjacent —CH$_2$— moieties are replaced with —S—. In an embodiment, $R_1$ is an unsubstituted straight-chain or branched alkyl group having 3-13 carbon atoms wherein one or more non-adjacent —CH$_2$— moieties are replaced with —O—. In an embodiment, $R_1$ is an unsubstituted straight-chain or branched alkyl group having 3-13 carbon atoms wherein one or more non-adjacent —CH$_2$— moieties are replaced with —S—. In more specific embodiments, such R$_1$ groups have 4-10 carbon atoms. In more specific embodiments, such R$_1$ groups have 4-8 carbon atoms. In more specific embodiments, such R$_1$ groups have 2-4 oxygen atoms in the group or 2-4 sulfur atoms in the group.

In an embodiment, R$_1$ is an unsubstituted straight-chain alkyl group having 3-16 carbon atoms wherein one or more non-adjacent —CH$_2$— moieties are replaced with —O—. In an embodiment, R$_1$ is an unsubstituted straight-chain alkyl group having 3-16 carbon atoms wherein one or more non-adjacent —CH$_2$— moieties are replaced with —S—. In an embodiment, R$_1$ is an unsubstituted straight-chain alkyl group having 3-13 carbon atoms wherein one or more non-adjacent —CH$_2$— moieties are replaced with —O—. In an embodiment, R$_1$ is an unsubstituted straight-chain alkyl group having 3-13 carbon atoms wherein one or more non-adjacent —CH$_2$— moieties are replaced with —S—. In more specific embodiments, such R$_1$ groups have 4-10 carbon atoms. In more specific embodiments, such R$_1$ groups have 4-8 carbon atoms. In more specific embodiments, such R$_1$ groups have 2-4 oxygen atoms in the group or 2-4 sulfur atoms in the group. In more specific embodiments, such R$_1$ groups have 1-4 oxygen atoms and 4-11 carbon atoms in the group or 1-4 sulfur atoms and 4-11 carbon atoms in the group.

In an embodiment, AR is a phenyl group substituted with 1-5 non-hydrogen substituents. In an embodiment, AR is a phenyl ring substituted with one or more halogen, hydroxyl, alkoxy or NH$_2$ groups. In an embodiment, AR is a phenyl ring substituted with one to three hydroxyl or halogen. In an embodiment, AR is a phenyl ring substituted with one or two hydroxyl or halogen. In an embodiment, AR is a phenyl ring substituted with one hydroxyl or halogen. In an embodiment, AR is a phenyl ring substituted with one hydroxyl group. In an embodiment, AR is a phenyl ring substituted with a hydroxyl in the meta ring position. In an embodiment, AR is a phenyl ring substituted with a hydroxyl in the ortho ring position. In an embodiment, AR is a phenyl ring substituted with one halogen, particularly a fluorine. In an embodiment, AR is a phenyl ring substituted with a halogen, particularly a fluorine, in the meta ring position. In an embodiment, AR is a phenyl ring substituted with a halogen, particularly a fluorine, in the ortho ring position.

In an embodiment, AR is an unsubstituted 5- or 6-member ring cycloakyl group. In an embodiment, AR is an unsubstituted 5- or 6-member ring cycloakenyl group. In an embodiment, AR is an unsubstituted 5- or 6-member ring cycloakenyl group having a single double bond in the ring.

In an embodiment, AR is an unsubstituted heteroaryl group.

In an embodiment, AR is an unsubstituted furyl group. In an embodiment, AR is an unsubstituted fur-2-yl group. In an embodiment, AR is an unsubstituted fur-3-yl group.

In an embodiment, AR is an unsubstituted thiophenyl group. In an embodiment, AR is an unsubstituted thiophen-2-yl group. In an embodiment, AR is an unsubstituted thiophen-3-yl group.

In an embodiment, AR is an unsubstituted pyridyl group. In an embodiment, AR is an unsubstituted pyrid-2-yl group. In an embodiment, AR is an unsubstituted pyrid-3-yl group.

In an embodiment, AR is an unsubstituted thiazolyl group. In an embodiment, AR is an unsubstituted thiazol-2-yl group. In an embodiment, AR is an unsubstituted thiazol-3-yl group.

In another aspect, the invention provides compound of formulas XX and XXI:

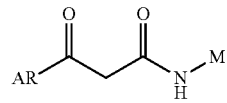

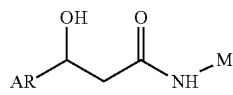

where AR is as defined in formula I or II, or embodiments thereof, and

M is an alkyl group having 1-3 carbon atoms that is substituted at the distal position with an optionally substituted phenyl group, a cycloalkyl, a cycloalkenyl group, or a branched alkyl group having 4-12 carbon atoms with a branch at the 1-position in the group.

Specific M groups include:

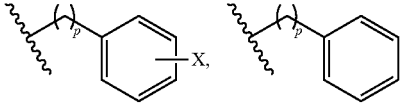

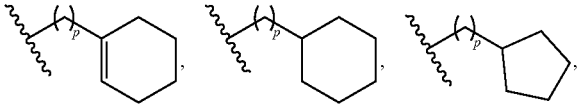

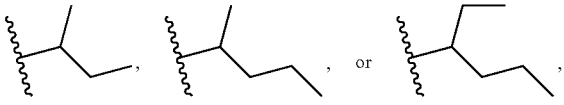

where p is 1, 2 or 3 and preferably 1 or 2; and X is a substituent for a phenyl group as described in formulas III, IVA or IVB below. Compounds of formula XX and XXI are modulators of LasR. Certain compounds of formula XX and XXI are inhibitors of LasR.

The invention also relates to the use of one or more compounds of the invention to inhibit quorum sensing in a Gram-negative bacterium, particularly in a strain of *Pseudomonas* and more particularly in a strain of *Pseudomonas aeruginosa*. The invention further relates to prevention or inhibition of biofilm formation and/or the eradication of existing (already-formed) biofilms. The invention provides a method for inhibition of biofilm formation or the eradication of already-formed biofilm by contacting the bacterium capable of producing a biofilm or the biofilm environment with one or more compounds of the invention. The invention also provides a method for inhibition of generation and/or release of virulence factors from a Gram-negative bacterium, particularly a strain of *Pseudomonas* and more particularly a strain of *Pseudomonas aeruginosa*.

The invention further relates to a method for treating an infection of a Gram-negative bacterium in a subject in need of such treatment. The subject may be an animal. The subject may be a non-human animal. The subject may be a mammal. The subject may be a non-human mammal. The subject may be a human. Subject animals include, among others, cats, dogs, horses, cows, and sheep.

The invention further relates to the use of one or more compounds of the invention for treatment of an infection of a Gram-negative bacterium. The invention also relates to the use of one or more compounds of the invention for making a medicament for the treatment of an infection of a Gram-negative bacterium. In specific embodiments, the Gram-negative bacterium is a strain of *Pseudomonas*. In specific embodiments, the Gram-negative bacterium is a strain of *Pseudomonas aeruginosa*.

The invention also relates to a method of using one or more compounds to inhibit quorum sensing in vitro, particularly in an in vitro environment contaminated with a Gram-negative bacterium. In specific embodiments, the Gram-negative bacterium is a strain of *Pseudomonas*. In specific embodiments, the Gram-negative bacterium is a strain of *Pseudomonas aeruginosa*. The term in vitro is used generally herein to exclude in vivo administration. In vitro use of compounds herein includes applications to inanimate objects, such as application to surfaces of inanimate objects, e.g., table tops, appliances, medical instruments, metal or plastic pans or trays. Compounds herein may be applied to such inanimate objects in a coating, layer or by spraying.

Further aspects and embodiments of the invention are apparent to one of ordinary skill in the art on review of the detailed description, drawings and examples.

BRIEF DESCRIPTION OF THE FIGURES

FIG. 12A is a bar graph of % elastase as a function of the indicated compound or mixture. FIG. 12B illustrates the chemical structures of the compounds compared in FIG. 12A (noting that M is M64 and V is V-060018). Compound 33 inhibits the production of virulence factor elastase. Compounds 30, 33 and 40 inhibit elastase synergistically with PqsR inhibitor M64.

DETAILED DESCRIPTION OF THE INVENTION

Figure 1:
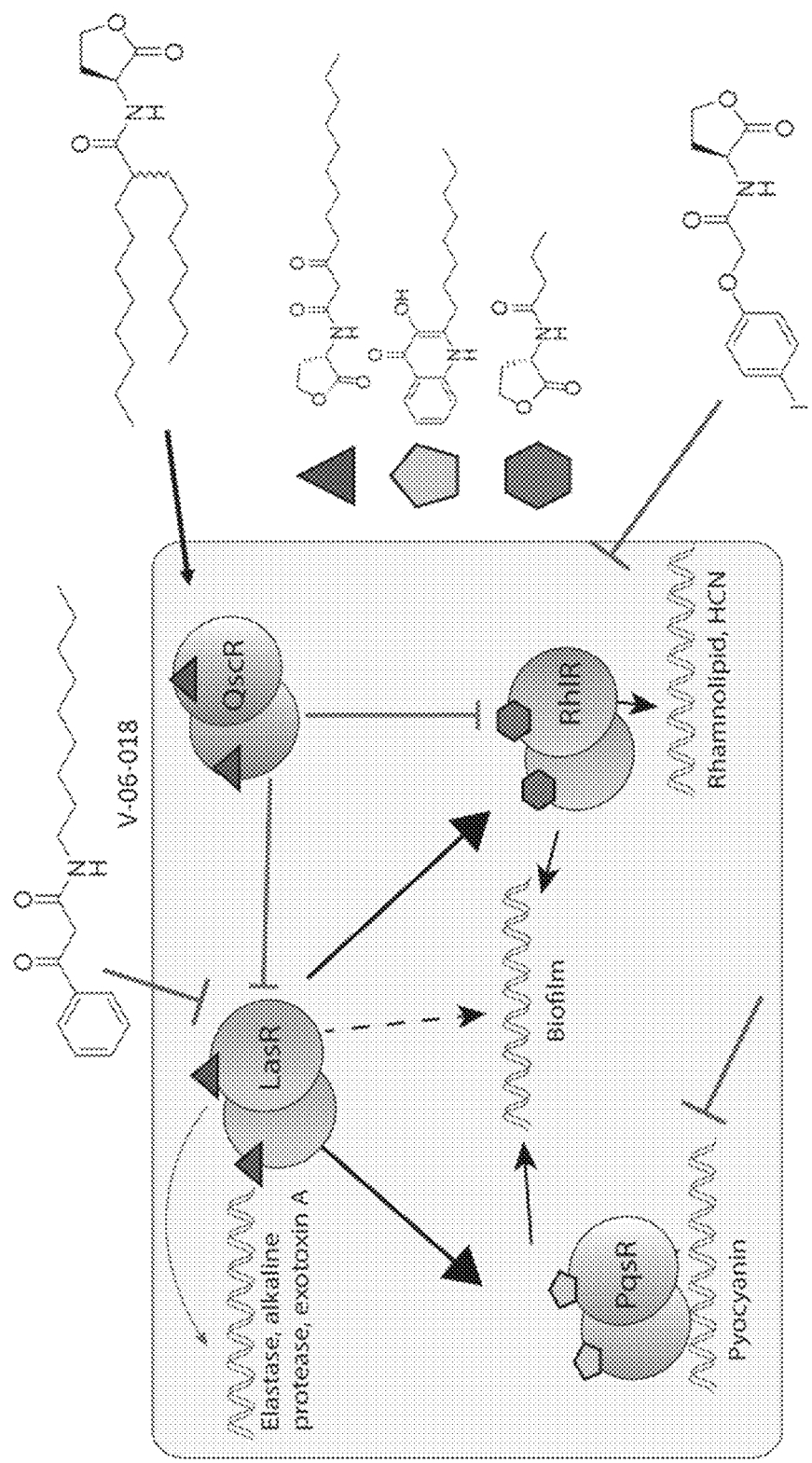
FIG. 1 is a schematic illustration of the three Quorum Sensing circuits in the exemplary Gram-negative bacterium *Pseudomonas aeruginosa*. The chemical structures of the natural autoinducers for each system are illustrated next to the triangle, pentagon and hexagon. Exemplary inhibitors of each circuit are also illustrated.
Figure 2A:
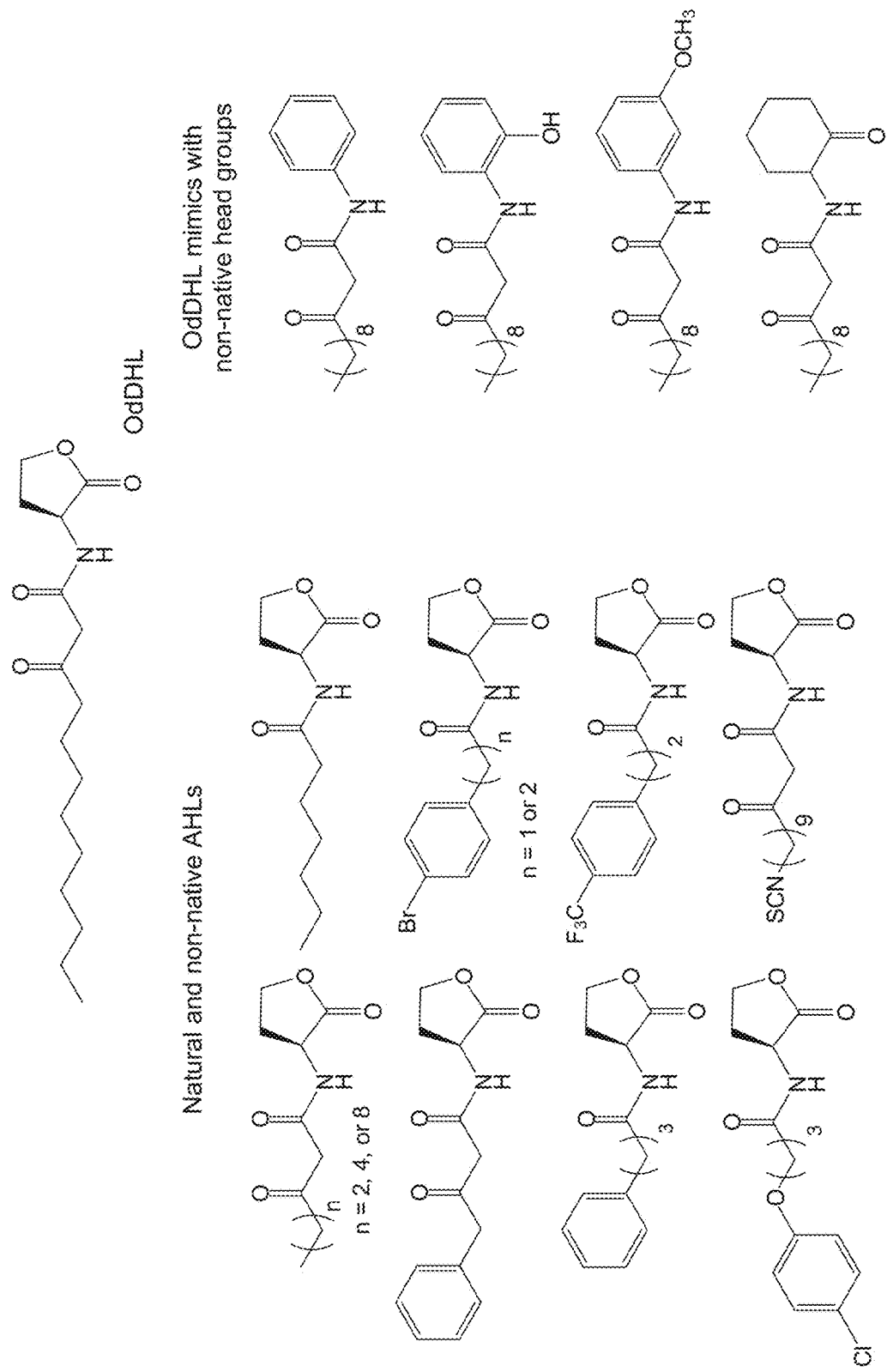
FIGS. 2A and 2B illustrate chemical structures of exemplary inhibitors of LasR. OdDHL is the natural autoinducer.
Figure 2B:
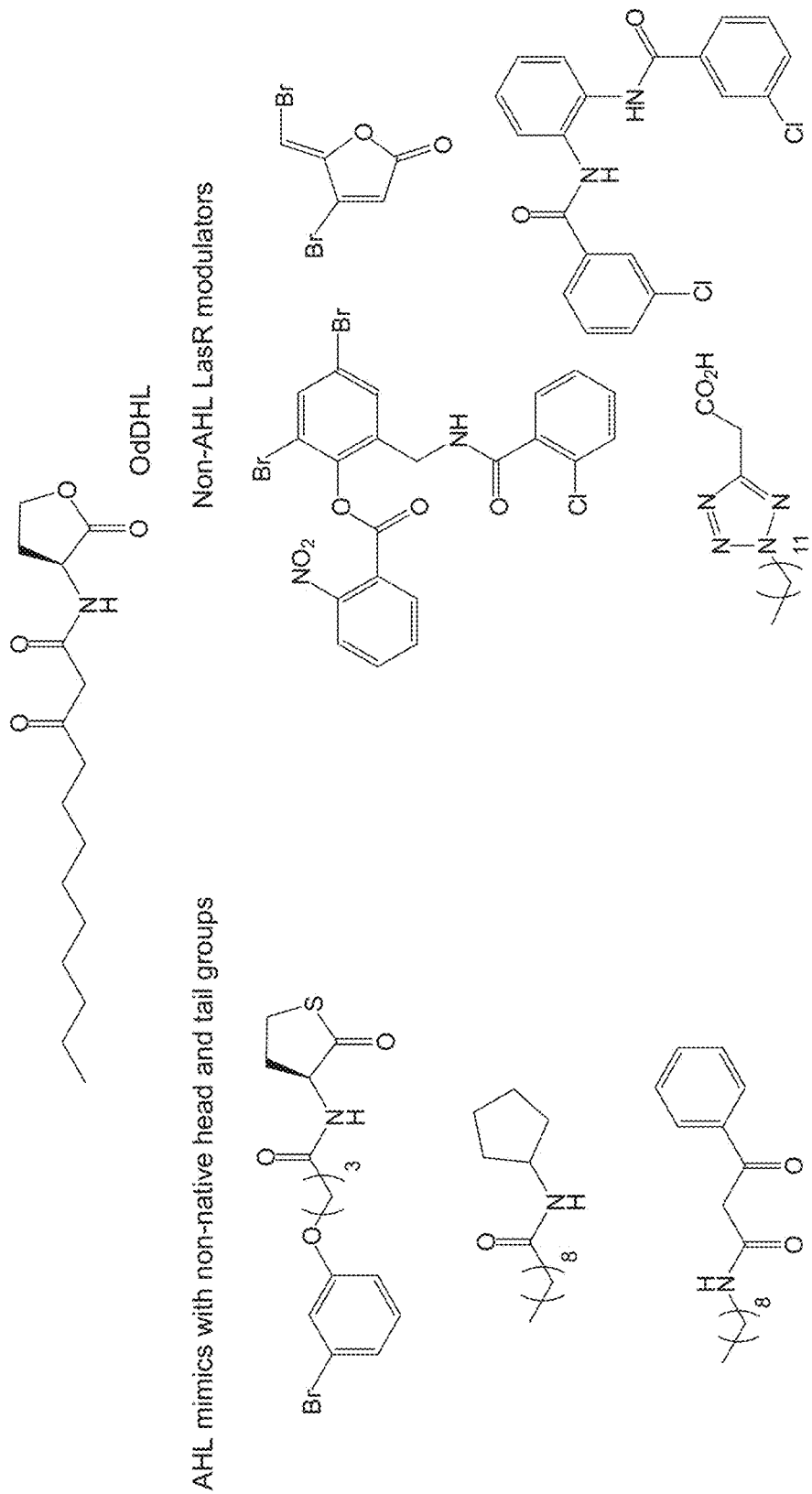

The present invention relates to modulators of QS in Gram-negative bacteria and more particularly to inhibitors of QS in Gram-negative bacteria.

In specific embodiments, compounds of the invention are those of formula I or those of formula II:

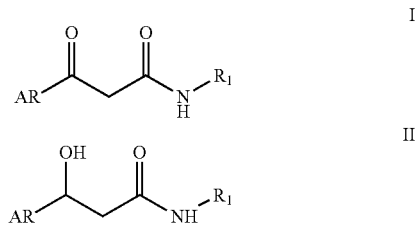

where:

AR is a substituted phenyl, an optionally substituted cycloalkyl or cycloalkenyl or an optionally substituted heterocyclic group; and $R_1$ is an optionally substituted straight-chain or branched alkyl group or alkenyl group having 3-16 carbon atoms or an optionally substituted straight-chain or branched alkyl group wherein one or more non-adjacent —$CH_2$— group is replaced with an oxygen or a sulfur atom; or $R_1$ is a C1-C4 alkyl substituted at the omega position or distal end of the alkyl with an optionally-substituted phenyl, cyclohexyl or cyclohexenyl group.

In an embodiment optional substitution is substitution with one or more non-hydrogen substituents selected from halogen, hydroxyl, alkyl, alkoxy and amino (—$NH_2$). Halogen substituents include fluorine, chlorine, bromine and iodine. A preferred halogen is fluorine. Preferred alkyl and alkoxy substituents have 1-3 carbon atoms. In specific embodiments, substitution is with one, two or three of the listed groups. In specific embodiments, substitution is with one or two of the listed groups. In specific embodiments, substitution is with one of the listed groups. In specific embodiments, $R_1$ groups are not substituted.

In specific embodiments, $R_1$ is an unsubstituted alkyl group having 3-16 carbon atoms. In an embodiment, $R_1$ is an unsubstituted alkyl group having 5-13 carbon atoms. In an embodiment, $R_1$ is an unsubstituted alkyl group having 6-13 carbon atoms. In an embodiment, $R_1$ is an unsubstituted alkyl group having 7-13 carbon atoms. In an embodiment, $R_1$ is an unsubstituted alkyl group having 8-13 carbon atoms. In an embodiment, $R_1$ is an unsubstituted alkyl group having 9-13 carbon atoms. In an embodiment, $R_1$ is an unsubstituted alkyl group having 9-12 carbon atoms. In an embodiment, $R_1$ is n-heptyl. In an embodiment, $R_1$ is n-octyl. In an embodiment, $R_1$ is n-nonyl. In an embodiment, $R_1$ is n-decyl. In an embodiment, $R_1$ is n-undecyl. In an embodiment, $R_1$ is n-dodecyl.

In specific embodiments, $R_1$ is an unsubstituted alkenyl group having 3-16 carbon atoms. In an embodiment, $R_1$ is an unsubstituted alkenyl group having 5-13 carbon atoms. In an embodiment, $R_1$ is an unsubstituted alkenyl group having 9-12 carbon atoms. In an embodiment, $R_1$ is n-non-3-enyl. In an embodiment, $R_1$ is n-non-4-enyl.

In an embodiment, $R_1$ is n-non-5-enyl. In an embodiment, $R_1$ is n-non-6-enyl. In an embodiment, $R_1$ is n-dec-3-enyl. In an embodiment, $R_1$ is n-dec-4-enyl. In an embodiment, $R_1$ is n-dec-5-enyl. In an embodiment, $R_1$ is n-dec-6-enyl. In an embodiment, $R_1$ is n-dec-7-enyl. In an embodiment, $R_1$ is n-undec-3-enyl. In an embodiment, $R_1$ is n-undec-4-enyl. In an embodiment, $R_1$ is n-undec-5-enyl. In an embodiment, $R_1$ is n-undec-6-enyl. In an embodiment, $R_1$ is n-undec-7-enyl. In an embodiment, $R_1$ is n-undec-8-enyl. In an embodiment, $R_1$ is n-dodec-3-enyl. In an embodiment, $R_1$ is n-dodec-4-enyl. In an embodiment, $R_1$ is n-dodec-5-enyl. In an embodiment, $R_1$ is n-dodec-6-enyl. In an embodiment, $R_1$ is n-dodec-7-enyl. In an embodiment, $R_1$ is n-dodec-8-enyl. In an embodiment, $R_1$ is n-dodec-9-enyl.

In specific embodiments, $R_1$ is not an alkoxy or an alkylthio group.

In specific embodiments, $R_1$ is an alkoxyalkyl group having 1-4 oxygen atoms and 2-18 carbon atoms. In specific embodiments, $R_1$ is an alkyloxyalkyl group having 1-4 oxygen atoms and 4-11 carbon atoms. In specific embodiments, $R_1$ is an alkyloxyalkyl group having 2-4 oxygen atoms and 3-18 carbon atoms. In specific embodiments, $R_1$ is an alkyloxyalkyl group having 2-4 oxygen atoms and 4-11 carbon atoms. In specific embodiments, $R_1$ is a group having formula: $-[-(CH_2)_n-O-]_p-R_{10}$, where n is 1, 2 or 3, p is 1-4 and $R_{10}$ is a C1-C6 alkyl group. In specific embodiments, $R_1$ is a group having formula: $-[-(CH_2)_n-O-]_p-R_{10}$, where n is 2 or 3, p is 2-4 and $R_{10}$ is a C1-C3 alkyl group. In specific embodiments, $R_1$ is $-CH_2-CH_2-O-CH_2-CH_2-O-R_{10}$, where $R_{10}$ is C1-C3 alkyl. In specific embodiments, $R_1$ is $-CH_2-CH_2-O-CH_2-CH_2-O-CH_2-CH_2-CH_3$.

In specific embodiments, $R_1$ is an alkylthioalkyl group having 1-4 sulfur atoms and 2-18 carbon atoms. In specific embodiments, $R_1$ is an alkylthioalkyl group having 1-4 sulfur atoms and 4-11 carbon atoms. In specific embodiments, $R_1$ is an alkylthioalkyl group having 2-4 sulfur atoms and 3-18 carbon atoms. In specific embodiments, $R_1$ is an alkylthioalkyl group having 2-4 sulfur atoms and 4-11 carbon atoms. In specific embodiments, $R_1$ is a group having formula: $-[-(CH_2)_n-S-]_p-R_{10}$, where n is 1, 2 or 3, p is 1-4 and $R_{10}$ is a C1-C6 alkyl group. In specific embodiments, $R_1$ is a group having formula: $-[-(CH_2)_n-S-]_p-R_{10}$, where n is 2 or 3, p is 2-4 and $R_{10}$ is a C1-C3 alkyl group. In specific embodiments, $R_1$ is $-CH_2-CH_2-S-CH_2-CH_2-S-R_{10}$, where $R_{10}$ is C1-C3 alkyl. In specific embodiments, $R_1$ is $-CH_2-CH_2-S-CH_2-CH_2-S-CH_2-CH_2-CH_3$.

In specific embodiments, $R_1$ is a straight-chain C1-C4 alkyl substituted at the omega position on the alkyl chain with an optionally substituted phenyl. In an embodiment, the optionally substituted phenyl is a p-substituted alkoxy or halogen. In an embodiment, the phenyl is unsubstituted.

In specific embodiments, AR is a substituted phenyl group. In specific embodiments, AR is a hydroxyl-substituted phenyl group. In specific embodiments, AR is a halogen-substituted phenyl group. In specific embodiments, AR is a fluorine-substituted phenyl group. In specific embodiments, AR is a meta-hydroxyl-substituted phenyl group. In specific embodiments, AR is an ortho-hydroxyl-substituted phenyl group. In specific embodiments, AR is a para-hydroxyl-substituted phenyl group. In specific embodiments, AR is an ortho-halogen-substituted phenyl group. In specific embodiments, AR is a meta-halogen-substituted phenyl group. In specific embodiments, AR is a para-halogen-substituted phenyl group. In specific embodiments, AR is an ortho-fluorine-substituted phenyl group. In specific embodiments, AR is a meta-fluorine substituted phenyl group. In specific embodiments, AR is a para-fluorine-substituted phenyl group.

In specific embodiments, AR is a cycloalkyl group. In specific embodiments, AR is a cyclopentyl group. In specific embodiments, AR is a cyclohexyl group. In specific embodiments, AR is a cycloalkenyl group. In specific embodiments, AR is a cyclopentenyl group. In specific embodiments, AR is a cyclohexenyl group. In specific embodiments, AR is a cyclopent-2-enyl group. In specific embodiments, AR is a cyclohex-2-enyl group. In specific embodiments, AR is a cyclopent-3-enyl group. In specific embodiments, AR is a cyclohex-3-enyl group.

In specific embodiments, AR is a furyl or thiophenyl group. In specific embodiments AR is:

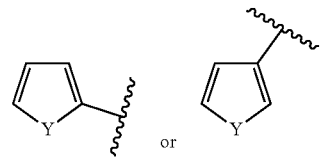

where Y is —O— or —S—.

In specific embodiments, compounds of the invention are those of formula III:

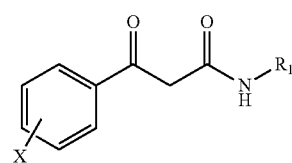

III where $R_1$ is as defined for formula I, and any embodiments thereof, and X represents 1-5 non-hydrogen substituents on the phenyl ring. In specific embodiments, X is halogen, hydroxyl, alkyl, alkoxy or amino. More specifically, X is iodine, chlorine, bromine, fluorine, hydroxyl or methoxy. In specific embodiments, X is fluorine, hydroxyl or methoxy. In specific embodiments, X is m-fluorine, o-fluorine, p-fluorine, m-hydroxyl, o-hydroxyl, p-hydroxyl, o-methoxy, m-methoxy or p-methoxy.

In specific embodiments, compounds of the invention are those of formula IVA:

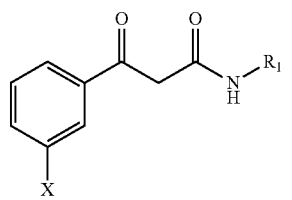

IVA where $R_1$ is as defined for formula I, or any embodiments thereof, and X is as defined for formula III, or any embodiments thereof. More specifically, X is halogen or hydroxyl. In specific embodiments, halogen is fluorine. In specific embodiments, X is hydroxyl.

In specific embodiments, compounds of the invention are those of formula IVB:

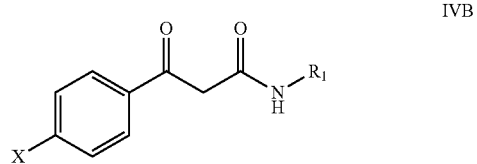

IVB where $R_1$ is as defined for formula I, or any embodiments thereof, and X is as defined for formula III, or any embodiments thereof. More specifically X is halogen or hydroxyl. In specific embodiments, halogen is fluorine. In specific embodiments, X is hydroxyl.

In specific embodiments of formulas III, IVA and IVB, $R_1$ is a straight-chain or branched alkyl having 8-12 carbon atoms. In specific embodiments of formulas III, IVA and IVB, $R_1$ is an alkyl having 9-12 carbon atoms. In specific embodiments of formulas III, IVA and IVB, $R_1$ is an alkenyl having 9-12 carbon atoms. In specific embodiments of formulas III, IVA and IVB, $R_1$ is an alkenyl having 5-12 carbon atoms. In specific embodiments of formulas III, IVA and IVB, $R_1$ is an unsubstituted straight-chain or branched alkyl group having 3-16 carbon atoms wherein one or more non-adjacent —$CH_2$— moieties are replaced with —O—. In embodiments of formulas III, IVA and IVB, $R_1$ is an unsubstituted straight-chain or branched alkyl group having 3-16 carbon atoms wherein one or more non-adjacent —$CH_2$— moieties are replaced with —S—. In embodiments of formulas III, IVA and IVB, $R_1$ is an unsubstituted straight-chain or branched alkyl group having 3-13 carbon atoms wherein one or more non-adjacent —$CH_2$— moieties are replaced with —O—. In embodiments of formulas III, IVA and IVB, $R_1$ is an unsubstituted straight-chain or branched alkyl group having 3-13 carbon atoms wherein one or more non-adjacent —$CH_2$— moieties are replaced with —S—. In more specific embodiments of formulas III, IVA and IVB, such $R_1$ groups have 4-10 carbon atoms. In more specific embodiments, such $R_1$ groups have 4-8 carbon atoms. In more specific embodiments, such $R_1$ groups have 2-4 oxygen atoms in the group or 2-4 sulfur atoms in the group.

In specific embodiments of formulas II, IVA and IVB, $R_1$ is an alkoxyalkyl group having 1-4 oxygen atoms and 2-18 carbon atoms. In specific embodiments of formulas II, IVA and IVB, $R_1$ is an alkyloxyalkyl group having 1-4 oxygen atoms and 4-11 carbon atoms.

In specific embodiments of formulas II, IVA and IVB, $R_1$ is an alkyloxyalkyl group having 2-4 oxygen atoms and 3-18 carbon atoms. In specific embodiments of formulas II, IVA and IVB, $R_1$ is an alkyloxyalkyl group having 2-4 oxygen atoms and 4-11 carbon atoms. In specific embodiments of formulas II, IVA and IVB, $R_1$ is a group having formula: -[—$(CH_2)_n$—O—$]_p$—$R_{10}$, where n is 1, 2 or 3, p is 1-4 and $R_{10}$ is a C1-C6 alkyl group.

In specific embodiments, $R_1$ is a group having formula: -[—$(CH_2)_n$—O—$]_p$—$R_{10}$, where n is 2 or 3, p is 2-4 and $R_{10}$ is a C1-C3 alkyl group. In specific embodiments of formulas II, IVA and IVB, $R_1$ is —$CH_2$—$CH_2$—O—$CH_2$—$CH_2$—O—$R_{10}$, where $R_{10}$ is C1-C3 alkyl. In specific embodiments, $R_1$ is —$CH_2$—$CH_2$—O—$CH_2$—$CH_2$—O—$CH_2$—$CH_2$—$CH_3$.

In specific embodiments of formulas II, IVA and IVB, $R_1$ is an alkylthioalkyl group having 1-4 sulfur atoms and 2-18 carbon atoms. In specific embodiments of formulas II, IVA and IVB, $R_1$ is an alkylthioalkyl group having 1-4 sulfur atoms and 4-11 carbon atoms. In specific embodiments of formulas II, IVA and IVB, $R_1$ is an alkylthioalkyl group having 2-4 sulfur atoms and 3-18 carbon atoms. In specific embodiments of formulas II, IVA and IVB, $R_1$ is an alkylthioalkyl group having 2-4 sulfur atoms and 4-11 carbon atoms. In specific embodiments of formulas II, IVA and IVB, $R_1$ is a group having formula: -[—$(CH_2)_n$—S—$]_p$—$R_{10}$, where n is 1, 2 or 3, p is 1-4 and $R_{10}$ is a C1-C6 alkyl group. In specific embodiments of formulas II, IVA and IVB, $R_1$ is a group having formula: -[—$(CH_2)_n$—S—$]_p$—$R_{10}$, where n is 2 or 3, p is 2-4 and $R_{10}$ is a C1-C3 alkyl group. In specific embodiments of formulas II, IVA and IVB, $R_1$ is —$CH_2$—$CH_2$—S—$CH_2$—$CH_2$—S—$R_{10}$, where $R_{10}$ is C1-C3 alkyl. In specific embodiments of formulas II, IVA and IVB, $R_1$ is —$CH_2$—$CH_2$—S—$CH_2$—$CH_2$—S—$CH_2$—$CH_2$—$CH_3$.

In specific embodiments, compounds of the invention are those of formulas I or II where AR is naphthyl or benzodioxolyl. More specifically, AR is:

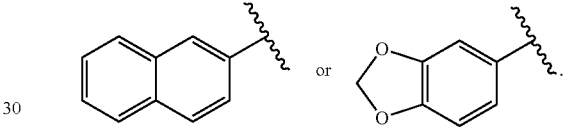

In specific embodiments, compounds of the invention are those of formulas I or II where AR is optionally substituted furyl and more specifically optionally substituted fur-2-yl or fur-3-yl. More specifically, AR is hydroxyl substituted furyl, including 5-OH fur-2-yl or 5-OH fur-3-yl.

In specific embodiments, compounds of the invention are those of formula VA:

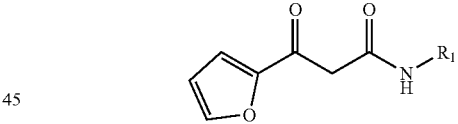

where $R_1$ is as defined for formula, or any embodiments thereof. In specific embodiments, $R_1$ is an alkyl having 9-12 carbon atoms. In specific embodiments, $R_1$ is an alkenyl having 5-12 carbon atoms. In specific embodiments, $R_1$ is an alkenyl having 9-12 carbon atoms. In specific embodiments, $R_1$ is an unsubstituted straight-chain or branched alkyl group having 3-16 carbon atoms wherein one or more non-adjacent —$CH_2$— moieties are replaced with —O—. In embodiments, $R_1$ is an unsubstituted straight-chain or branched alkyl group having 3-16 carbon atoms wherein one or more non-adjacent —$CH_2$— moieties are replaced with —S—. In specific embodiments, $R_1$ is an alkoxyalkyl group having 1-4 oxygen atoms and 2-18 carbon atoms. In specific embodiments, $R_1$ is an alkoxyalkyl group having 1-4 oxygen atoms and 4-11 carbon atoms. In specific embodiments, $R_1$ is an alkoxyalkyl group having 2-4 oxygen atoms and 3-18 carbon atoms. In specific embodiments, $R_1$ is an alkoxyalkyl group having 2-4 oxygen atoms and 4-11 carbon atoms. In specific embodiments, $R_1$ is a group having formula: -[—$(CH_2)_n$—O—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—O—$]_p$—$R_{10}$, where n is 2 or 3, p is 2-4 and $R_{10}$ is a C1-C3 alkyl group. In specific embodiments, $R_1$ is —$CH_2$—$CH_2$—O—$CH_2$—$CH_2$—O—$R_{10}$, where $R_{10}$ is C1-C3 alkyl. In specific embodiments, $R_1$ is —$CH_2$—$CH_2$—O—$CH_2$—$CH_2$—O—$CH_2$—$CH_2$—$CH_3$. In specific embodiments, $R_1$ is an alkylthioalkyl group having 1-4 sulfur atoms and 2-18 carbon atoms. In specific embodiments, $R_1$ is an alkylthioalkyl group having 1-4 sulfur atoms and 4-11 carbon atoms. In specific embodiments, $R_1$ is an alkylthioalkyl group having 2-4 sulfur atoms and 3-18 carbon atoms. In specific embodiments, $R_1$ is an alkylthioalkyl group having 2-4 sulfur atoms and 4-11 carbon atoms. In specific embodiments, $R_1$ is a group having formula: -[—$(CH_2)_n$—S—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—S—$]_p$—$R_{10}$, where n is 2 or 3, p is 2-4 and $R_{10}$ is a C1-C3 alkyl group. In specific embodiments, $R_1$ is —$CH_2$—$CH_2$—S—$CH_2$—$CH_2$—S—$R_{10}$, where $R_{10}$ is C1-C3 alkyl. In specific embodiments, $R_1$ is —$CH_2$—$CH_2$—S—$CH_2$—$CH_2$—S—$CH_2$—$CH_2$—$CH_3$.

In specific embodiments, compounds of the invention are those of formula VB:

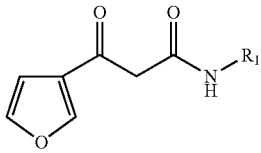

where $R_1$ is as defined for formula I, or any embodiments thereof. In specific embodiments, $R_1$ is an alkyl having 9-12 carbon atoms. In specific embodiments, $R_1$ is an alkenyl having 5-12 carbon atoms. In specific embodiments, $R_1$ is an alkenyl having 9-12 carbon atoms. In specific embodiments, $R_1$ is an unsubstituted straight-chain or branched alkyl group having 3-16 carbon atoms wherein one or more non-adjacent —$CH_2$— moieties are replaced with —O—. In embodiments, $R_1$ is an unsubstituted straight-chain or branched alkyl group having 3-16 carbon atoms wherein one or more non-adjacent —$CH_2$— moieties are replaced with —S—. In specific embodiments, $R_1$ is an alkoxyalkyl group having 1-4 oxygen atoms and 2-18 carbon atoms. In specific embodiments, $R_1$ is an alkoxyalkyl group having 1-4 oxygen atoms and 4-11 carbon atoms. In specific embodiments, $R_1$ is an alkoxyalkyl group having 2-4 oxygen atoms and 3-18 carbon atoms. In specific embodiments, $R_1$ is an alkoxyalkyl group having 2-4 oxygen atoms and 4-11 carbon atoms. In specific embodiments, $R_1$ is a group having formula: -[—$(CH_2)_n$—O—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—O—$]_p$—$R_{10}$, where n is 2 or 3, p is 2-4 and $R_{10}$ is a C1-C3 alkyl group. In specific embodiments, $R_1$ is —$CH_2$—$CH_2$—O—$CH_2$—$CH_2$—O—$R_{10}$, where $R_{10}$ is C1-C3 alkyl. In specific embodiments, $R_1$ is —$CH_2$—$CH_2$—O—$CH_2$—$CH_2$—O—$CH_2$—$CH_2$—$CH_3$. In specific embodiments, $R_1$ is an alkylthioalkyl group having 1-4 sulfur atoms and 2-18 carbon atoms. In specific embodiments, $R_1$ is an alkylthioalkyl group having 1-4 sulfur atoms and 4-11 carbon atoms. In specific embodiments, $R_1$ is an alkylthioalkyl group having 2-4 sulfur atoms and 3-18 carbon atoms. In specific embodiments, $R_1$ is an alkylthioalkyl group having 2-4 sulfur atoms and 4-11 carbon atoms. In specific embodiments, $R_1$ is a group having formula: -[—$(CH_2)_n$—S—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—S—$]_p$—$R_{10}$, where n is 2 or 3, p is 2-4 and $R_{10}$ is a C1-C3 alkyl group. In specific embodiments, $R_1$ is —$CH_2$—$CH_2$—S—$CH_2$—$CH_2$—S—$R_{10}$, where $R_{10}$ is C1-C3 alkyl. In specific embodiments, $R_1$ is —$CH_2$—$CH_2$—S—$CH_2$—$CH_2$—S—$CH_2$—$CH_2$—$CH_3$.

In specific embodiments, compounds of the invention are those of formula VIA:

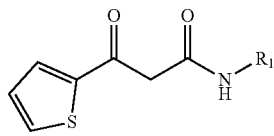

where $R_1$ is as defined for formula I, or any embodiments thereof. In specific embodiments, $R_1$ is an alkyl having 9-12 carbon atoms. In specific embodiments, $R_1$ is an alkenyl having 5-12 carbon atoms. In specific embodiments, $R_1$ is an alkenyl having 9-12 carbon atoms. In specific embodiments, $R_1$ is an unsubstituted straight-chain or branched alkyl group having 3-16 carbon atoms wherein one or more non-adjacent —$CH_2$— moieties are replaced with —O—. In embodiments, $R_1$ is an unsubstituted straight-chain or branched alkyl group having 3-16 carbon atoms wherein one or more non-adjacent —$CH_2$— moieties are replaced with —S—. In specific embodiments, $R_1$ is an alkoxyalkyl group having 1-4 oxygen atoms and 2-18 carbon atoms. In specific embodiments, $R_1$ is an alkoxyalkyl group having 1-4 oxygen atoms and 4-11 carbon atoms. In specific embodiments, $R_1$ is an alkoxyalkyl group having 2-4 oxygen atoms and 3-18 carbon atoms. In specific embodiments, $R_1$ is an alkoxyalkyl group having 2-4 oxygen atoms and 4-11 carbon atoms. In specific embodiments, $R_1$ is a group having formula: -[—$(CH_2)_n$—O—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—O—$]_p$—$R_{10}$, where n is 2 or 3, p is 2-4 and $R_{10}$ is a C1-C3 alkyl group. In specific embodiments, $R_1$ is —$CH_2$—$CH_2$—O—$CH_2$—$CH_2$—O—$R_{10}$, where $R_{10}$ is C1-C3 alkyl. In specific embodiments, $R_1$ is —$CH_2$—$CH_2$—O—$CH_2$—$CH_2$—O—$CH_2$—$CH_2$—$CH_3$. In specific embodiments, $R_1$ is an alkylthioalkyl group having 1-4 sulfur atoms and 2-18 carbon atoms. In specific embodiments, $R_1$ is an alkylthioalkyl group having 1-4 sulfur atoms and 4-11 carbon atoms. In specific embodiments, $R_1$ is an alkylthioalkyl group having 2-4 sulfur atoms and 3-18 carbon atoms. In specific embodiments, $R_1$ is an alkylthioalkyl group having 2-4 sulfur atoms and 4-11 carbon atoms. In specific embodiments, $R_1$ is a group having formula: -[—$(CH_2)_n$—S—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—S—$]_p$—$R_{10}$, where n is 2 or 3, p is 2-4 and $R_{10}$ is a C1-C3 alkyl group. In specific embodiments, $R_1$ is —$CH_2$—$CH_2$—S—$CH_2$—$CH_2$—S—$R_{10}$, where $R_{10}$ is C1-C3 alkyl. In specific embodiments, $R_1$ is —$CH_2$—$CH_2$—S—$CH_2$—$CH_2$—S—$CH_2$—$CH_2$—$CH_3$.

In specific embodiments, compounds of the invention are those of formula VIB:

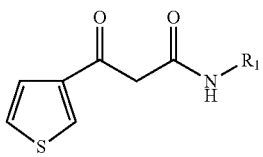

where $R_1$ is as defined for formula I, or any embodiments thereof. In specific embodiments, $R_1$ is an alkyl having 9-12 carbon atoms. In specific embodiments, $R_1$ is an alkenyl having 5-12 carbon atoms. In specific embodiments, $R_1$ is an alkenyl having 9-12 carbon atoms. In specific embodiments, $R_1$ is an unsubstituted straight-chain or branched alkyl group having 3-16 carbon atoms wherein one or more non-adjacent —$CH_2$— moieties are replaced with —O—. In embodiments, $R_1$ is an unsubstituted straight-chain or branched alkyl group having 3-16 carbon atoms wherein one or more non-adjacent —$CH_2$— moieties are replaced with —S—. In specific embodiments, $R_1$ is an alkoxyalkyl group having 1-4 oxygen atoms and 2-18 carbon atoms. In specific embodiments, $R_1$ is an alkoxyalkyl group having 1-4 oxygen atoms and 4-11 carbon atoms. In specific embodiments, $R_1$ is an alkoxyalkyl group having 2-4 oxygen atoms and 3-18 carbon atoms. In specific embodiments, $R_1$ is an alkoxyalkyl group having 2-4 oxygen atoms and 4-11 carbon atoms. In specific embodiments, $R_1$ is a group having formula: -[—$(CH_2)_n$—O—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—O—$]_p$—$R_{10}$, where n is 2 or 3, p is 2-4 and $R_{10}$ is a C1-C3 alkyl group. In specific embodiments, $R_1$ is —$CH_2$—$CH_2$—O—$CH_2$—$CH_2$—O—$R_{10}$, where $R_{10}$ is C1-C3 alkyl. In specific embodiments, $R_1$ is —$CH_2$—$CH_2$—O—$CH_2$—$CH_2$—O—$CH_2$—$CH_2$—$CH_3$. In specific embodiments, $R_1$ is an alkylthioalkyl group having 1-4 sulfur atoms and 2-18 carbon atoms. In specific embodiments, $R_1$ is an alkylthioalkyl group having 1-4 sulfur atoms and 4-11 carbon atoms. In specific embodiments, $R_1$ is an alkylthioalkyl group having 2-4 sulfur atoms and 3-18 carbon atoms. In specific embodiments, $R_1$ is an alkylthioalkyl group having 2-4 sulfur atoms and 4-11 carbon atoms. In specific embodiments, $R_1$ is a group having formula: -[—$(CH_2)_n$—S—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—S—$]_p$—$R_{10}$, where n is 2 or 3, p is 2-4 and $R_{10}$ is a C1-C3 alkyl group. In specific embodiments, $R_1$ is —$CH_2$—$CH_2$—S—$CH_2$—$CH_2$—S—$R_{10}$, where $R_{10}$ is C1-C3 alkyl. In specific embodiments, $R_1$ is —C—S—$CH_2$—S—$CH_2$—$CH_2$—S—$CH_2$—$CH_2$—$CH_3$.

In specific embodiments, compounds of the invention are those of formula VII:

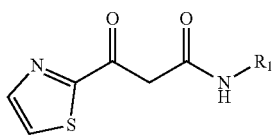

where $R_1$ is as defined for formula I, or any embodiments thereof. In specific embodiments, $R_1$ is an alkyl having 9-12 carbon atoms. In specific embodiments, $R_1$ is an alkenyl having 5-12 carbon atoms. In specific embodiments, $R_1$ is an alkenyl having 9-12 carbon atoms. In specific embodiments, $R_1$ is an unsubstituted straight-chain or branched alkyl group having 3-16 carbon atoms wherein one or more non-adjacent —$CH_2$— moieties are replaced with —O—. In embodiments, $R_1$ is an unsubstituted straight-chain or branched alkyl group having 3-16 carbon atoms wherein one or more non-adjacent —$CH_2$— moieties are replaced with —S—. In specific embodiments, $R_1$ is an alkoxyalkyl group having 1-4 oxygen atoms and 2-18 carbon atoms. In specific embodiments, $R_1$ is an alkoxyalkyl group having 1-4 oxygen atoms and 4-11 carbon atoms. In specific embodiments, $R_1$ is an alkoxyalkyl group having 2-4 oxygen atoms and 3-18 carbon atoms. In specific embodiments, $R_1$ is an alkoxyalkyl group having 2-4 oxygen atoms and 4-11 carbon atoms. In specific embodiments, $R_1$ is a group having formula: -[—$(CH_2)_n$—O—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—O—$]_p$—$R_{10}$, where n is 2 or 3, p is 2-4 and $R_{10}$ is a C1-C3 alkyl group. In specific embodiments, $R_1$ is —$CH_2$—$CH_2$—O—$CH_2$—$CH_2$—O—$R_{10}$, where $R_{10}$ is C1-C3 alkyl. In specific embodiments, $R_1$ is —$CH_2$—$CH_2$—O—$CH_2$—$CH_2$—O—$CH_2$—$CH_2$—$CH_3$. In specific embodiments, $R_1$ is an alkylthioalkyl group having 1-4 sulfur atoms and 2-18 carbon atoms. In specific embodiments, $R_1$ is an alkylthioalkyl group having 1-4 sulfur atoms and 4-11 carbon atoms. In specific embodiments, $R_1$ is an alkylthioalkyl group having 2-4 sulfur atoms and 3-18 carbon atoms. In specific embodiments, $R_1$ is an alkylthioalkyl group having 2-4 sulfur atoms and 4-11 carbon atoms. In specific embodiments, $R_1$ is a group having formula: -[—$(CH_2)_n$—S—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—S—$]_p$—$R_{10}$, where n is 2 or 3, p is 2-4 and $R_{10}$ is a C1-C3 alkyl group. In specific embodiments, $R_1$ is —$CH_2$—$CH_2$—S—$CH_2$—$CH_2$—S—$R_{10}$, where $R_{10}$ is C1-C3 alkyl. In specific embodiments, $R_1$ is —C—S—$CH_2$—S—$CH_2$—$CH_2$—S—$CH_2$—$CH_2$—$CH_3$.

In specific embodiments, compounds of the invention are those of formula VIII:

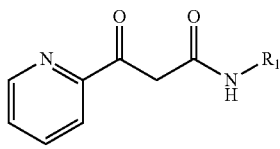

where $R_1$ is as defined for formula I, or any embodiments thereof. In specific embodiments, $R_1$ is an alkyl having 9-12 carbon atoms. In specific embodiments, $R_1$ is an alkenyl having 5-12 carbon atoms. In specific embodiments, $R_1$ is an alkenyl having 9-12 carbon atoms. In specific embodiments, $R_1$ is an unsubstituted straight-chain or branched alkyl group having 3-16 carbon atoms wherein one or more non-adjacent —$CH_2$— moieties are replaced with —O—. In embodiments, $R_1$ is an unsubstituted straight-chain or branched alkyl group having 3-16 carbon atoms wherein one or more non-adjacent —$CH_2$— moieties are replaced with —S—. In specific embodiments, $R_1$ is an alkoxyalkyl group having 1-4 oxygen atoms and 2-18 carbon atoms. In specific embodiments, $R_1$ is an alkoxyalkyl group having 1-4 oxygen atoms and 4-11 carbon atoms. In specific embodiments, $R_1$ is an alkoxyalkyl group having 2-4 oxygen atoms and 3-18 carbon atoms. In specific embodiments, $R_1$ is an alkoxyalkyl group having 2-4 oxygen atoms and 4-11 carbon atoms. In specific embodiments, $R_1$ is a group having formula: -[—$(CH_2)_n$—O—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—O—$]_p$—$R_{10}$, where n is 2 or 3, p is 2-4 and $R_{10}$ is a C1-C3 alkyl group. In specific embodiments, $R_1$ is —$CH_2$—$CH_2$—O—$CH_2$—$CH_2$—O—$R_{10}$, where $R_{10}$ is C1-C3 alkyl. In specific embodiments, $R_1$ is —$CH_2$—$CH_2$—O—$CH_2$—$CH_2$—O—$CH_2$—$CH_2$—$CH_3$. In specific embodiments, $R_1$ is an alkylthioalkyl group having 1-4 sulfur atoms and 2-18 carbon atoms. In specific embodiments, $R_1$ is an alkylthioalkyl group having 1-4 sulfur atoms and 4-11 carbon atoms. In specific embodiments, $R_1$ is an alkylthioalkyl group having 2-4 sulfur atoms and 3-18 carbon atoms. In specific embodiments, $R_1$ is an alkylthioalkyl group having 2-4 sulfur atoms and 4-11 carbon atoms. In specific embodiments, $R_1$ is a group having formula: -[—$(CH_2)_n$—S—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—S—$]_p$—$R_{10}$, where n is 2 or 3, p is 2-4 and $R_{10}$ is a C1-C3 alkyl group. In specific embodiments, $R_1$ is —$CH_2$—$CH_2$—S—$CH_2$—$CH_2$—S—$R_{10}$, where $R_{10}$ is C1-C3 alkyl. In specific embodiments, $R_1$ is —$CH_2$—$CH_2$—S—$CH_2$—$CH_2$—S—$CH_2$—$CH_2$—$CH_3$.

In specific embodiments, compounds of the invention are those of formula IX:

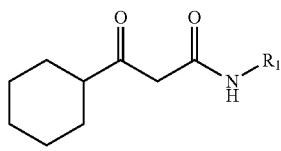

where $R_1$ is as defined for formula I, or any embodiments thereof. In specific embodiments, $R_1$ is an alkyl having 9-12 carbon atoms. In specific embodiments, $R_1$ is an alkenyl having 5-12 carbon atoms. In specific embodiments, $R_1$ is an alkenyl having 9-12 carbon atoms. In specific embodiments, $R_1$ is an unsubstituted straight-chain or branched alkyl group having 3-16 carbon atoms wherein one or more non-adjacent —$CH_2$— moieties are replaced with —O—. In embodiments, $R_1$ is an unsubstituted straight-chain or branched alkyl group having 3-16 carbon atoms wherein one or more non-adjacent —$CH_2$— moieties are replaced with —S—. In specific embodiments, $R_1$ is an alkoxyalkyl group having 1-4 oxygen atoms and 2-18 carbon atoms. In specific embodiments, $R_1$ is an alkoxyalkyl group having 1-4 oxygen atoms and 4-11 carbon atoms. In specific embodiments, $R_1$ is an alkoxyalkyl group having 2-4 oxygen atoms and 3-18 carbon atoms. In specific embodiments, $R_1$ is an alkoxyalkyl group having 2-4 oxygen atoms and 4-11 carbon atoms. In specific embodiments, $R_1$ is a group having formula: -[—$(CH_2)_n$—O—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—O—$]_p$—$R_{10}$, where n is 2 or 3, p is 2-4 and $R_{10}$ is a C1-C3 alkyl group. In specific embodiments, $R_1$ is —$CH_2$—$CH_2$—O—$CH_2$—$CH_2$—O—$R_{10}$, where $R_{10}$ is C1-C3 alkyl. In specific embodiments, $R_1$ is —$CH_2$—$CH_2$—O—$CH_2$—$CH_2$—O—$CH_2$—$CH_2$—$CH_3$. In specific embodiments, $R_1$ is an alkylthioalkyl group having 1-4 sulfur atoms and 2-18 carbon atoms. In specific embodiments, $R_1$ is an alkylthioalkyl group having 1-4 sulfur atoms and 4-11 carbon atoms. In specific embodiments, $R_1$ is an alkylthioalkyl group having 2-4 sulfur atoms and 3-18 carbon atoms. In specific embodiments, $R_1$ is an alkylthioalkyl group having 2-4 sulfur atoms and 4-11 carbon atoms. In specific embodiments, $R_1$ is a group having formula: -[—$(CH_2)_n$—S—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—S—$]_p$—$R_{10}$, where n is 2 or 3, p is 2-4 and $R_{10}$ is a C1-C3 alkyl group. In specific embodiments, $R_1$ is —$CH_2$—$CH_2$—S—$CH_2$—$CH_2$—S—$R_{10}$, where $R_{10}$ is C1-C3 alkyl. In specific embodiments, $R_1$ is —C—S—$CH_2$—S—$CH_2$—$CH_2$—S—$CH_2$—$CH_2$—$CH_3$.

In specific embodiments, compounds of the invention are those of formula X:

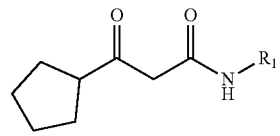

where $R_1$ is as defined for formula I, or any embodiments thereof. In specific embodiments, $R_1$ is an alkyl having 9-12 carbon atoms. In specific embodiments, $R_1$ is an alkenyl having 5-12 carbon atoms. In specific embodiments, $R_1$ is an alkenyl having 9-12 carbon atoms. In specific embodiments, $R_1$ is an unsubstituted straight-chain or branched alkyl group having 3-16 carbon atoms wherein one or more non-adjacent —$CH_2$— moieties are replaced with —O—. In embodiments, $R_1$ is an unsubstituted straight-chain or branched alkyl group having 3-16 carbon atoms wherein one or more non-adjacent —$CH_2$— moieties are replaced with —S—. In specific embodiments, $R_1$ is an alkoxyalkyl group having 1-4 oxygen atoms and 2-18 carbon atoms. In specific embodiments, $R_1$ is an alkoxyalkyl group having 1-4 oxygen atoms and 4-11 carbon atoms. In specific embodiments, $R_1$ is an alkoxyalkyl group having 2-4 oxygen atoms and 3-18 carbon atoms. In specific embodiments, $R_1$ is an alkoxyalkyl group having 2-4 oxygen atoms and 4-11 carbon atoms. In specific embodiments, $R_1$ is a group having formula: -[—$(CH_2)_n$—O—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—O—$]_p$—$R_{10}$, where n is 2 or 3, p is 2-4 and $R_{10}$ is a C1-C3 alkyl group. In specific embodiments, $R_1$ is —$CH_2$—$CH_2$—O—$CH_2$—$CH_2$—O—$R_{10}$, where $R_{10}$ is C1-C3 alkyl. In specific embodiments, $R_1$ is —$CH_2$—$CH_2$—O—$CH_2$—$CH_2$—O—$CH_2$—$CH_2$—$CH_3$. In specific embodiments, $R_1$ is an alkylthioalkyl group having 1-4 sulfur atoms and 2-18 carbon atoms. In specific embodiments, $R_1$ is an alkylthioalkyl group having 1-4 sulfur atoms and 4-11 carbon atoms. In specific embodiments, $R_1$ is an alkylthioalkyl group having 2-4 sulfur atoms and 3-18 carbon atoms. In specific embodiments, $R_1$ is an alkylthioalkyl group having 2-4 sulfur atoms and 4-11 carbon atoms. In specific embodiments, $R_1$ is a group having formula: -[—$(CH_2)_n$—S—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—S—$]_p$—$R_{10}$, where n is 2 or 3, p is 2-4 and $R_{10}$ is a C1-C3 alkyl group. In specific embodiments, $R_1$ is —$CH_2$—$CH_2$—S—$CH_2$—$CH_2$—S—$R_{10}$, where $R_{10}$ is C1-C3 alkyl. In specific embodiments, $R_1$ is —$CH_2$—$CH_2$—S—$CH_2$—$CH_2$—S—$CH_2$—$CH_2$—$CH_3$.

In specific embodiments, compounds of the invention are those of formula XI:

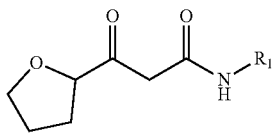

where $R_1$ is as defined for formula I, or any embodiments thereof. In specific embodiments, $R_1$ is an alkyl having 9-12 carbon atoms. In specific embodiments, $R_1$ is an alkenyl having 5-12 carbon atoms. In specific embodiments, $R_1$ is an alkenyl having 9-12 carbon atoms. In specific embodiments, $R_1$ is an unsubstituted straight-chain or branched alkyl group having 3-16 carbon atoms wherein one or more non-adjacent —$CH_2$— moieties are replaced with —O—. In embodiments, $R_1$ is an unsubstituted straight-chain or branched alkyl group having 3-16 carbon atoms wherein one or more non-adjacent —$CH_2$— moieties are replaced with —S—. In specific embodiments, $R_1$ is an alkoxyalkyl group having 1-4 oxygen atoms and 2-18 carbon atoms. In specific embodiments, $R_1$ is an alkoxyalkyl group having 1-4 oxygen atoms and 4-11 carbon atoms. In specific embodiments, $R_1$ is an alkoxyalkyl group having 2-4 oxygen atoms and 3-18 carbon atoms. In specific embodiments, $R_1$ is an alkoxyalkyl group having 2-4 oxygen atoms and 4-11 carbon atoms. In specific embodiments, $R_1$ is a group having formula: -[—$(CH_2)_n$—O—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—O—$]_p$—$R_{10}$, where n is 2 or 3, p is 2-4 and $R_{10}$ is a C1-C3 alkyl group. In specific embodiments, $R_1$ is —$CH_2$—$CH_2$—O—$CH_2$—$CH_2$—O—$R_{10}$, where $R_{10}$ is C1-C3 alkyl. In specific embodiments, $R_1$ is —$CH_2$—$CH_2$—O—$CH_2$—$CH_2$—O—$CH_2$—$CH_2$—$CH_3$. In specific embodiments, $R_1$ is an alkylthioalkyl group having 1-4 sulfur atoms and 2-18 carbon atoms. In specific embodiments, $R_1$ is an alkylthioalkyl group having 1-4 sulfur atoms and 4-11 carbon atoms. In specific embodiments, $R_1$ is an alkylthioalkyl group having 2-4 sulfur atoms and 3-18 carbon atoms. In specific embodiments, $R_1$ is an alkylthioalkyl group having 2-4 sulfur atoms and 4-11 carbon atoms. In specific embodiments, $R_1$ is a group having formula: -[—$(CH_2)_n$—S—$]_p$—$R_{10}$, where n is 1, 2 or 3, p is 1-4 and $R_{10}$ is a C1-C6 alkyl group. In specific embodiments, $R_1$ is a group having formula: -[—$(CH_2)_n$—S—$]_p$—$R_{10}$, where n is 2 or 3, p is 2-4 and $R_{10}$ is a C1-C3 alkyl group. In specific embodiments, $R_1$ is —$CH_2$—$CH_2$—S—$CH_2$—$CH_2$—S—$R_{10}$, where $R_{10}$ is C1-C3 alkyl. In specific embodiments, $R_1$ is —C—S—$CH_2$—S—$CH_2$—$CH_2$—S—$CH_2$—$CH_2$—$CH_3$.

In specific embodiments, the invention provides compound 21. In specific embodiments, the invention provides compound 25. In specific embodiments, the invention provides compound 26. In specific embodiments, the invention provides compound 28. In specific embodiments, the invention provides compound 29. In specific embodiments, the invention provides compound 30. In specific embodiments, the invention provides compound 31. In specific embodiments, the invention provides compound 33. In specific embodiments, the invention provides compound 35. In specific embodiments, the invention provides compound 36. In specific embodiments, the invention provides compound 38. In specific embodiments, the invention provides compound 40.

In an embodiment, the invention provides a compound of formula XII:

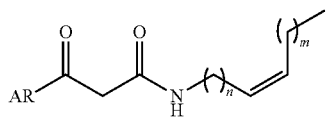

where AR is as defined in formula I, or any embodiments thereof, wherein n+m is 5-16 or 6-16 or 7-16 and n is 1-15 and m is 1-15. In a specific embodiment, n is 3-9 and m is 3-9. In a specific embodiment, n+m is 9-12. In a specific embodiment, n is 3-5 and n+m is 9-12.

The invention provides compounds of formulas herein which exhibit $IC_{50}$ on a given Gram-negative bacterium of 3 micromolar or less. The invention provides compounds of formulas herein which exhibit $IC_{50}$ on a given Gram-negative bacterium of 2 micromolar or less. The invention provides compounds of formulas herein which exhibit $IC_{50}$ on a given Gram-negative bacterium of 1 micromolar or less. The invention provides compounds of formulas herein which exhibit $IC_{50}$ on a given Gram-negative bacterium of less than 1 micromolar. The invention provides compounds of formulas herein which exhibit $IC_{50}$ on a given Gram-negative bacterium of 0.8 micromolar or less.

The invention provides compounds of formula II which function for regulation of quorum sensing in Gram-negative bacteria, particularly *Pseudomonas* and more particularly in *P. aeruginosa*:

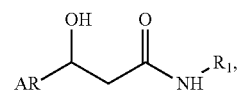

where $R_1$ is any of the groups defined above for any of formulas III, IVA, IVB, V, VI, VII, VIII, IX, X, XI or XII or any embodiments thereof and AR is selected from: optionally substituted phenyl, optionally substituted heterocyclic, optionally substituted cycloalkyl, and optionally substituted cycloalkenyl.

In specific embodiments, optional substitution of phenyl, heterocyclic, cycloalkyl, and cycloalkenyl groups includes substitution with a hydroxyl, a C1-C3 alkoxy or a halogen.

More specifically, AR is selected from unsubstituted phenyl or phenyl substituted with 1-5 non-hydrogen substituents. In an embodiment, AR is a phenyl ring substituted with one or more halogen, hydroxyl, alkoxy or $NH_2$ groups. In an embodiment, AR is a phenyl ring substituted with one to three hydroxyl or halogen. In an embodiment, AR is a phenyl ring substituted with one or two hydroxyl or halogen. In an embodiment, AR is a phenyl ring substituted with one hydroxyl or halogen. In an embodiment, AR is a phenyl ring substituted with one hydroxyl group. In an embodiment, AR is a phenyl ring substituted with a hydroxyl in the meta ring position. In an embodiment, AR is a phenyl ring substituted with a hydroxyl in the ortho ring position. In an embodiment, AR is a phenyl ring substituted with one halogen, particularly a fluorine. In an embodiment, AR is a phenyl ring substituted with a halogen, particularly a fluorine, in the meta ring position. In an embodiment, AR is a phenyl ring substituted with a halogen, particularly a fluorine, in the ortho ring position.

In an embodiment, AR is an unsubstituted 5- or 6-member ring cycloakyl group. In an embodiment, AR is an unsubstituted 5- or 6-member ring cycloakenyl group. In an embodiment, AR is an unsubstituted 5- or 6-member ring cycloakenyl group having a single double bond in the ring.

In an embodiment, AR is an unsubstituted heteroaryl group.

In an embodiment, AR is an unsubstituted furyl group. In an embodiment, AR is an unsubstituted fur-2-yl group. In an embodiment, AR is n unsubstituted fur-3-yl group. In an embodiment, AR is an unsubstituted thiophenyl group. In an embodiment, AR is an unsubstituted thiophen-2-yl group. In an embodiment, AR is an unsubstituted thiophen-3-yl group.

In embodiments, the invention provides compounds of formula XX or XXI:

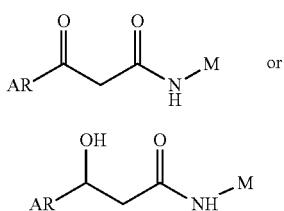

where AR is as defined in formula I or any embodiments thereof and
M is an alkyl group having 1-3 carbon atoms that is substituted at the distal (also called the omega) position with an optionally substituted phenyl group, a cycloalkyl, a cycloalkenyl group, or a branched alkyl group having 4-12 carbon atoms with a branch at the 1-position in the group. Specific M groups include:

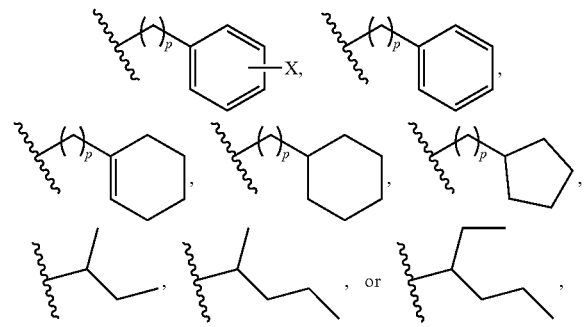

where p is 1, 2 or 3 and preferably 1 or 2; and X is a substituent for a phenyl group as described in formulas III, IVA or IVB.

The invention provides compounds of formulas herein which exhibit Maximum % Inhibition on a given Gram-negative bacterium of 80% or more. The invention provides compounds of formulas herein which exhibit Maximum % Inhibition on a given Gram-negative bacterium of 85% or more. The invention provides compounds of formulas herein which exhibit Maximum % Inhibition on a given Gram-negative bacterium of 87% or more. The invention provided compounds of formulas herein which exhibit Maximum % Inhibition on a given Gram-negative bacterium of 90% or more. The invention provided compounds of formulas herein which exhibit Maximum % Inhibition on a given Gram-negative bacterium of 95% or more. The invention provided compounds of formulas herein which exhibit Maximum % Inhibition on a given Gram-negative bacterium of 100%.

The invention relates to a method for inhibiting quorum sensing in vivo or in vitro of a Gram-negative bacterium employing contacting the bacterium or an environment containing the bacterium with a modulator of LasR. In specific embodiments, the small molecule modulators of the QS systems herein exclude the native activators of the QS system. In a specific embodiment, inhibiting quorum sensing inhibits virulence. In a specific embodiment, inhibiting quorum sensing inhibits biofilm formation.

In specific embodiments, the Gram-negative bacterium is of the family Pseudomonadacae. In specific embodiments, the Gram-negative bacterium is a species of the genus *Pseudomonas*. In specific embodiments, the Gram-negative bacterium is a species of the genus *Pseudomonas* having a quorum sensing system. In specific embodiments, the Gram-negative bacterium is a species of the genus *Pseudomonas* in which biofilm formation is regulated in quorum sensing. In specific embodiments, the Gram-negative bacterium is a species of the genus *Pseudomonas* that is pathogenic. In specific embodiments, the Gram-negative bacterium is *Pseudomonas aeruginosa*. In specific embodiments, the *Pseudomonas* species is *P. putida*. In specific embodiments, the *Pseudomonas* species is *P. syringae*. In specific embodiments, the Gram-negative bacterium is a species of the genus *Burkholderia*. In specific embodiments, the species of *Burkholderia* is *B. cepacia, B. pseudomallei*, or *B. mallei*.

The invention also relates to a method for inhibiting quorum sensing in vivo or in vitro of a Gram-negative bacterium which has a LasR QS system employing contacting the bacterium or an environment containing the bacterium with a small molecule modulators of LasR as disclosed herein. In specific embodiments, the small molecule modulators of LasR exclude the native activators of QS systems. The native activators of various QS systems of Gram-negative bacteria are known in the art. In a specific embodiment, inhibiting quorum sensing inhibits virulence. In a specific embodiment, inhibiting quorum sensing inhibits biofilm formation in the bacterium. In a specific embodiment, LasR of the QS systems of the Gram-negative bacterium is mediated in nature by an N-acylhomoserine lactone signal molecule (i.e., the native activator of the QS system is an N-acylhomoserine lactone) and for example in *P. aeruginosa* the native activator is OdDHL (FIG. 1). In specific embodiments, the Gram-negative bacterium is of the family Pseudomonadacae. In specific embodiments, the Gram-negative bacterium is a species of the genus *Pseudomonas*. In specific embodiments, the Gram-negative bacterium is a pathogenic species of the genus *Pseudomonas*. In specific embodiments, the Gram-negative bacterium is *Pseudomonas aeruginosa*. In specific embodiments, the *Pseudomonas* species is *P. putida*, or *P. syringae*. In specific embodiments, the Gram-negative bacterium is a species of the genus *Burkholderia*. In specific embodiments, the species of *Burkholderia* is *B. cepacia, B. pseudomallei*, or *B. mallei*.

The invention provides a method for treatment of an infection of a Gram-negative bacterium by inhibiting virulence in the bacterium employing one or more compounds of the invention. In specific embodiments, the method employs one or more compounds of any one of the formulas herein.

The invention also provided compositions comprising one or more LasR modulators of the invention, specifically those of any one of the formulas herein, in combination with a compound which modulates a different QS system of the bacterium (e.g., a modulator of RhlR or PqsR). In a specific embodiment, the method comprises the step of administering, to an individual in need of treatment for such infection, one or more compounds of the invention (e.g., of formulas I or II) in a combination with one or more small molecule antagonists of a QS system other than LasR controlling virulence in the bacterium. In a specific embodiment, the composition is a combination of a LasR modulator of this invention and a modulator of RhlR or PqsR. In a specific embodiment, the composition is a combination of a LasR antagonist of this invention and an antagonist of RhlR or PqsR.

A variety of small molecule antagonists of QS systems are known in the art. See for example U.S. Pat. Nos. 7,910,622; 8,815,943; 9,796,694; 8,624,063 and 9,758,472 and US published application 20170231962; Moore et al. 2014 and supporting information thereof; Eibergen et al. 2015 and supporting information thereof; Moore et al. 2015 and supporting information thereof; O'Reilly et al. 2016 and supporting information thereof; Welsh et al. 2015 and supporting information thereof are each incorporated by reference herein at least for structures of QS system modulators, including antagonist and agonists, for additional synthetic methods or details of methods applicable to the synthesis of compounds herein, and additional methods or details of methods of assessment of modulation of QS. Additionally, Moore et al. 2015 discusses details of active efflux on QS modulators.

In specific embodiments, the invention provides a method for treatment of an infection in an animal including a mammal and including a human of a Gram-negative bacterium by inhibiting virulence in the bacterium employing a combination of a LasR modulator of this invention with one or more small molecule modulators of a different QS system of the bacterium. In another specific embodiment, the infection is an infection of a combination of bacteria at least one of which has multiple QS systems. In another specific embodiment, the infection is an infection of a combination of species of bacteria of the genus *Pseudomonas* and *Burkholderia*. In a specific embodiment, the infection is an infection of the bacterium *P. aeruginosa*. In another specific embodiment, the infection is an infection of a combination of bacteria, including *P. aeruginosa*. In another specific embodiment, the infection is an infection of a combination of *P. aeruginosa* and *Burkholderia cepacia*. In specific embodiments, the infection is an infection of the lungs. In an embodiment, the infection is an infection of a burn wound. In an embodiment, the infection is an infection in an immune-compromised individual. In an embodiment, the infection is an infection in an individual with cystic fibrosis. In an embodiment, the infection is an infection in an individual with HIV.

The invention in addition provides a virulence inhibiting composition comprising a LasR antagonist of the invention and one or more small molecule QS modulators, each of which modulates a different QS system of a selected Gram-negative bacterium. In a specific embodiment, the virulence inhibiting composition is a pharmaceutically acceptable composition. In a specific embodiment, the virulence inhibiting composition comprises the LasR modulator of the invention and one or more small molecule QS modulators as active ingredients in combination with a pharmaceutically acceptable carrier. In a specific embodiment, the virulence inhibiting composition comprises the LasR antagonist of the invention and one or more small molecule QS antagonists as active ingredients in combination with a pharmaceutically acceptable carrier. In a specific embodiment, the virulence inhibiting composition comprises the LasR antagonist of the invention and one or more small molecule RhlR or Pqs antagonists as active ingredients in combination with a pharmaceutically acceptable carrier.

In another aspect, the invention relates to certain combinations of LasR modulators of this invention in combination with modulators of RhlR and/or Pqs which exhibit improved inhibition of virulence in comparison to the respective individual modulators. In specific embodiments, certain combinations of modulators exhibit such improved inhibition in nutritionally depleted (with respect to the bacterium) environments. In specific embodiments, certain combinations of modulators exhibit such improved inhibition in environments depleted in phosphate. In specific embodiments, certain combinations of modulators exhibit such improved inhibition in environments depleted in iron.

Combination of QS modulators with LasR modulators herein includes chemically different modulators wherein the modulators affect either the Rhl or Pqs QS systems. In some cases, a given modulator in a combination may affect more than one QS system. In the case where a given modulator affects more than one QS system, the modulator will be designated based on the QS system for which it exhibits the highest level of effect. The effect of a given modulator on a given QS system may depend upon the level of nutrients, the carbon source or other components or conditions (e.g., pH) of the environment of the bacterium, where such environment can, for example, be an in vivo environment infected by the bacterium. Preferably, the combination contains chemically different modulators of LasR with one of a RhlR modulator or a Pqs modulator. In specific embodiments, the combination of modulators is a combination of one or more antagonist of LasR of the invention with one or more antagonist of RhlR. In specific embodiments, the combination of modulators is a combination of one or more antagonists of LasR with one or more antagonist of PqsR.

The invention also relates to a method for inhibiting quorum sensing in vivo or in vitro of a Gram-negative bacterium which has a plurality of QS systems employing contacting the bacterium or an environment containing the bacterium with a combination of small molecule modulators of two or more of the QS systems wherein one modulator is a LasR modulator of the invention. In specific embodiments, the small molecule modulators of the QS systems exclude the native activators of the OS systems. In a specific embodiment, inhibiting quorum sensing inhibits virulence and the plurality of QS systems together control virulence of the bacterium. In a specific embodiment, inhibiting quorum sensing inhibits biofilm formation and the plurality of QS systems modulate biofilm formation in the bacterium. In a specific embodiment, the QS systems of the Gram-negative bacterium include at least one QS system which is mediated in nature by an N-acylhomoserine lactone signal molecule (i.e., the native activator of the QS system is an N-acylhomoserine lactone). In a specific embodiment, activity of the modulators of one or more of the multiple QS systems of the bacterium exhibits a dependence upon the environment of the bacterium. In specific embodiments, the activity of the modulators of one or more of the multiple QS systems of the bacterium exhibits a dependence upon the levels of nutrients in the environment of the bacterium. In specific embodiments, the activity of the modulators of one or more of the multiple QS systems of the bacterium exhibits a dependence upon the levels of phosphate in the environment of the bacterium. In specific embodiments, the activity of the modulators of one or more of the multiple QS systems of the bacterium exhibits a dependence upon the levels of iron in the environment of the bacterium. In specific embodiments, the Gram-negative bacterium is of the family Pseudomonadacae. In specific embodiments, the Gram-negative bacterium is a species of the genus *Pseudomonas*. In specific embodiments, the Gram-negative bacterium is *Pseudomonas aeruginosa*. In specific embodiments, the *Pseudomonas* species is *P. putida*, or *P. syringae*. In specific embodiments, the Gram-negative bacterium is a species of the genus *Burkholderia*. In specific embodiments, the species of *Burkholderia* is *B. cepacia*, *B. pseudomallei*, or *B. mallei*.

The invention provides a method for treatment of an infection of a Gram-negative bacterium by inhibiting virulence in the bacterium employing a combination of two or modulators each of which modulates a different QS system of the bacterium wherein one of the modulators is a modulator of LasR of the invention. In a specific embodiment, the method comprises the step of administering, to an individual in need of treatment for such infection, the combination of two or more small molecule antagonists of a QS system controlling virulence in the bacterium. More specifically, the two or more antagonists include one or more antagonists of one QS system of the bacterium and one or more antagonists of a second QS system of the bacterium. In specific embodiments, the Gram-negative bacterium is of the species *Pseudomonas*. In specific embodiments, the Gram-negative bacterium is *Pseudomonas aeruginosa*.

Further aspects and embodiments of the invention will be apparent to one of ordinary skill in the art on consideration of the drawings and examples.

Bacteria can have multiple quorum sensing systems which are distinct. Distinct quorum sensing systems are defined by having distinct proteins involved in regulation of quorum sensing and distinct molecules which activate a given quorum sensing system. A compound which is a modulator of a selected quorum sensing system in a given bacterium (e.g., LasR, RhlR or PqsR in *Pseudomonas*) may exhibit some level of activity as a modulator of a different quorum sensing system in that bacterium. For example, a given modulator, particularly a synthetic non-native small molecule may acts as an inhibitor of LasR and an agonist of RhlR. More specifically, a compound which is an inhibitor of one quorum sensing system may also inhibit other quorum sensing systems in the same bacterium. The relative amount of inhibition (or activation) that a given compound exhibits for each quorum sensing system in a bacterium can be assessed, for example, as demonstrated in Welsh et al. (2015), Moore et al. 2015 and Eibergen et al. (2015) by determining the relative levels of antagonism or agonism exhibited by a given compound with respect to different quorum sensing systems present in a bacterium. The text and supplemental information for each of these references is incorporated by reference herein at least for assay methods for determining relative levels of antagonism and agonism of a given compound for a given quorum sensing system.

The terms "inhibitor" and "antagonist" are used interchangeably herein. The terms "activator" and "agonist" are used interchangeably herein.

The term "small molecule" refers to compounds having a molecular weight of 900 daltons or less and more preferably to those having molecular weight of 500 daltons or less. The maximum upper limit relates at least in part to allow for rapid diffusion across cell membranes and to facilitate oral bioavailability.

In specific embodiments, inhibitors of LasR of the invention, RhlR inhibitors and PqsR inhibitors are employed in combinations. U.S. provisional application 62/294,921, filed Feb. 12, 2016, and U.S. application Ser. No. 15/431,295, filed Feb. 13, 2017, are also each incorporated by reference herein for descriptions of exemplary LasR and PqsR modulators which may be used in combination with RhlR modulators of this invention.

The Rhl and Pqs systems work in tandem to drive virulence factor production in nutrient limiting conditions, while Las is only a minor contributor under such nutrient limiting conditions. LasR inhibitors display reduced activity in low iron and phosphate environments, and as a result, cocktails (mixtures) of RhlR and PqsR inhibitors can attenuate virulence in a broad range of conditions where Las antagonists are inactive. The activity trends uncovered herein are also predictive of compound activity in infection relevant environments, including the CF airway, which are nutrient limiting condition for the bacterium. Thus, the present work indicates unique roles for the *P. aeruginosa* QS systems in tailoring virulence factor production to the environment, and provides novel insights into pathways that, with further development, could potentially be targeted to fight this pathogen.

The terms "nutrient limiting" or "nutrient depleted" refer to bacterial environments that are limited or depleted with respect to the nutritional needs of a given bacterium such that growth of the bacterium is limited under such conditions. Certain quorum sensing systems are sensitive to such "nutrient limiting" or "nutrient depleted" condition such that the systems are modulated in response to such limitation or depletion. The present work investigates quorum sensing inhibition and activation and the interaction of quorum sensing systems in such depleted or limited environments. Such limited or depleted environments ca, for example, be bacterial infection sites, such as the CF airway, a burn or other wound site, the intestine or other in vivo site after surgery. Nutrient limitation or depletion in an in vivo environment can affect virulence of the bacteria in that environment and can affect the extent or virulence of a given infection. The term depleted and limited for a given nutrient are used relative to the level of that nutrient that supports unlimited growth of the bacterium or that is sufficiently high that a given quorum sensing system is not affected by the level of nutrient present. The amount of a given nutrient that results in such growth limitation or quorum sensing modulation will depend on the bacterium and may also depend upon other nutrients in the environment. One of ordinary skill in the art can determine if a given environment is depleted or limiting for a given bacterium without resort to undue experimentation using methods that are known in the art.

The LasR modulators of this invention can be employed in any in vivo or in vitro application for inhibition of virulence of Gram-negative bacteria, alone or in combination with other QS modulators. Contact or administration of the modulators or combinations with other QS modulators can be achieved by various means known in the art by combined or separate contact or combined or separate administration of component compounds of the combinations. Each component of a combination can be formulated separately or the combination of components can be formulated together.

Geske et al. 2007a, Geske et al. 2007b, Geske et al. 2008a and Geske et al. 2008b are each incorporated by reference herein in its entirety to provide comparisons of QS activity as agonists or antagonists of compounds therein to compounds herein.

The invention also provides a method for treating infections of Gram-negative bacteria in an individual in need of such treatment wherein a therapeutically effective amount of one or more LasR modulators of this invention of formulas I, II, IIIA, IIIB, or IV-X herein or a pharmaceutically acceptable salt thereof are administered to said individual. The modulators are in an embodiments antagonists.

The invention also provides therapeutic compositions for treating infections of Gram-negative bacteria comprising a therapeutically effective amount of a LasR modulator of this invention of formulas herein or a pharmaceutically acceptable salt of the compounds herein and a pharmaceutically acceptable carrier. In a specific embodiment, such therapeutic compositions comprise at least two quorum sensing compounds of formulas herein or a pharmaceutically acceptable salt thereof. The modulators are in an embodiments antagonists.

The invention also provides methods for making a medicament for treatment of a bacterial infection, particularly of a Gram-negative bacterium, and more particularly of a strain of *Pseudomonas* or a strain of *Burkholderia*, in which one or more LasR modulators of the invention, particularly which are which are quorum sensing inhibitors.

In an embodiment, combinations of modulators, including inhibitors of different quorum sensing systems in the bacterium are combined to provide for enhanced inhibition.

Such medicaments can further include a pharmaceutically acceptable carrier or excipient as are known in the art.

In an additional embodiment, the invention provides one or more LasR modulators or combinations thereof with other QS modulators and methods employing the same for reducing bacterial virulence and increasing susceptibility of quorum sensing bacterial to biocides and/or antibiotics.

For methods of inhibiting virulence or treating infections herein, one or more compounds (or salts thereof) are administered to a patient or applied to an environment in an amount effective for inhibition of a given quorum sensing system. Generally an effective amount will be dependent upon the bacterium and the environment of the bacterium. In an embodiment for inhibiting a given bacterium in a given environment, the effective amount of a given compound is equal to or greater than the $IC_{50}$ of that compound for a given quorum sensing system. In an embodiment for administration to a mammal, the effective amount of a given compound for inhibition ranges from the $IC_{50}$ or $EC_{50}$ of the compound for inhibition to less than the toxicity level of the compound for mammalian cells. As defined herein, "contacting" means that a compound of the present invention is provided such that it is capable of making physical contact with another element, such as a microorganism, a microbial culture, a biofilm, or a substrate or other environment of a bacterium. In another embodiment, the term "contacting" means that a compound of the present invention is introduced into an individual receiving treatment, and the compound is allowed to come in contact in vivo. The term "administering" is also used for providing a compound or pharmaceutical composition to an individual (or subject) in need of treatment. Various administration methods can be employed as will be appreciated by one of ordinary skill in the art.

The term "effective amount" is used generically herein to refer to the amount of a given compound or in case of a combination of compounds the combined amount of mixed components that provides a measurable effect for a listed function. In certain aspects of the invention, the effective amount is for treating an infection (see however, the more specific therapeutically effective amount below). In certain embodiments, the effective amount is for inhibition of virulence. In certain embodiments, the effective amount is for inhibition growth of a bacterium. One or more compounds herein or combinations thereof with other QS modulators, in certain embodiments, can inhibit growth or establishment of a biofilm. One or more compounds herein or combinations thereof with other QS modulators, in certain embodiments, can disperse an already formed biofilm.

For example, in certain aspects of the invention, a compound of the invention is contacted with an element (a substrate, a surface a tool an instrument or the like) in order to prevent formation of or disrupt a biofilm and in this case, the effective amount or combined effective amount of the compound or compounds is that amount that shows a measurable disruption of a biofilm. The effective amount will vary dependent upon the stated function, the environment or element being contacted, the organism forming the biofilm or which is to be contacted, the state of development of the biofilm, among other conditions of the use of the compound. It will be understood by one of ordinary skill in the art, that for a given application, the effective amount can be determined by application of routine experimentation and without undue experimentation by methods that are described herein or that are known in the art.

The term "therapeutically effective amount" is used generically herein to refer to the amount of a given compound or in case of a combination (the individual amount of components or the combined amount of a mixture components when administered to the individual (including a human, or non-human animal) that provides a measureable therapeutic effect for a listed disease, disorder or condition to at least partially ameliorate a symptom of such disease, disorder or condition. The present invention provides methods of treating disorders, diseases conditions and symptoms in a human or non-human animal and particularly in a human, by administering to an individual in need of treatment or prophylaxis, a therapeutically effective amount of one or more compounds of this invention to the individual in need thereof. The result of treatment can be partially or completely alleviating, inhibiting, preventing, ameliorating and/or relieving the disorder, condition or one or more symptoms thereof. As is understood in the art, the therapeutically effective amount of a given compound will depend at least in part upon, the mode of administration, any carrier or vehicle (e.g., solution, emulsion, etc.) employed, the extent of damage and the specific individual (human or non-human) to whom the compound is to be administered (age, weight, condition, sex, etc.). The dosage requirements needed to achieve the "therapeutically effective amount" vary with the particular compositions employed, the route of administration, the severity of the symptoms presented and the particular individual being treated. Based on the results obtained in standard pharmacological test procedures, projected daily dosages of active compound can be determined as is understood in the art.

Administration is intended to encompass administration of a compound (or combination of compounds as discussed herein), pharmaceutically acceptable salt, solvate or ester thereof alone or in a pharmaceutically acceptable carrier thereof or administration of a prodrug derivative or analog of a compound of this invention which will form an equivalent amount of the active compound or substance within the body. An individual in need of treatment or prophylaxis includes those who have been diagnosed to have a given disorder or condition and to those who are suspected, for example, as a consequence of the display of certain symptoms, of having such disorders or conditions.

Compounds and combinations of compounds of this invention can be employed in unit dosage form, e.g. as tablets or capsules. In such form, the active compound or more typically a pharmaceutical composition containing the active compound is sub-divided in unit dose containing appropriate quantities of the active compound; the unit dosage forms can be packaged compositions, for example, packaged powders, vials, ampules, pre-filled syringes or sachets containing liquids. The unit dosage form can be, for example, a capsule or tablet itself, or it can be the appropriate number of any such compositions in package form.

The dosage can vary within wide limits and as is understood in the art will have to be adjusted to the individual requirements in each particular case. By way of general guidance, the daily oral dosage can vary from about 0.01 mg to 1000 mg, 0.1 mg to 100 mg, or 10 mg to 500 mg per day of a compound of formulas herein or of the corresponding amount of a pharmaceutically acceptable salt thereof. The daily dose may be administered as single dose or in divided doses and, in addition, the upper limit can also be exceeded when this is found to be indicated.

Any suitable form of administration can be employed in the methods herein. The compounds of this invention can, for example, be administered in oral dosage forms including tablets, capsules, pills, powders, granules, elixirs, tinctures, suspensions, syrups and emulsions. Oral dosage forms may include sustained release or timed release formulations. The compounds of this invention may also be administered topically, intravenously, intraperitoneally, subcutaneously, or intramuscularly, all using dosage forms well known to those of ordinary skill in the pharmaceutical arts. Topical application can include those in which the biofilm-inhibitory compound is formulated in a hydrogel or encapsulated in microspheres or nanospheres, for example.

Compounds and combinations of compounds of this invention can also be administered in intranasal form by topical use of suitable intranasal vehicles. For intranasal or intrabronchial inhalation or insulation, the compounds of this invention may be formulated into an aqueous or partially aqueous solution, which can then be utilized in the form of an aerosol. Administration includes any form of administration that is known in the art and is intended to encompass administration in any appropriate dosage form and further is intended to encompass administration of a compound, alone or in a pharmaceutically acceptable carrier. Pharmaceutical carriers are selected as is known in the art based on the chosen route of administration and standard pharmaceutical practice.

The compounds and combinations of compounds of this invention can also be administered to the eye, preferably as a topical ophthalmic formulation. The compounds and combinations of compounds of this invention can also be combined with a preservative and an appropriate vehicle such as mineral oil or liquid lanolin to provide an ophthalmic ointment. The compounds and combinations of compounds of this invention may be administered rectally or vaginally in the form of a conventional suppository. The compounds and combinations of compounds of this invention may also be administered transdermally through the use of a transdermal patch containing the active compound and a carrier that is inert to the active compound, is non-toxic to the skin, and allows delivery of the agent for systemic absorption into the blood stream via the skin.

The compounds and combinations of compounds of the invention may be administered employing an occlusive device. A variety of occlusive devices can be used to release an ingredient into the blood stream such as a semipermeable membrane covering a reservoir containing the active ingredient with or without a carrier, or a matrix containing the active ingredient. Other occlusive devices are known in the literature.

Pharmaceutical compositions and medicaments of this invention comprise one or more compounds of any of formulas I, II, IIIA, IIIB, or IV-X in combination with a pharmaceutically acceptable carrier, excipient, or diluent. Such compositions and medicaments are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety.

The invention also encompasses method for making a medicament employing a combination of a LasR modulator (preferably an antagonist) of the invention and one or more QS compounds or other antibacterial compounds which together exhibit a combined therapeutic effect.

Pharmaceutically acceptable carriers are those carriers that are compatible with the other ingredients in the formulation and are biologically acceptable. Carriers can be solid or liquid. Solid carriers can include one or more substances that can also act as flavoring agents, lubricants, solubilizers, suspending agents, fillers, glidants, compression aids, binders, tablet-disintegrating agents, or encapsulating materials. Liquid carriers can be used in preparing solutions, suspensions, emulsions, syrups and elixirs. The active ingredient can be dissolved or suspended in a pharmaceutically acceptable liquid carrier such as water (of appropriate purity, e.g., pyrogen-free, sterile, etc.), an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Compositions for oral administration can be in either liquid or solid form. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. Suitable examples of liquid carriers for oral and parenteral administration include water of appropriate purity, aqueous solutions (particularly containing additives, e.g. cellulose derivatives, sodium carboxymethyl cellulose solution), alcohols (including monohydric alcohols and polyhydric alcohols e.g. glycols) and their derivatives, and oils. For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant. Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form. The carrier can also be in the form of creams and ointments, pastes, and gels. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable.

Compounds of the invention and of formulas I, II, III or IV include pharmaceutically acceptable salts, if any, of various compounds. The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like.

In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. Compounds herein may also be present in the form of zwitterions.

Compounds of the invention can be in the form of salts which in specific embodiments are non-toxic and more specifically pharmaceutically-acceptable. Pharmaceutically acceptable salts comprise pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., $Cl^-$, $Br^-$), sulfate, acetates (e.g., acetate, trifluoroacetate), ascorbates, aspartates, benzoates, citrates, and lactate.

Compounds of the invention can have prodrug forms. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

The invention expressly includes pharmaceutically usable solvates of compounds according to formulas herein. The compounds can be solvated, e.g. hydrated. The solvation can occur in the course of the manufacturing process or can take place, e.g. as a consequence of hygroscopic properties of an initially anhydrous compound of formulas herein (hydration).

Well-known methods for assessment of drugability can be used to further assess active compounds of the invention for application to given therapeutic application. The term "drugability" relates to pharmaceutical properties of a prospective drug for administration, distribution, metabolism and excretion. Drugability is assessed in various ways in the art. For example, the "Lipinski Rule of 5" for determining drug-like characteristics in a molecule related to in vivo absorption and permeability can be applied (C. A. Lipinski, F. Lombardo, B. W. Dominy, P. J. Feeney, Experimental and computational approaches to estimate solubility and permeability in drug discovery and development settings, Adv. Drug Del. Rev., 2001, 46, 3-26 and Arup K. Ghose, Vellarkad N. Viswanadhan, and John J. Wendoloski, A Knowledge-Based Approach in Designing Combinatorial or Medicinal Chemistry Libraries for Drug Discovery, J. Combin. Chem., 1999, 1, 55-68.)

In general a preferred drug for oral administration exhibits no more than one violation of the following rules:
(1) Not more than 5 hydrogen bond donors (e.g., nitrogen or oxygen atoms with one or more hydrogens);
(2) Not more than 10 hydrogen bond acceptors (e.g., nitrogen or oxygen atoms);
(3) Molecular weight under 500 g/mol and more preferably between 160 and 480; and
(4) log P less than 5 and more preferably between −0.4 to +5.6 and yet more preferably −1<log P<2.

Compounds of this invention preferred for therapeutic application include those that do not violate one or more of 1-4 above.

Compounds of this invention preferred for therapeutic application include those having log P less than 5 and more preferably between −0.4 to +5.6 and yet more preferably −1<log P<2.

The compounds of this invention may contain one or more chiral centers. Accordingly, this invention is intended to include racemic mixtures, diastereomers, enantiomers and mixture enriched in one or more stereoisomer. The scope of the invention as described and claimed encompasses the racemic forms of the compounds as well as the individual enantiomers and non-racemic mixtures thereof.

It is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein.

As used herein, the term "treating" includes preventative as well as disorder remittent treatment. In an embodiment, treating herein includes treatment other than prevention. As used herein, the terms "reducing", "suppressing" and "inhibiting" have their commonly understood meaning of lessening or decreasing.

In certain embodiments, the present invention encompasses administering the compounds useful in the present invention to a patient, subject or individual. A "patient," "subject," or "individual", as used equivalently herein, refers to an animal. In particular, an animal refers to a mammal, preferably a human. The patient either: (1) has (is diagnosed to have or is believed to have) a condition remediable or treatable by administration of a compound of the invention; or (2) is susceptible to a condition that is preventable by administering a compound of this invention.

Additional embodiments of the invention include the following.

In an embodiment, the present invention provides a surface coating or polymer having incorporated therein a combination of compounds of the present invention. The amount of compounds or polymer in the surface coating is that sufficient to provide antifouling effect or provide for bacterial inhibition. In an embodiment, the compounds or combinations thereof of the invention are useful as an antifouling agent or surface sterilizing agent. In specific embodiments, the compounds of this invention exhibit no substantial antimicrobial effect. Compounds of the invention are further useful in a medical, scientific, and/or biological application.

In one aspect, the invention provides a composition comprising one, two or more compounds of the invention and a carrier or diluent. In a preferred embodiment, the carrier or diluent comprises a liquid. Such a liquid may comprises an aqueous solvent or a non-aqueous solvent. An exemplary solvent comprises one or more organic solvents. The carrier or diluent may also comprise an ionic liquid. In an embodiment of this aspect, the composition comprises an organic or inorganic polymeric substance. The polymeric substance may comprise one or more compounds of the present invention, admixed with a polymer, bound to a polymer, or adsorbed on to a polymer. In an exemplary embodiment of this aspect, the composition is in the form of a solution or suspension of said at least one compounds of the invention, preferably in an aerosol or powder formulation.

In an embodiment, the composition comprising one or more LasR modulators is formulated as a disinfectant or cleaning formulation. In another embodiment, the composition is in the form of a powder, a solution, a suspension, a dispersion, an emulsion, or a gel. In an exemplary embodiment, the composition is in the form of a pharmaceutical composition comprising a pharmaceutically acceptable carrier, diluent, and/or excipient and one or more compounds of the present invention. The composition may be in a form suitable for parenteral or non-parenteral administration. A preferred composition may be formulated for topical, intradermal, intramuscular, intraperitoneal, intravenous, subcutaneous, intranasal, epidural, ophthalmic, or oral administration. In an embodiment of this aspect the composition is formulated for administration by infusion or bolus injection, absorption through epithelial or mucocutanous linings and may be administered together with other biologically active agents. In an embodiment, the composition may further be formulated for use in an inhaler or nebulizer.

In another aspect, the present invention provides a method of treating an infection in a human or animal, the method comprising administration to the individual (human or animal) of a therapeutically effective amount of one or more compounds of the invention. In an embodiment, the treatment is therapeutic or prophylactic.

In a related embodiment, the present invention provides a method of treating an infection or condition in an individual that is characterized by biofilm formation, the method comprising administering one or more compounds of the invention. In an embodiment, the condition is cystic fibrosis. In an embodiment, the condition is dental caries, periodontis, otitis media, muscular skeletal infections, necrotizing fasciitis, biliary tract infection, osteomyelitis, bacterial prostatitis, native valve endocarditis, cystic fibrosis pneumonia, or meloidosis. In an embodiment, the condition is a nosocomial infection; preferably the infection is ICU pneumonia or an infection associated with sutures, exit sites, arteriovenous sites, scleral buckles, contact lenses, urinary catheter cystitis, peritoneal dialysis (CAPD) peritonitis, IUDs, endotracheal tubes, Hickman catheters, central venous catheters, mechanical heart valves, vascular grafts, biliary stent blockage, orthopedic devices, or penile prostheses. In an embodiment, the infection is a skin infection, a burn infection, or a wound infection. According to this aspect, the individual may preferably be an immune-compromised individual.

In specific embodiments herein, contacting is achieved by release of one or more inhibitory compounds of the invention from a polymer film, multilayer film, hydrogel, or coating that contains the one or more biofilm-inhibitory compounds of the invention. In general, any art-known type of film, hydrogel or coating can be employed for containing and thereafter releasing one or more biofilm-inhibitory compounds of the invention. It will be appreciated that the film or coating (e.g., polymer) must be chemically compatible with and not inactivate the inhibitory compound. In other specific embodiments, contacting is achieved by encapsulation of and later release of one or more inhibitory compounds of the invention into the environment to be. Encapsulation can be by any art known method and can be in the form of micro- or nanoencapsulation.

Methods of this invention can be implemented employing thin films, multilayers, coatings, hydrogels, encapsulation and related delivery methods where the biofilm-inhibitory compounds are loaded in the films, coatings, hydrogels or are encapsulated for delivery over time to an environment having existing biofilms or which is susceptible to biofilm formation. Encapsulation can be in various forms including among others microspheres or nanospheres. The use of such delivery methods can provide for release of one or more biofilm-inhibitory compounds over time extending from days to week to months dependent upon the methods and specific materials employed. In specific embodiments, a surface is protected from biofilm formation by application of a thin film, a multilayer, a coating or the like to at least a portion of the surface. In a related embodiment, surfaces are protected from biofilm formation or cleaned of biofilms by application of a thin film, a multilayer, a coating or the like to a surface in the vicinity of the surfaces to be protected in order to release an effective amount of biofilm-inhibitory compound of the invention into the vicinity of the surfaces to be protected. In specific embodiments, films, multilayers, coatings or encapsulation methods provide a level of the biofilm-inhibitory compound to the surface or to the vicinity of a surface to be protected which ranges from the $IC_{50}$ of the compound for biofilm inhibition to less than the toxicity level of the compound for mammalian cells. In specific embodiments, the concentration of biofilm-inhibitory compounds provided by such films, multilayers, coatings or encapsulation methods to the environment to be protected ranges from the IC50 of the compound to less than 0.25 mM. More specifically, the concentration provided to the environment to be protected ranges from 10-100 micromolar.

In specific embodiments, films, multilayers and coatings generated using one or more polymers and which contain from about 0.001 to 1 mg or more preferably from 0.01 to 1 mg/gram of biofilm-inhibitory compound/gram of polymer are useful for biofilm inhibition or dispersion. In a specific embodiment, biofilm-inhibitory compounds of the invention are provided to a surface or a portion of a surface in film formed from a poly(lactide-co-glycolide).

The present invention further provides a method for treating or preventing biofilm formation on a surface, the method comprising contacting said surface with combined compounds of the invention in an amount effective for affecting biofilm formation of the present invention. In an embodiment, the surface is a non-biological surface. In an embodiment, the surface is a natural surface. In an embodiment, the surface is a surface of a plant, seed, wood, fiber or hair. In an embodiment, the surface is a biological surface; preferably the surface is a surface of a tissue, membrane, or skin. In an embodiment, the surface is a hard surface; preferably the surface comprises a metal, an organic polymer, an inorganic polymer, a natural elastomer, a synthetic elastomer, glass, wood, paper, concrete, rock, marble, gypsum, or ceramic. In an embodiment, the said surface is coated or wherein the surface is a coating; in a preferred embodiment, the coating comprises enamel, varnish, or paint.

In an embodiment of this aspect, the surface is a soft surface, and may be the surface of a fiber comprising a yarn, a textile, a vegetable fiber, or rock wool. In another embodiment, the surface is a porous surface. In an embodiment, the surface is a surface of process equipment or components of cooling equipment. In a preferred embodiment, the process equipment is or is a component of a cooling tower, a water treatment plant, a dairy processing plant, a food processing plant, a chemical process plant, or a pharmaceutical process plant. In a preferred embodiment the surface is that of a filter or a membrane filter.

In an embodiment of this aspect, the surface is a surface of a toilet bowl, a bathtub, a drain, a high-chair, a counter top, a vegetable, a meat processing room, a butcher shop, food preparation areas, an air duct, an air-conditioner, a carpet, paper or woven product treatment, a diaper, personal hygiene products and a washing machine. In another embodiment, the surface is an industrial surface or a medical surface; preferably the surface is a surface in a hospital, a veterinary hospital, a mortuary, or a funeral parlor.

In another aspect, the LasR modulators of the invention are useful as a component of a dentifrice, a mouthwash, or a composition for the treatment of dental caries; for treatment of acne; or for cleaning and/or disinfecting contact lenses. The compounds of the invention are further useful for incorporation into the surface of a medical device or an implant device. Preferably the implant device is an artificial heart valve, hip joint, an indwelling catheter, pacemaker, or surgical pin. The compounds of the invention are further useful as an antifouling coating. The invention further provides an optical lens, wherein at least a part of a surface of the lens is associated with one or more compounds of the invention. Preferably, the optical lens is a contact lens.

In another aspect, the invention provides a biofilm removing or inhibiting composition comprising one or more compounds of the invention in an amount effective for removing or inhibiting biofilm formation and a vehicle or carrier, wherein the amount of the mixture is effective to remove or disrupt a bacterial biofilm or inhibit normal biofilm formation. An embodiment of this aspect may further comprise a surfactant selected from the group consisting of an anionic surfactant, a nonionic surfactant, an amphoteric surfactant, a biological surfactant, and any combination of these; or a compound selected from the group consisting of a biocide, a fungicide, an antibiotic, and any combination of these.

The term antibacterial agent refers generically to chemical species that exhibit bacteriostatic or bactericidal effect. Of particular interest are antibacterial agents effective against one or more Gram-negative bacteria and particularly those that are effective against *Pseudomonas*, and more particularly against *P. aeruginosa*. Antibacterial agents include disinfectants such as chlorine, bromine and chlorine dioxide and quaternary ammonium compounds as well as antibiotics. A variety of antibiotics are known in the art and one of ordinary skill in the art can select one or more antibiotics appropriate for use against a given species or strain of Gram-negative bacteria. Antibiotics useful in the method of this invention include among others gentamicin, kanamycin neomycin, streptomycin and other aminoglycoside antibiotics which are of particular use against *P. aeruginosa* infections.

Additional exemplary classes of antibiotics include among others Penicillins, Cephalosporins, Carbapenems, Tetracyclines, Macrolides, Quinolones and Sulfonamides. One of ordinary skill in the art can readily chose amongst known antibiotics of these classes for use in the methods herein.

In another embodiment, the invention provides a film, multilayer film, hydrogel or coating, for application to a surface or in the vicinity of a surface, containing a combination of compounds of the invention to inhibit or prevent biofilm formation on the surface.

In another embodiment, the invention provides a combination of compounds of the invention, such as a pharmaceutical composition, a disinfectant composition, an encapsulated formulation, a coating for application to a surface or similar composition. Such compositions are useful to regulate a symbiotic behavior of quorum sensing bacteria. This symbiotic behavior may be biofilm formation. Other symbiotic behaviors that may be regulated include swarming, motility, sporulation, conjugation, bioluminescence and/or production of pigments, antibiotics and enzymes. Quorum sensing molecules of the formulas of this invention may in one embodiment inhibit, decrease or attenuate a behavior of quorum sensing bacteria, particularly Gram-negative quorum sensing bacteria, particularly *Pseudomonas* and more particularly *P. aeruginosa*.

In an embodiment, a coating containing one or more LasR modulators of the invention can be applied to a variety of surfaces using methods that are well-known in the art. The coating may be in the form of a film, including a multi-layer film, or a gel, particularly a hydrogel, comprising one or more of the compounds of this invention. Coatings can be employed in medical and non-medical applications. Specific applications include coated medical devices (e.g., stents, catheters, and feminine hygiene products) and industrial coatings (e.g., ship hulls and heat exchangers). The coating may be applied to the surfaces of interest using a variety of known methods. In specific embodiments, the coating loaded with one or more inhibitory compounds of this invention is formed by solvent casting. In other embodiments, the loaded coating is formed by spin coating. In other embodiments, the loaded coating is formed by dip coating. In other embodiments, one or more of solvent casting, spin coating or dip coating is employed to form surfaces carrying inhibitory loaded films of this invention.

In an embodiment, inhibitory compounds and combinations thereof the invention can be encapsulated in thin bulk films of conventional polymers, such as PLA, or PLGA by known methods such as dip-coating or solvent casting. Such films can be applied to surfaces as desired where the encapsulated inhibitor is released to inhibit or prevent biofilm formation on the surface. In an embodiment, biofilm inhibitors of this invention can be loaded into nanostructured polymer multilayers, for example, PEMs and other cross-linked multilayers, for example, using a layer-by-layer approach. Multilayers can be applied to or formed on surfaces to release biofilm inhibitor to inhibit or prevent biofilm formation on the surface. Sustained release of the inhibitors can be obtained using such methods. Methods useful for making films or coatings including multilayer films are described, for example, in Lynn and co-workers: Adv. Mater. 2007; Biomacromolecules 2009; Adv. Mater. 2010; Langmuir 2010; ACS App. Mater. Inter. 2010; Langmuir 2010; Chem. Mater. 2010; J. Mater. Chem. 2011; Adv. Biomat. 2011; Biomacromolecules 2011 and in U.S. Pat. Nos. 7,883,720; 8,071,210 and published US applications US20080286345 and US20090105375, each of which is incorporated by reference herein for descriptions of methods and materials, particularly polymers and co-polymers, useful for forming films, multilayer films and the like. It will be appreciated that combinations of the invention can be individually encapsulated or otherwise formulated and such individual encapsulated compounds or other individual formulations can be combined in an application, contacting step or administration step to achieve the desired combined effect that is discussed herein.

More generally for contact or administration herein, one or more compounds can applied to a bacterium, an environment of a bacterium or administered to a patient simultaneously or separately, at the same site at the same time or a different time, in the same type of formulation or dosage form or in a different type of formulation or a different dosage form.

In specific embodiments, the invention provides films, coatings or hydrogels containing one of or a combination of the inhibitory compound of the invention. In specific embodiments, films, coatings and/or hydrogels or the like of this invention provide a concentration of an inhibitory compound into the environment to be protected (e.g., a surface) that is effective for inhibiting virulence. In an embodiment, such coatings, inhibit formation of a biofilm or disperse an already formed biofilm. Such coatings can provide for some level of decrease of bacteria on such surfaces. In specific embodiments, films, coatings and/or hydrogels or the like of this invention provide a concentration of a one or more inhibitory compounds into the environment to be protected that ranges from the $IC_{50}$ of the biofilm-inhibitory compound (which can be measured by methods as described herein) to the level of the compound that is cytotoxic to mammalian cells (which can be measured by methods as described herein). In specific embodiments, films, coatings and/or hydrogels or the like of this invention provide a concentration of a inhibitory compound into the environment to be protected that ranges from the $IC_{50}$ of the inhibitory compound (which can be measured by methods as described herein) to 0.250 mM. In more specific embodiments, the concentration of inhibitory compound provided to the environment to be protected ranges from 4 microM to 200 microM. In yet more specific embodiment, the concentration ranges from 2-10 time the IC50 of the biofilm-inhibitory compound to 200 microM. In additional embodiments, the concentration ranges from 10-200 microM, 10-100 microM, 20-100 microM, 40-200 microM, or 40 to 100 microM. Combination of the compounds of the invention can be achieved by combination of the compounds in a film, coating or hydrogel or can be achieved in a combination of films, coatings or hydrogels wherein each film, coating or hydrogel contains a different compound of the combination of compounds.

In specific embodiments, the loading of the film, coating or hydrogel with the biofilm-inhibitory compound ranges from 0.001 to 1 mg of compound/gram of polymer in the film, coating or hydrogel. In more specific embodiments, the loading of the film, coating or hydrogel with the biofilm-inhibitory compound ranges from 0.005 to 1 mg, 0.01 to 1 mg, 0.05 to 1 mg, 0.1 to 1 mg, 0.5 to 1 mg, 0.01 to 0.5 mg of compound/gram of polymer in the film, coating or hydrogel.

The compounds of the invention can be applied to an environment or administered by individual controlled-release of the component compounds of the combination of inhibitory compounds of the invention or by combined controlled-release of a combination of compounds. Controlled release can be from a film formed on the surface to be protected or on a surface in the vicinity of the surface to be protected. Similar release can be used to disperse already-formed biofilms. Release from the film provides for spatially localized release at or near the surface to be protected or cleaned of biofilm enhancing the effectiveness of biofilm-inhibition. The rate of release can be controlled by changing the composition of film, coating or hydrogel as is known in the art. The release profile from the film can also be affected by varying the thickness of the films and the concentration of the one or more biofilm-inhibitory compounds in the film. The concentration of biofilm-inhibitory compounds in the film can be generally uniform throughout the film or the concentration may be non-uniform in the film.

The film, coating or hydrogel may be formed on the surface of a selected substrate by any known method. For example, the film may be formed by contacting of the surface with a solution of the polymer and active ingredient (e.g., one or more inhibitory compounds), allowing a film to form on the surface and repeating the contacting step until a film of desired thickness is formed. The concentration of active ingredient(s) can be the same or different in the contacting steps. For example, the solution in one or more steps may contain polymer, but no active ingredient.

The films of this invention may also be formed by dip-coating, spin coating, or solvent casting using methods known in the art.

In additional embodiments, the inhibitory compounds of the invention can be provided in bulk objects and optionally released from such objects. Bulk objects include disks, slabs and other substrates and other structural elements that can be implanted, incorporated or used in other ways in biomedical or non-biomedical application. For example, one or more inhibitory compounds of a combination of compounds of the invention can be incorporated into such objects, e.g., by absorption. In a specific embodiment, one or more biofilm-inhibitory compounds of the invention can be introduced into porous matrix of an object to provide for biofilm protection.

In specific embodiments, the inhibitory compounds and combinations thereof of this invention are non-bactericidal or can be employed at levels which are inhibitory without being bactericidal. In such embodiments, concerns associated with evolved resistance currently faced by approaches based on the use of conventional microbiocidal agents (e.g., antibiotics) are lessened.

The term alkyl as used herein refers to a saturated hydrocarbon group which is straight-chain or branched. Unless otherwise stated, an alkyl group can have from 1-20 carbon atoms. More specifically, an alkyl group can have from 1-18 carbon atoms. In certain embodiments, an alkyl group can have from 1-3 carbon atoms. In certain embodiments, an alkyl group can have from 1-5 carbon atoms. In certain embodiments, an alkyl group can have 1-6 carbon atoms.

The term alkoxy refers to an —O-alkyl group where the alkyl group is as defined above.

The term alkenyl as used herein refers to a hydrocarbon group which is straight-chain or branched having at least one double bond. Unless otherwise stated, an alkenyl group can have from 2-20 carbon atoms. More specifically, an alkenyyl group can have from 2-18 carbon atoms. In certain embodiments, an alkenyl group can have from 2-5 carbon atoms. In certain embodiments, an alkenyl group can have from 2-6 carbon atoms. In specific embodiments, an alkenyl group has one double bond. In certain embodiments, an alkenyl group having n carbon atoms has a single double bond positioned between the 3-4 carbon of the alkenyl group, the 4-5 carbons, the 5-6 carbons, the 6-7 carbons, etc. up to the (n–4)-(n–3) carbons. In certain embodiments, an alkenyl group has a γ-double bond at the end of the group distal from its site of attachment to another moiety. In specific embodiments, an alkenyl group has two double bonds.

The term aryl refers to monocyclic or polycyclic (e.g., having 2 or more fused rings). Preferred polycyclic aryl groups have 2 or 3 rings, which may be fused or not fused. Aryl groups include phenyl, naphthyl, indanyl, indenyl, anthracenyl, and phenanthrenyl among others. Aryl groups also include benzodioxolyl. In certain embodiments, aryl groups have 6-20 carbon atoms. The term aryl oxy refers to an —O-aryl group. An example aryl oxy group is phenoxy. In a specific embodiment, aryl groups are substituted phenyl groups.

The term cycloalkyl refers to a non-aromatic cyclic hydrocarbon which can have moncyclic or polycyclic ring systems. Polycyclic ring systems can include those with 2-4 fused rings or 2-4-ring spiro ring systems. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, among others. Carbon atoms of the cycloalkyl group can be optionally oxidized, i.e., have an oxo or sulfildo group to form CO or CS.

Cycloalkenyl groups are cycloalkyl groups having one or more double bonds in the ring. In a specific embodiment, cycloalkenyl groups have a single double bond in the ring. Specific cycloalkenyl groups are cyclopentenyl groups, cyclopentyldienyl groups and cyclohexenyl groups.

The term heterocycyl (also heterocyclic group) refers to non-aromatic heterocyclic group wherein one or more of the ring-forming carbon atoms are replaced by a heteroatom such as an O, N, or S atom. Heterocycyl groups include those having one or more than one ring (not all rings need contain an O, S or N atom). Rings may be fused or non-fused. These groups can also include moieties in which one or more aromatic rings are fused to the nonaromatic heterocyclic ring, for example phthalimidyl, naphthalimidyl, and benzo derivatives of heterocycles such as indolene and isoindolene groups. Heterocycyl groups can be monocyclic or polycyclic and may contain from 1-20 carbon atoms, or in other embodiments, 3 to 20 carbon atoms. In some embodiments, the heterocycyl group contains 3 to 14, 3 to about 7, or 5 to 6 ring forming atoms. In some embodiments, the heterocycyl group has 1 to 4, 1 to 3, or 1 to 2 heteroatoms. In some embodiments, the heterocycyl group contains 0 to 3 double bonds. Exemplary heterocycyl groups include morpholino, thiomorpholino, piperazinyl, tetrahydrofuranyl, tetrahy-drothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, 3H-isobenzofuran-1-one, 1,3-dihydro-isobenzofuran, 2,3-dihydro-benzo[d]isothiazole 1,1-dioxide, among others. Heterocycyl groups include heteroaryl groups.

The term heteroaryl refer to an aromatic heterocyclic group having at least one heteroatom ring member such as sulfur, oxygen, or nitrogen. Heteroaryl groups can be monocyclic or polycyclic (e.g., having 2, 3 or 4 fused rings) systems. Exemplary heteroaryl groups include among others, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl. In certain embodiments, the heteroaryl group has from 1 to about 20 carbon atoms. In other embodiments, the heteroaryl group has from 3 to 20 carbon atoms. In certain embodiments, a heteroaryl group contains 3 to 14, 3 to 7, or 5 to 6 ring-forming atoms. In certain embodiments, the heteroaryl group has 1 to 4, 1 to 3, or 1 to 2 heteroatoms.

The above groups may generally be substituted. The various chemical groups defined above may be unsubstituted or substituted at a carbon or at a heteroatom, with one or more non-hydrogen substituents. Generally, non-hydrogen substituents for the above groups include halogen, alkyl group having 1-6 or 1-3 carbon atoms, alkoxy group having 1-6 or 1-3 carbon atoms, —SH, alkylsulfanyl (—S-alkyl) group having 1-6 or 1-3 carbon atoms, a haloalkyl having 1-6 or 1-3 carbon atoms, a haloalkoxy having 1-6 or 1-3 carbon atoms, nitro, cyano, isocyano, thiocyano, isothiocyano, —$SO_2$, —OH, azide, sulfhydryl (—SH), —$CO_2H$, —COH, —NHCOH, —$CONH_2$, —$OCONH_2$, —$NH_2$, —$CO_2R$, —COR, —NHCOR, —$CON(R)_2$, —$OCON(R)_2$, or —$N(R)_2$, where R is C1-C3 alkyl. Substituents also include phenyl group which is in turn are optionally substituted with one or more of the listed non-hydrogen substituents, or benzyl groups which are in turn optionally substituted with one or more of the listed non-hydrogen substituents. Substitution also included substitution of one or more —O—, —S—, —NH—, —CO—, or —CS— in a carbon or heterocyclic ring.

As to substitution of any of the above groups, it is understood, that such groups do not contain any substitution or substitution patterns which are sterically impractical and/or synthetically non-feasible. In addition, the compounds of this invention include all stereochemical isomers arising from the substitution of these compounds.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the invention.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomer and enantiomer of the compound described individual or in any combination. Where a specific enantiomer is described, it is understood that this description includes the substantially pure enantiomer (95% or more pure with respect to the other enantiomer(s)) as well as non-racemic mixtures of enantiomer where the specified enantiomer is present in an amount greater than 50% (by moles) or in an amount greater than 75% (by moles) or in an amount greater than 85% (by moles). Compounds of formula I and II include isotopic variants where the isotopic ratios of one or more atoms of the compound are selectively adjusted, for example, one or more H are replaced with deuterium or tritium, or one or more $^{12}C$ are replaced with $^{13}C$ or $^{14}C$, etc. Such isotopic variants are useful at least in analytical and biological assays.

One of ordinary skill in the art will appreciate that synthetic methods and starting materials, analytical assays, functional assays, Gram-negative bacteria, growth and assay conditions other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the invention.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

Each references cited herein is incorporated by reference herein in its entirety for descriptions of compounds that regulate quorum sensing that are known in the art. Any such compounds disclosed in the cited references can be included or excluded from compound and/or method claims herein. References cited herein may provide methods for synthesis and methods of analysis that are useful for preparation of compounds herein or for assessment of activity of compounds herein.

THE EXAMPLES

Example 1: Synthesis of Certain Compounds of Formula I

Scheme 1 illustrates a method for synthesis of compounds of Formula I

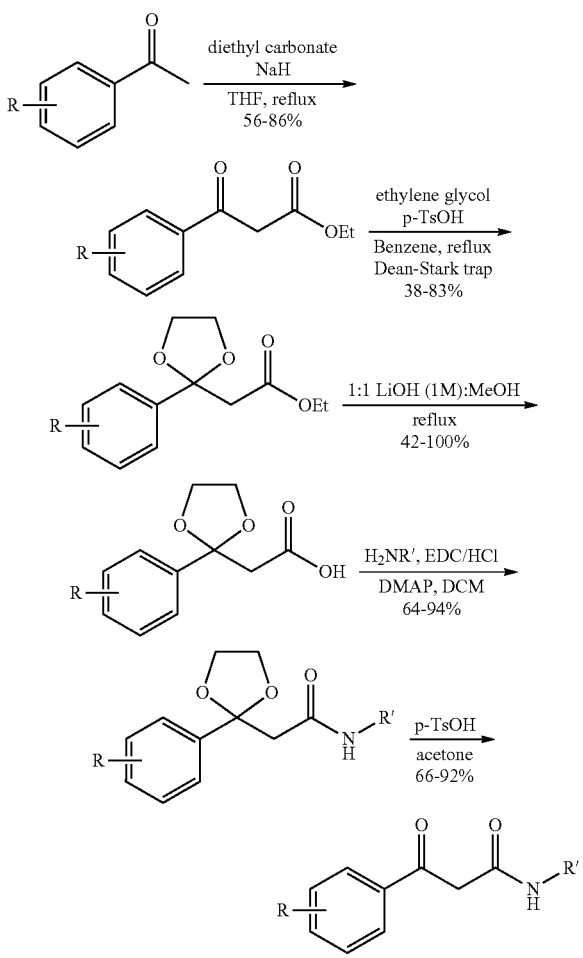

Representative Syntheses of 3-(furan-2-yl)-n-nonyl-3-oxopropanamide, n-dodecyl-3-(furan-2-yl)-3-oxo-propanamide (Scheme 2)

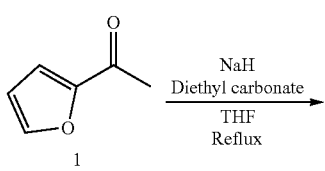

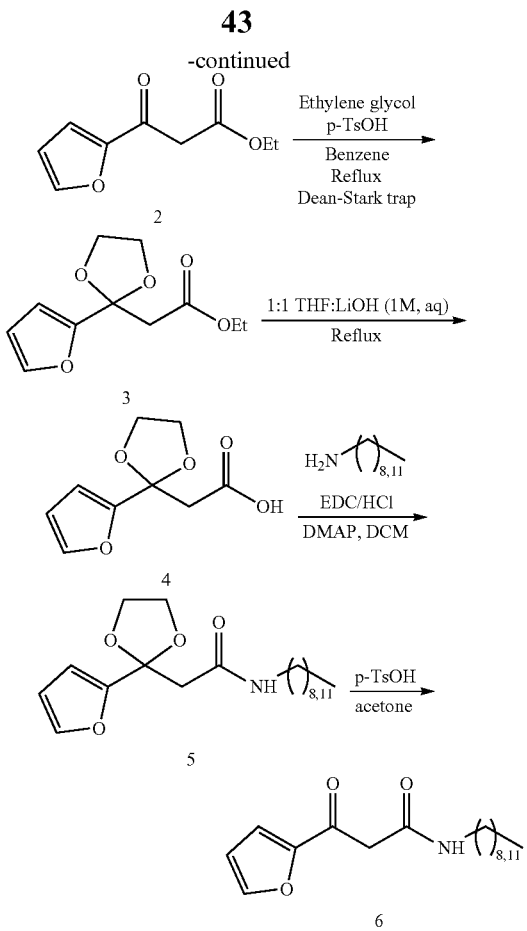

Synthesis of β-ketoesters 2

To a solution of 2-acetylfuran 1 (1 eq) in THF (0.5M), was added NaH (2 eq). The solution was brought to reflux. The reaction was monitored by NMR. Upon consumption of the starting material, the reaction mixture was diluted with diethyl ether. The mixture was then washed with 1M HCl, water, and saturated brine. The organic layer was separated, dried over magnesium sulfate, filtered, and concentrated under reduced pressure.

Synthesis of β-ketal Esters 3

To a solution of β-keto ester (1 eq) in benzene (0.2M) was added p-TsOH (0.1 equiv) and ethylene glycol (6 equiv) at 90° C. A Dean-Stark trap was assembled and the experimental apparatus was insulated with glass wool and tin foil. The mixture was allowed to reflux overnight. The mixture was washed with saturated sodium carbonate (2×30 mL), water (30 mL) and saturated brine (30 mL). The organic layer was separated, dried over magnesium sulfate, filtered, and concentrated under reduced pressure. Compounds were purified via flash chromatography with hexanes and ethyl acetate as solvent.

Synthesis of β-ketal Acids 4 To a solution of β-ketal esters 3 in a 1:1 solution of MeOH and THF (0.1M) was added aqueous 1M LiOH (10 eq) at 75° C. The reaction progress was monitored by TLC. Upon completion, the solution was then allowed to cool to RT. The aqueous layer was separated and its pH was adjusted to 2-3 with citric acid (10% w/v). The acidified aqueous layer was washed with EtOAc (3×). The EtOAc was dried over magnesium sulfate and concentrated under reduced pressure. Products were used without further purification.

Synthesis of β-ketal Amides 5 To a solution of B-ketal acids (1 eq) 4 in dichloromethane (0.1M) was added DMAP (0.15 equiv) and EDC.HCl (1.5 eq). After 10 minutes stirring at room temperature was added either nonylamine or dodecylamine (1.2 equiv). The solution stirred at room temperature overnight. The mixture was diluted with diethyl ether and washed with 1M HCl, saturated sodium bicarbonate (15 mL), and saturated brine. The organic layer was separated, dried over magnesium sulfate, and concentrated under reduced pressure. Products were used without further purification.

Synthesis of B-keto Amides 6

To a solution of B-ketal amides in acetone (0.1 M) was added p-toluene acid (0.1M) at room temperature. The mixture was allowed to stir overnight. The solution was diluted with diethyl ether, washed with saturated sodium bicarbonate, water (15 mL), and saturated brine. The organic layer was separated, dried over magnesium sulfate, and concentrated under reduced pressure. Products were purified via flash chromatography with hexanes and ethyl acetate as solvent.

Hydroxyl ketones, exemplified by those of formula II, are prepared from the diones exemplified by those of formula I by selective or asymmetric reduction. U.S. Pat. No. 7,659,409 and US published application 2006/0264641 provide methods for such reduction that can be applied for synthesis of compounds of formula II.

Example 2: LasR Activity of Compounds of the Invention

Methods for assessing LasR activation and inhibition are known in the art. More specifically methods as described in Moore et al. 2015 are used herein to assess activation and inhibition.

Table 1 provides exemplary data for Maximum inhibition [%] and $IC_{50}$ [micromolar] at 25 nM OdDHL, both at the 95% confidence interval (95% Cl), of representative compounds of the invention. The chemical structures of the compounds which are assessed in Table 1 are given in FIG. 3. $IC_{50}$ is the concentration of an inhibitor where the response or binding is reduced by half (half maximal inhibitory concentration). Several compounds measured exhibit low microMolar $IC_{50}$. Compounds 11, 33, and 40 are, for example, very potent inhibitors with $IC_{50}$ of about 1 micromolar or less. Compound 30 exhibits high efficiency of inhibition exhibiting 100% maximum inhibition.

Figure 4A:
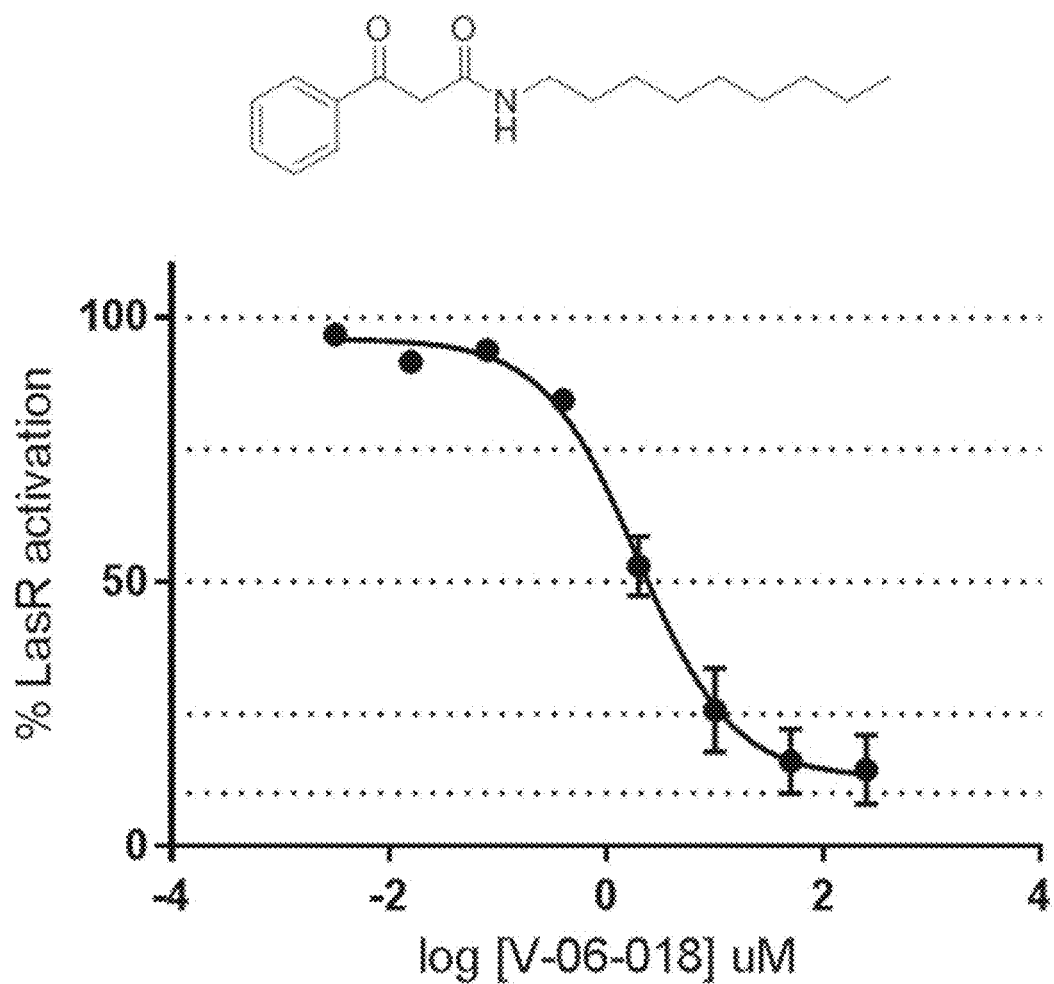
FIGS. 4A-D illustrate the dose response curves for positive control compound V-06-018 (A), compound 33 (B), compound 40 (C) and compound 30 (D).
Figure 4B:
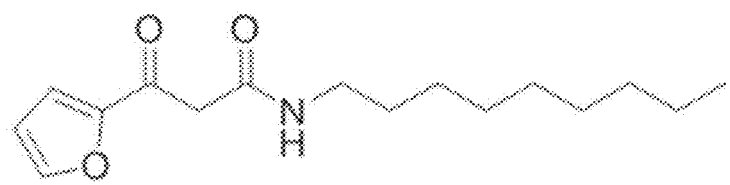
Figure 4B:
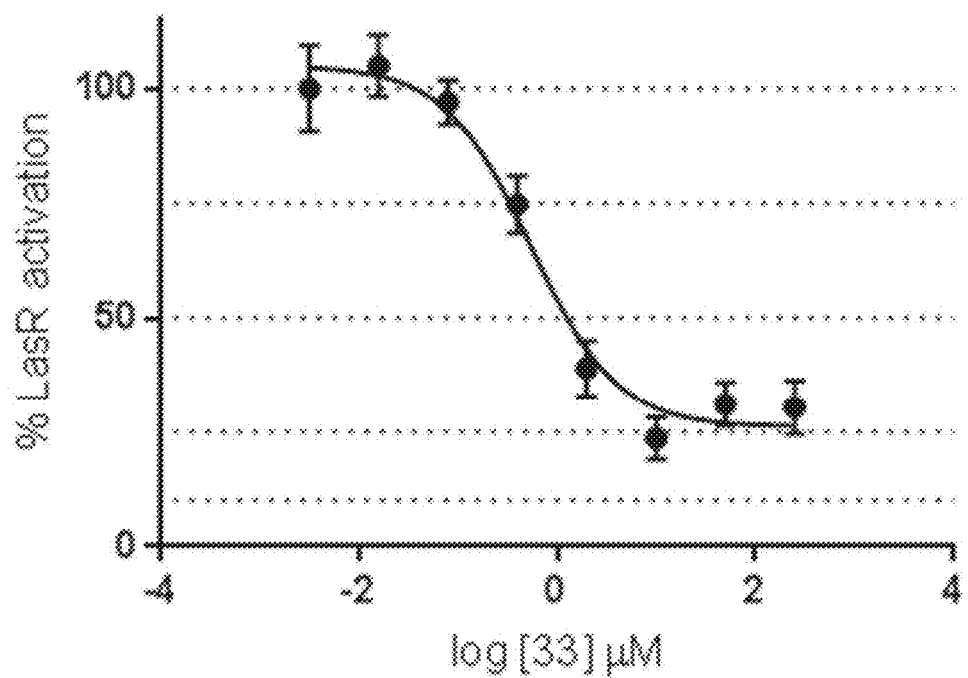
Figure 4C:
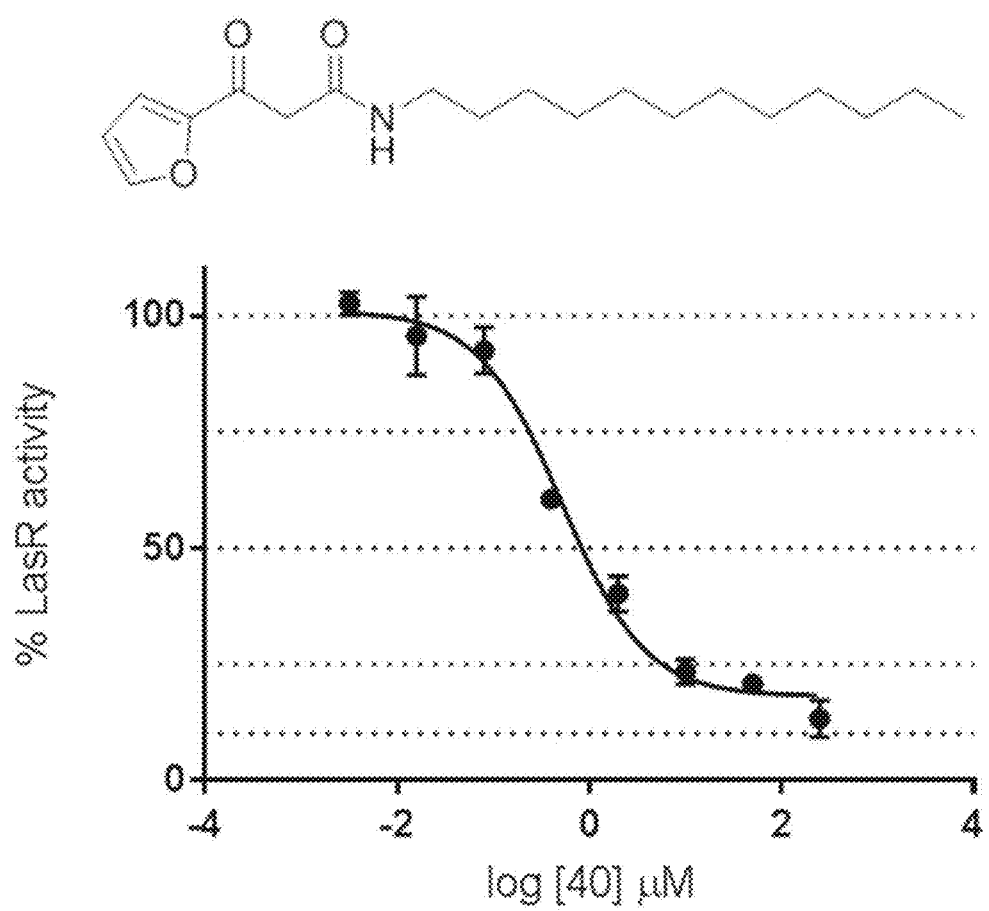
Figure 4D:
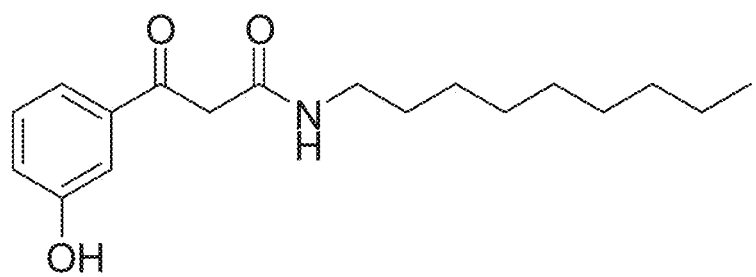
Figure 4D:
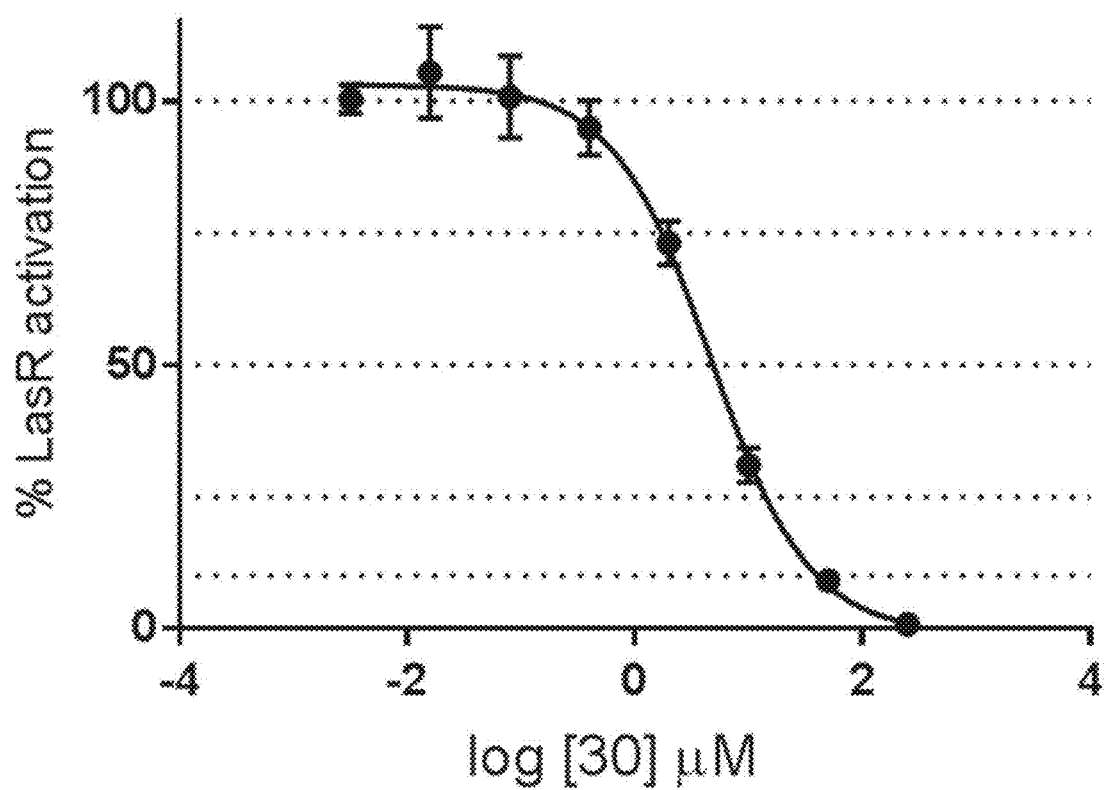

Representative dose response curves are illustrated in FIGS. 4A-4D, where FIG. 4A is that of the control V-06-018.

TABLE 1

Figure 3:
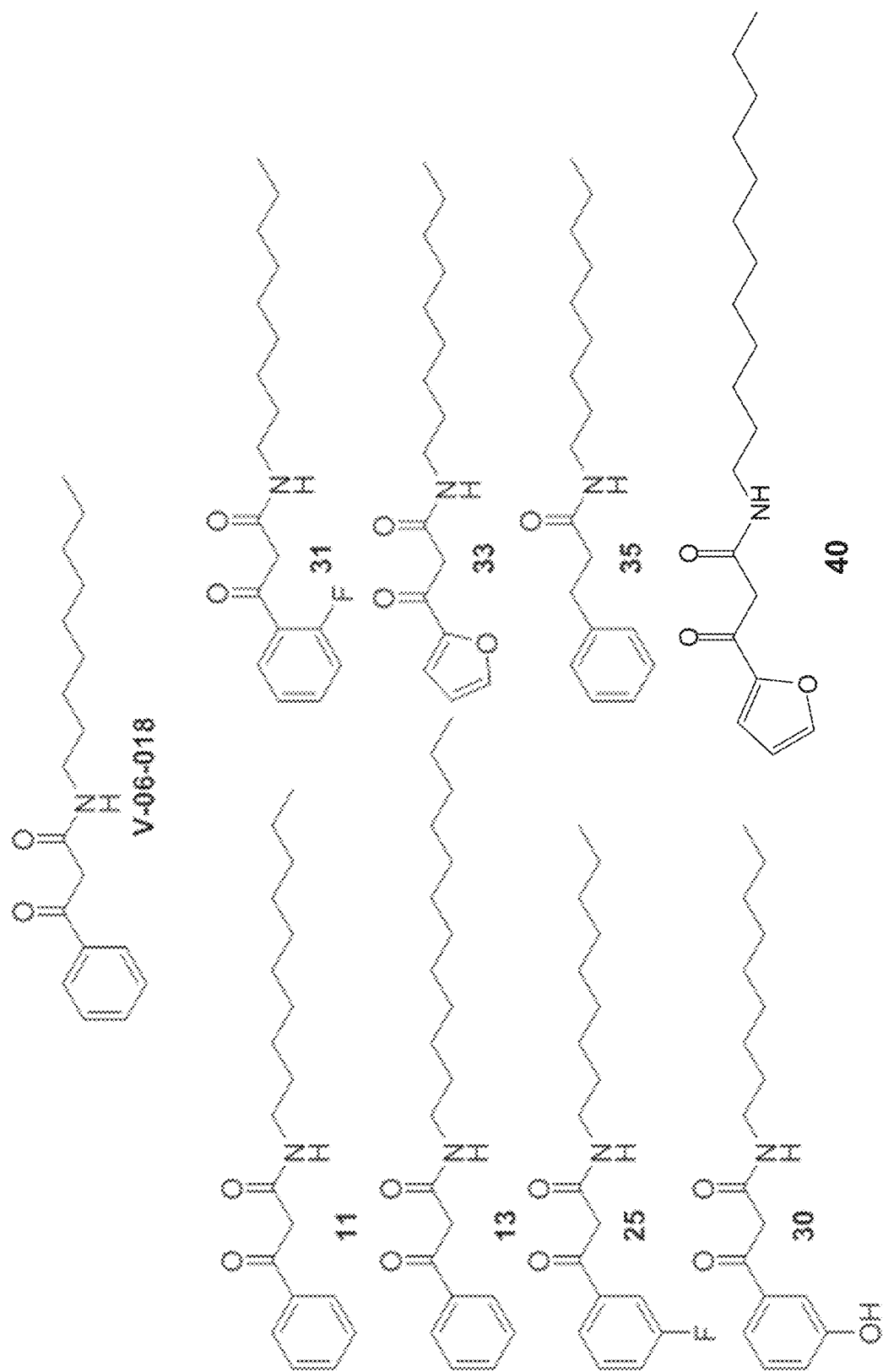
FIG. 3 illustrates the chemical structures of compounds of the invention listed in Table 1.

Exemplary Data for Compounds Illustrated in FIG. 3

| Compound | Maximum Inhibition* (95% CL) [%] | IC50 (95% CL) [microM]* |
|---|---|---|
| V-06-018 | 87 (91-85) | 2.0 (1.5-2.6) |
| 11 | 76 (85-67) | 1.1 (0.5-2.4) |
| 13 | 83 (88-78) | 2.5 (1.7-3.6) |
| 25 | 84 (100-70) | 8.8 (3.2-24) |
| 30 | 100 (105-96) | 4.7 (3.7-5.9) |
| 31 | 74 (93-76) | 3.2 (1.7-5.8) |
| 33 | 74 (81-69) | 0.6 (0.4-0.9) |
| 35 | 80 (87-73) | 7.5 (5.0-11.4) |
| 40 | 82 (85-78) | 0.5 (0.4-0.7) |

*measured vs 25 nM OdDHL

Figure 5A:
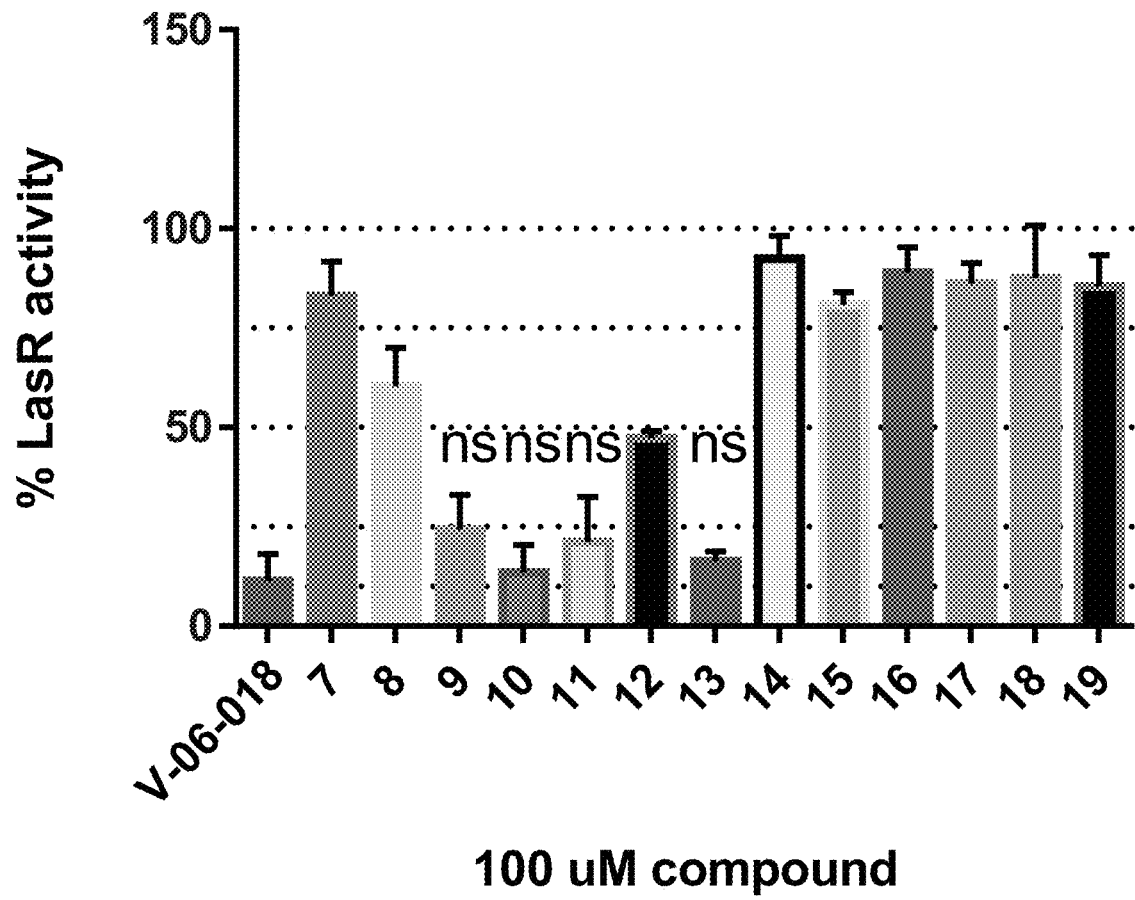
FIG. 5A is a bar graph comparing % LasR activity of selected compounds having structural variation in the tail group.
Figure 5B:
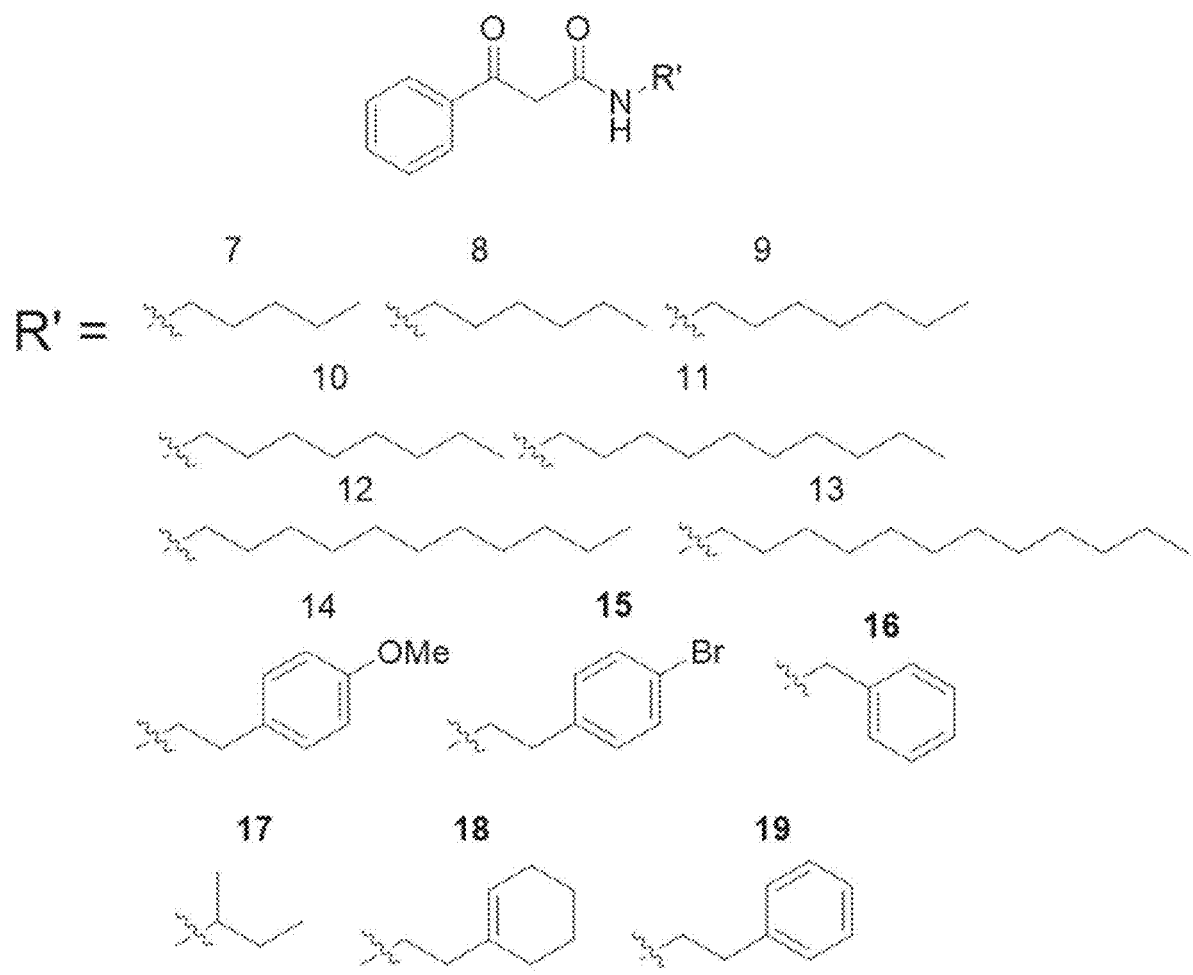
FIG. 5B illustrates the structures of the compounds compared in FIG. 5A.

FIG. 5A is a bar graph of % LasR activity as a function of tail structure with structures shown in FIG. 5B. Compounds with $R_1$ groups that are C7-C12 straight-chain alkyl groups exhibit generally strong inhibition.

Figure 6A:
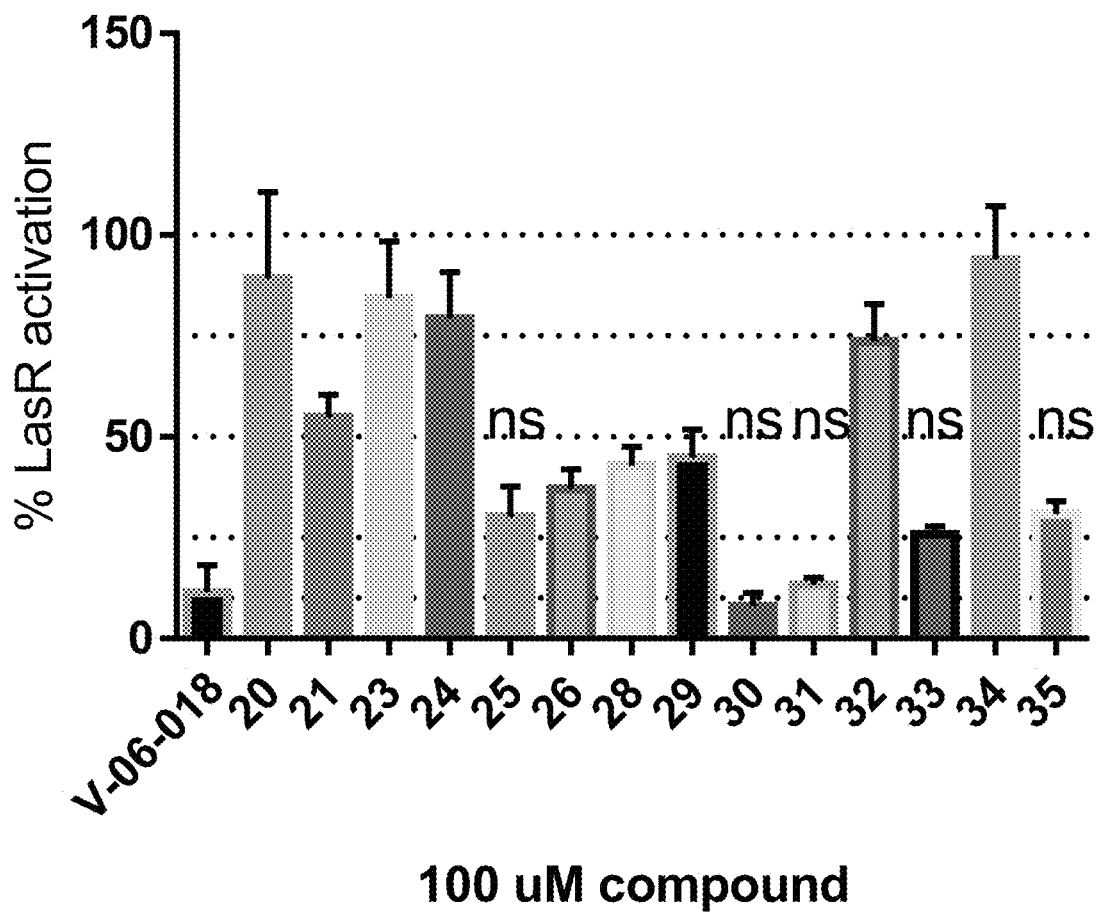
FIG. 6A is a bar graph comparing % LasR activity of selected compounds having structural variation in the head group.
Figure 6B:
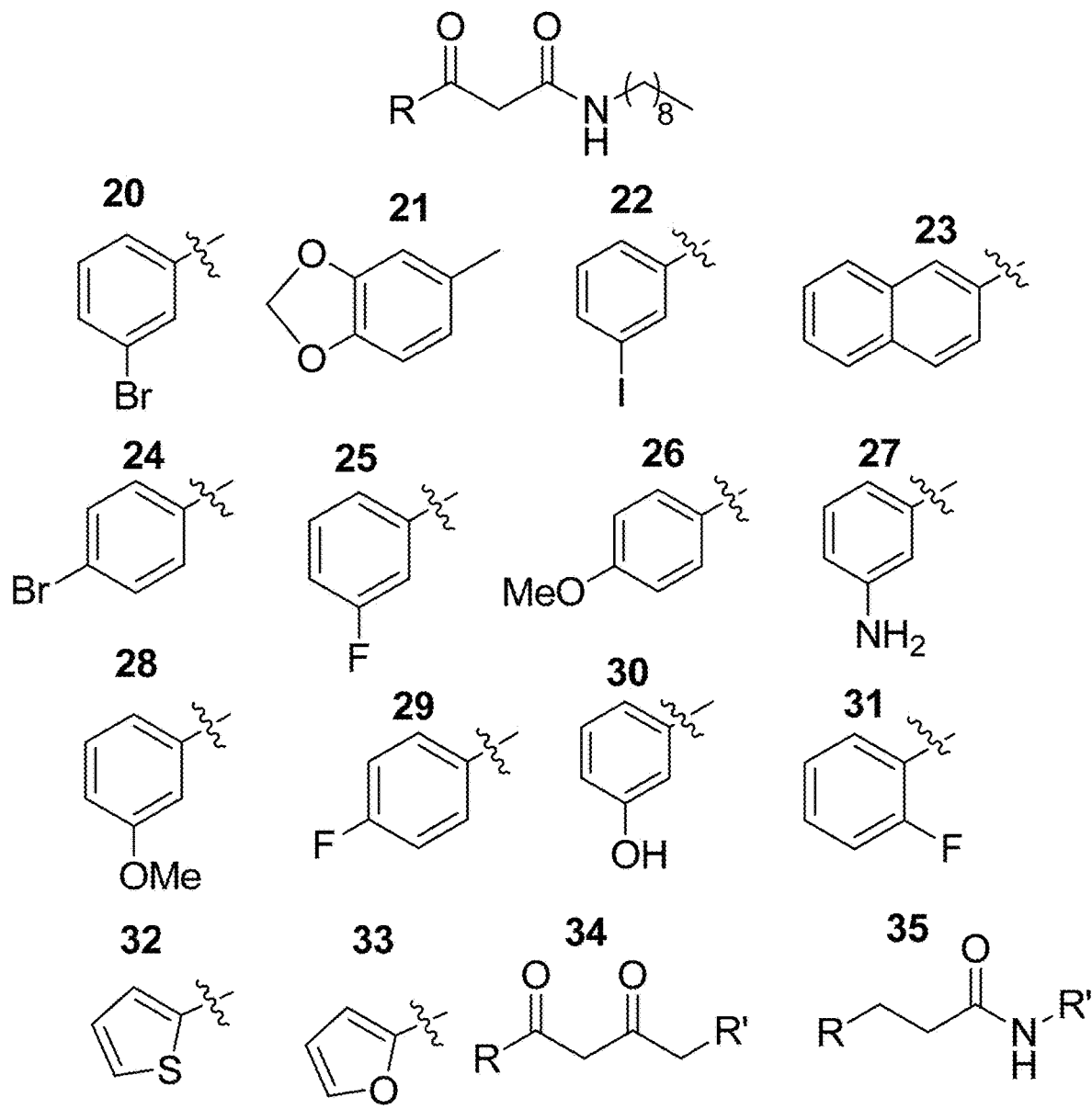
FIG. 6B illustrates the structures of the compounds compared in FIG. 6A.

FIG. 6A is a bar graph of % LasR activity as a function of Head Group structure with structures shown in FIG. 6B. Compounds with AR groups that are furyl groups and certain substituted phenyl groups exhibit generally stronger inhibition.

Figure 7A:
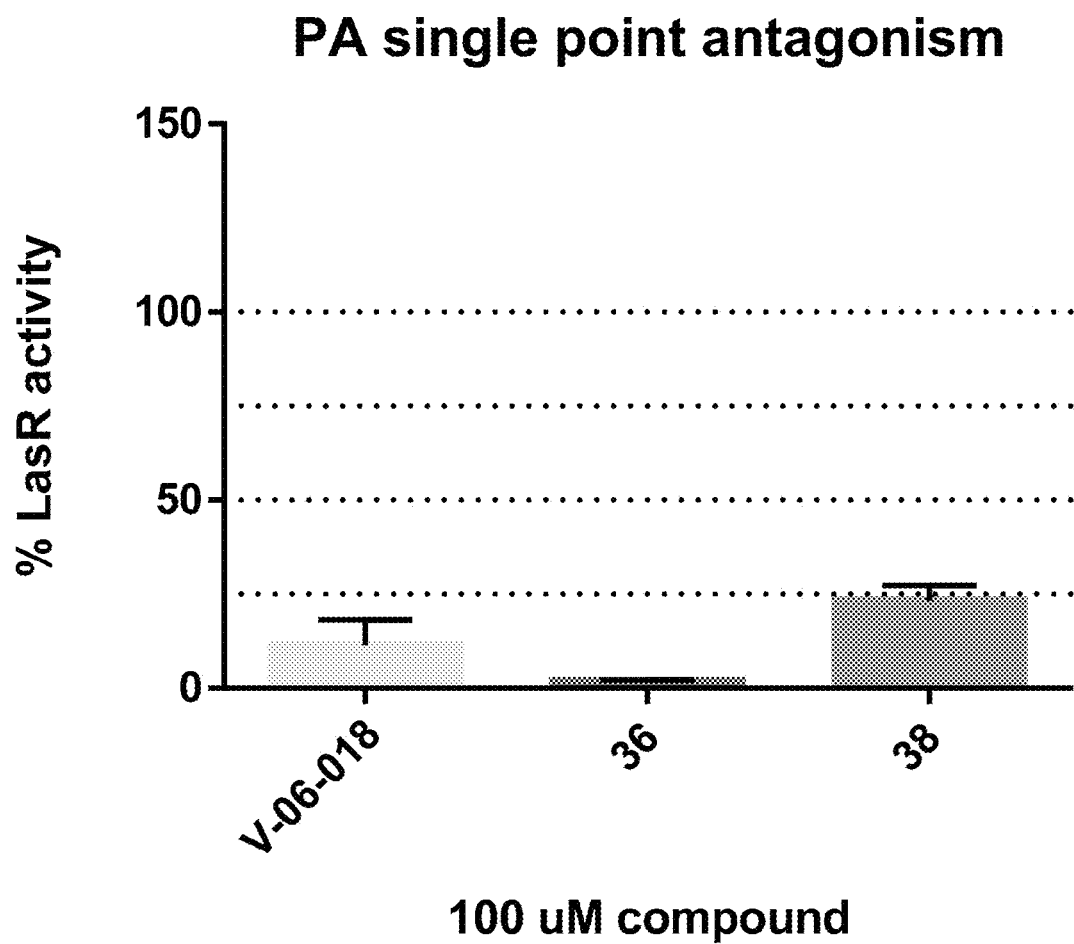
FIG. 7A is a bar graph comparing % LasR activity of compounds 36 and 38 with control V-06-018.
Figure 7B:
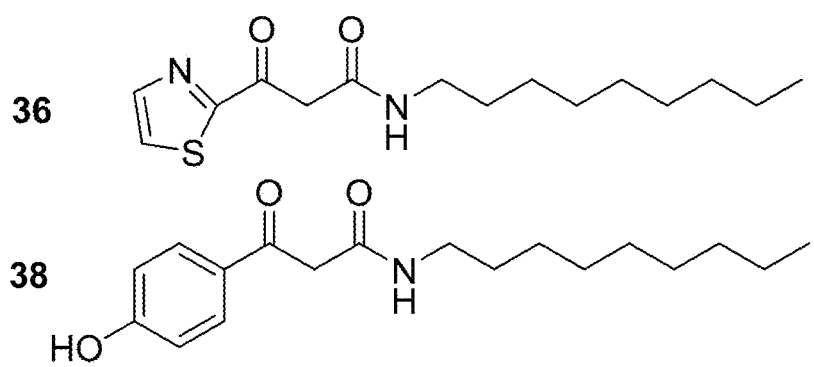
FIG. 7B illustrates the chemical structures of compounds 36 and 38.

FIG. 7A is a bar graph comparing inhibition of compound 36 and 38 to that of control V-06-018. The structures of compounds 36 and 38 are shown in FIG. 7B.

Figure 8A:
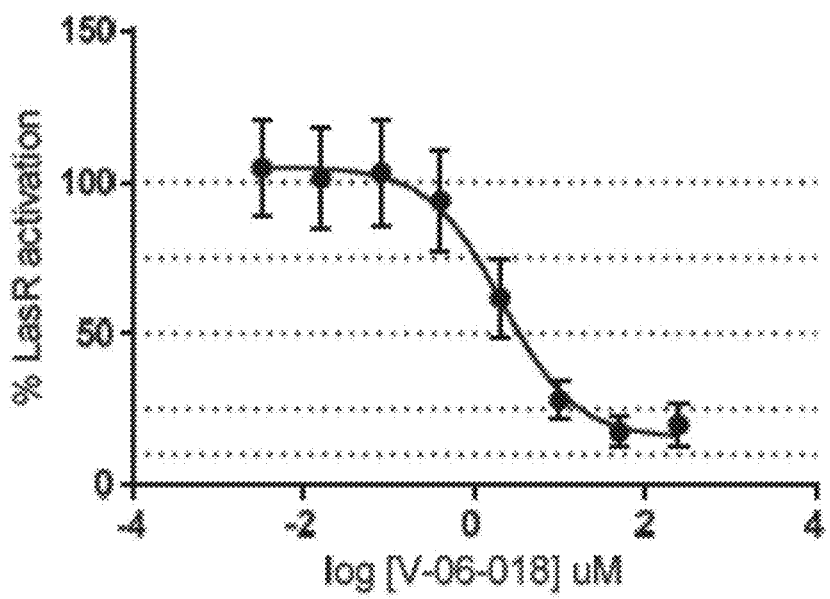
FIGS. 8A and 8B are graphs of % LasR activation as a function of concentration of compound tested which compare the inhibition (antagonism) FIG. 8A, or activation (agonism) FIG. 8B of LasR by the indicated compound.
Figure 8B:
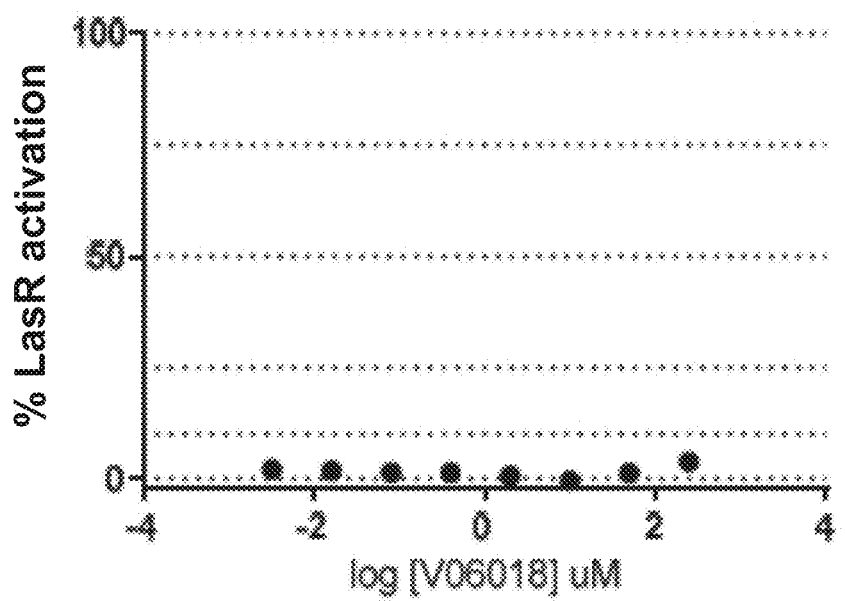

FIGS. 8A and 8B compare % LasR inhibition (8A) with % LasR activation (8B) for control compound V-06-018. The control compound does not exhibit LasR activation.

Figure 9A:
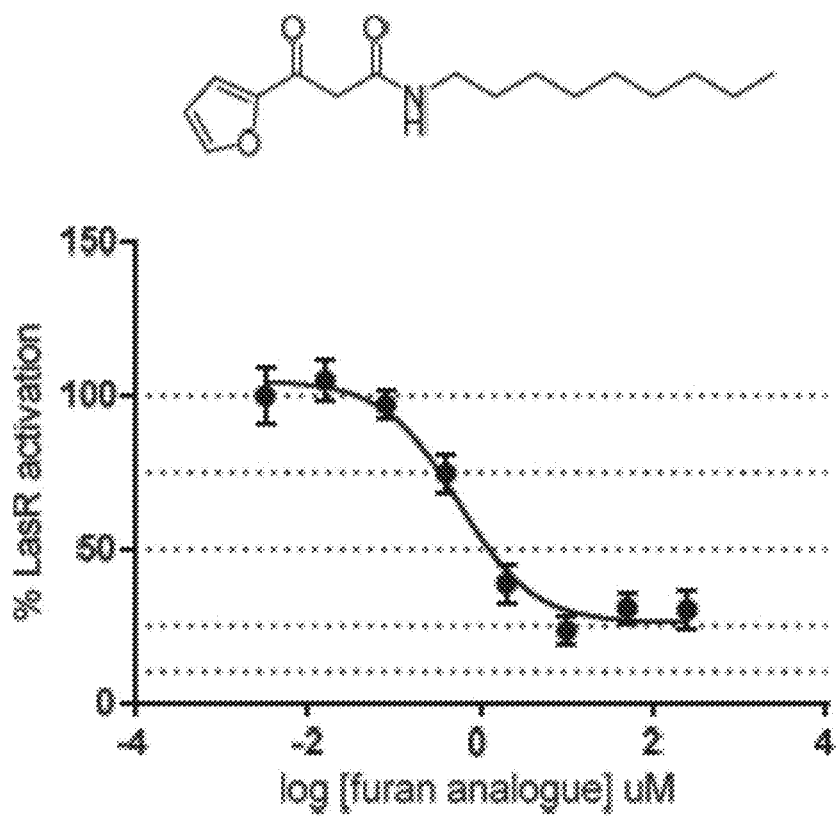
FIGS. 9A and 9B are graphs comparing the inhibition (antagonism) FIG. 9A, or activation (agonism) FIG. 9B of LasR by the indicated compound.
Figure 9B:
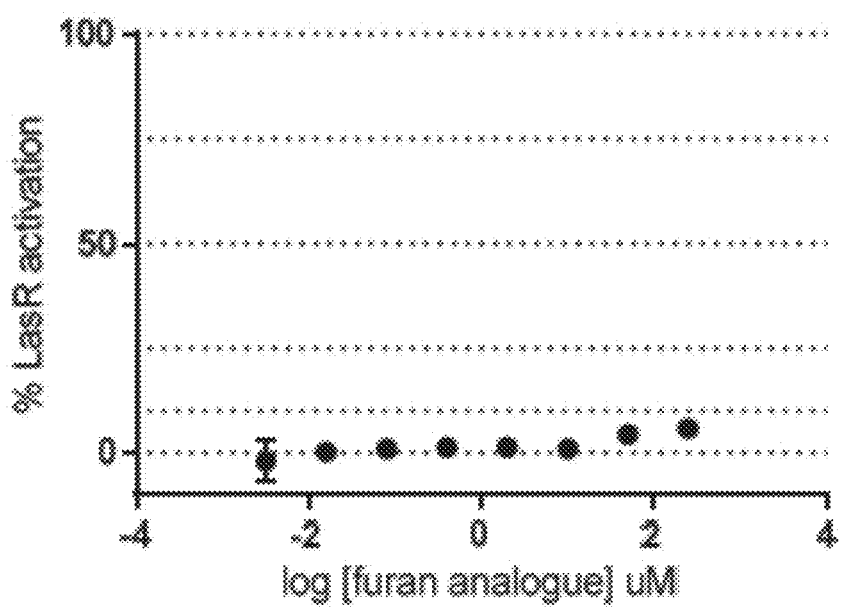

FIGS. 9A and 9B compare % LasR inhibition (9A) with % LasR activation (9B) for compound 33. Compound 33 exhibits about 10% LasR activation at high concentrations.

Figure 10A:
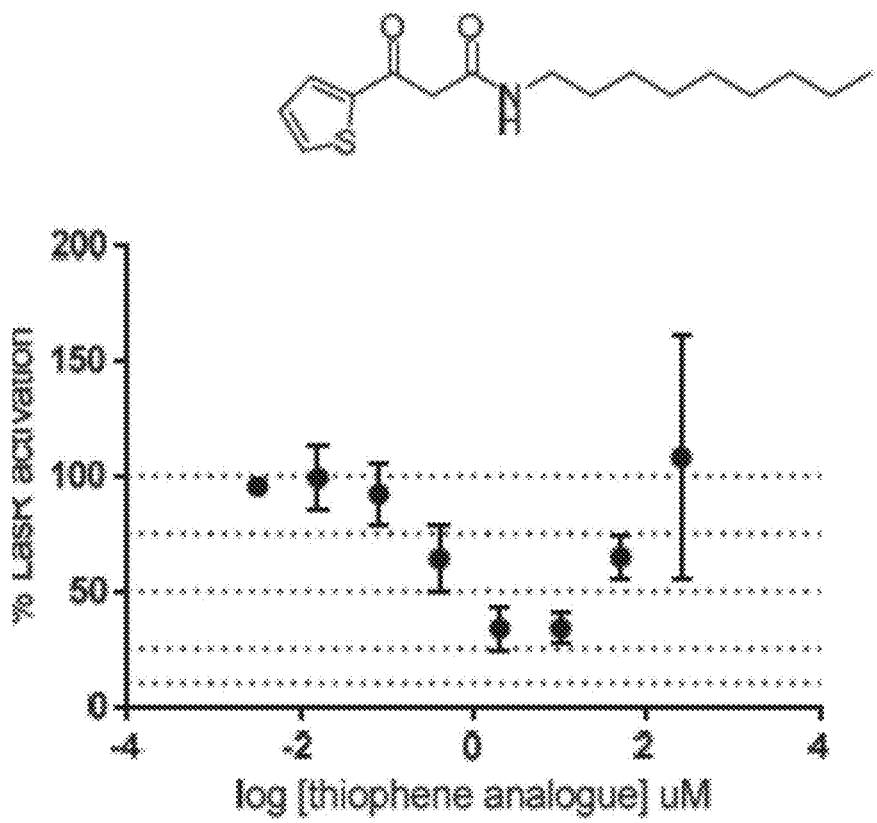
FIGS. 10A and 10B are graphs comparing the inhibition (antagonism) FIG. 10A, or activation (agonism) FIG. 10B of LasR by the indicated compound.
Figure 10B:
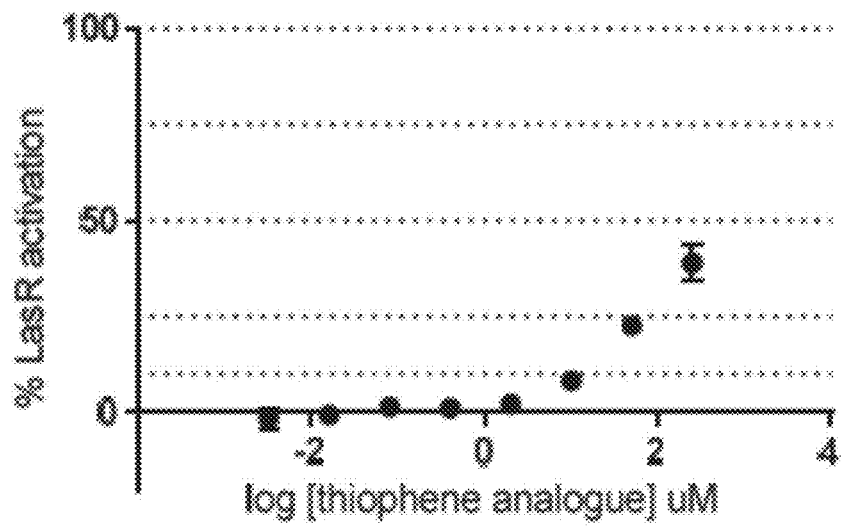

FIGS. 10A and 10B compare % LasR inhibition (10A) with % LasR activation (10B) for compound 32 (thiophene analog of compound 33). Compound 32 exhibits over 25% LasR activation at high concentrations.

Example 3: Inhibition of Production of Elastase

Figure 11:
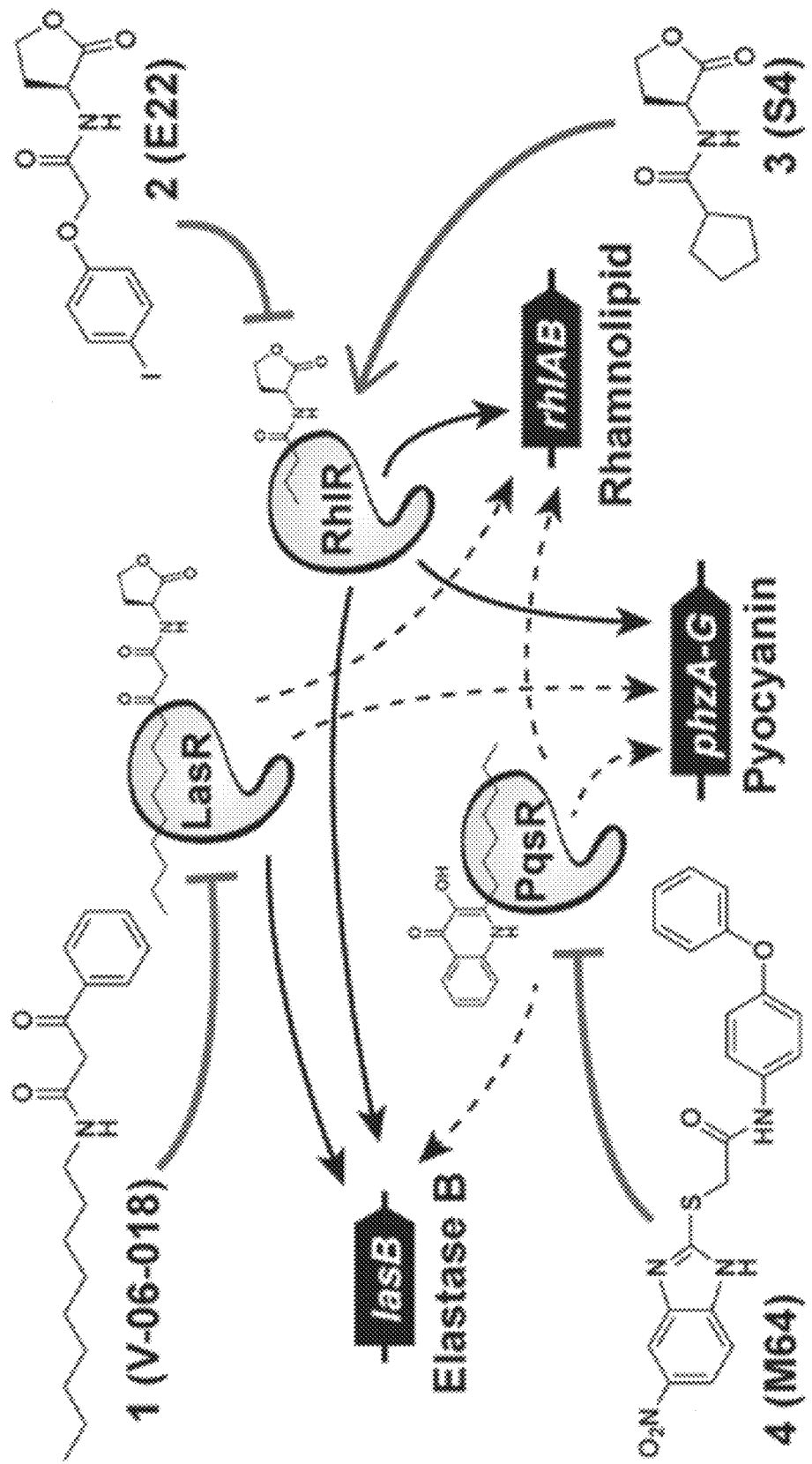
FIG. 11 is an illustration of the regulation of pyocyanin, rhamnolipid and elastase B production in *Pseudomonas aeruginosa*. The illustration is taken from Welsh et al., 2016.

As shown in FIG. 11, in *P. aeruginosa*, pyocyanin, rhamnolipid and elastase B production is regulated by LasR, EhlR and PqsR. In FIG. 11, black closed solid arrowheads with solid lines indicate direct, positive regulation, while black closed solid arrowheads with dashed lines indicate positive regulation by indirect or unknown mechanisms. The figure illustrates certain small-molecule QS probes including the LasR antagonist V-06-018 (1) (Muh et al., 2006; Moore et al., 2015), the RhlR antagonist 2 (Welsh et al., 2015; Eibergen et al., 2015), the RhlR agonist 3 (S4) (Welsh et al., 2015), and the PqsR antagonist 4 (M64) (Starkey et al., 2014). For each compound, gray lines with flat ends indicate receptor antagonism, while the black open arrowhead with solid line indicates receptor agonism.

Figure 12A:
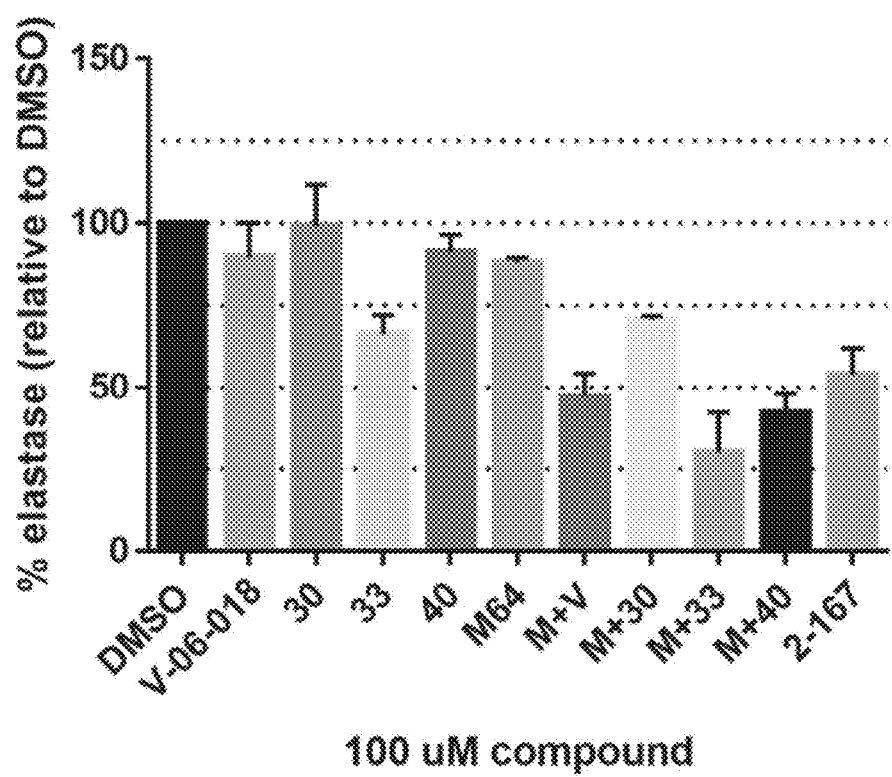
FIGS. 12A and 12B compare inhibition of production of virulence factor elastase by a strain of *P. aeruginosa*.

FIG. 12A is a graph comparing inhibition of elastase (as % relative to DMSO) for certain compounds of the invention. The amount of indicated compound added was 100 µM. M64 alone or in combination was added in the amount of 20 µM. The assay is conducted as described in Welsh et al. (2016) for compounds shown as well as certain compounds in combination with compound M-64 (Starkey, M. et al. (2014)):

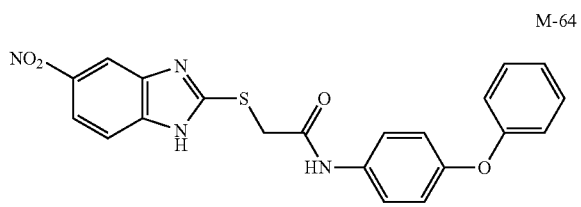 [SMILES: O=C(CSc1nc2cc([N+](=O)[O-])ccc2[nH]1)Nc1ccc(Oc2ccccc2)cc1]

M-64

The amount of elastase B in *P. aeruginosa* culture supernatants was measured following a reported protocol (Welsh et al., 2017 and Geske et al., 2007b) with modifications. A 10 mL overnight culture of *P. aeruginosa* PAO1 was grown for 16 hr. An inoculating culture was prepared by diluting the overnight culture 1:100 into freshly prepared assay medium, and 2 mL aliquots of this subculture were added to each test tube (0.5% DMSO, final). The cultures were grown for 17 hr, and the final cell density measured by reading OD600. Aliquots of the final culture supernatant (50 µL) were added to the wells of a clear, plastic 96-well plate. To each well, 150 µL of 0.5% (w/v) elastin-Congo red conjugate (Elastin Products) in Tris buffer (10 mM Tris-HCl, 1 mM $CaCl_2$) [pH 7.2]) was added. The plate was sealed with a polypropylene storage mat (Costar 3080) and incubated in a 37"C shaking incubator (200 rpm) attached to a Labquake rotator for 24 hr (in LB medium).

To quantify elastase B activity, the undigested elastin was pelleted by centrifugation of the assay plate at 1,500 3 g for 10 min, after which 100 mL of the supernatant was transferred to a new, clear 96-well plate, and the absorbance at 490 nm measured. Media background absorbance (measured from a "no bacteria" control) was subtracted, the resulting values growth normalized by dividing by the final OD600, and the data plotted relative to a DMSO-treated positive control.

Figure 12B:
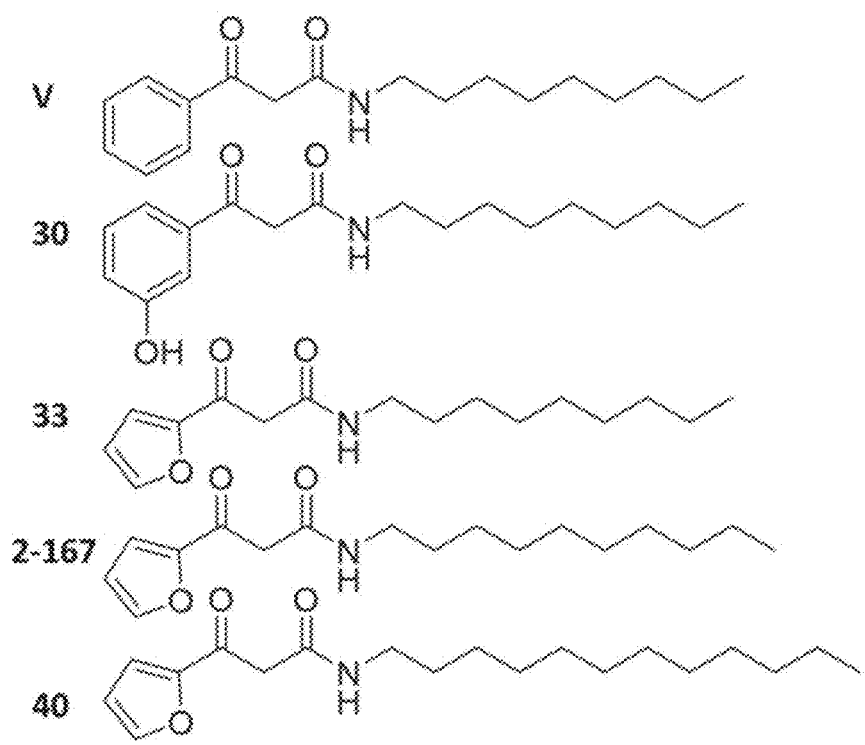

The structures of the compounds assessed in FIG. 12A are shown in FIG. 12B. Compound 33 inhibits the production of virulence factor elastase. Compounds 30, 33, and 40 inhibit elastase synergistically with PqsR inhibitor M-64. V-06-018 (also V) has previously been shown to inhibit elastase production. The results in FIG. 11 show little or no inhibition by V-06-018. These results may be due to old/degraded stocks. This particular result is being retested.

Starkey et al. (2014) is incorporated by reference herein for descriptions of inhibition of quorum sensing systems in *Pseudomonas* strains by compound 64 as well as by other related compounds. Additional inhibitory compounds of this reference, whose structures are given therein, can be employed in combinations with the compounds of this invention for inhibition of virulence factors in *Pseudomonas* strains and particularly in *P. aeruginosa* strains.

REFERENCES

Muh, U.; Hare, B. J.; Duerkop, B. A.; Schuster, M.; Hanzelka, B. L.; Heim, R.; Olson, E. R.; Greenberg, E. P. Proc. Nat. Acad. Sci. U.S.A. 2006, 103, 16948-16952.

Amara, N.; Mashiach, R.; Amar, D.; Krief, P.; Spieser, S. A. H.; Bottomley, M. J.; Aharoni, A.; Meijler, M. M. J. Am. Chem. Soc. 2009, 131, 10610-10619.

Hodgkinson, J. T.; Galloway, W. R. J. D.; Wright, M.; Mati, I. K.; Nicholson, R. L.; Welch, M.; Spring, D. R. Org. Biomol. Chem. 2012, 10, 6032-6044.

Geske, G. D.; Wezeman, R. J.; Siegel, A. P.; Blackwell, H. E. J. Am. Chem. Soc. 2005, 127, 12762-12763.

Geske, Jennifer C. O'Neill, and Helen E. Blackwell (2007a) N-Phenylacetanoyl-L-Homoserine Lactones Can Strongly Antagonize or Superagonize Quorum Sensing in *Vibrio fischeri*," ACS Chem. Biol. 2(5), 315-320.

Geske, G. D.; O'Neill, J. C.; Miller, D. M.; Mattmann, M. E.; Blackwell, H. E. J. Am. Chem. Soc. 2007b, 129, 13613-13625.

Geske, G. D.; Mattmann, M. E.; Blackwell, H. E. Bioorg. Med. Chem. Lett. 2008a, 18, 5978-5981.

Geske, G. D.; O'Neill, J. C.; Miller, D. M.; Wezeman, R. J.; Mattmann, M. E.; Lin, Q.; Blackwell, H. E. ChemBioChem 2008b, 9, 389-400.

Mattmann, M. E.; Shipway, P. M.; Heth, N. J.; Blackwell, H. E. ChemBioChem 2011, 12, 942-949.

Eibergen, N. A., et al. (2015) "Potent and Selective Modulation of the RhlR Quorum Sensing Receptor by Using Non-native Ligands: An Emerging Target for Virulence Control in *Pseudomonas aeruginosa*," ChemBioChem, 16, 2348-2356.

Moore, J. D.; Rossi, F. M.; Welsh, M. A.; Nyffeler, K. E.; Blackwell, H. E. J Am Chem Soc 2015, 137, 14626.

Moore, J. D.; Gerdt, J. P.; Eibergen, N. R.; Blackwell, H. E., ChemBioChem 2014, 15, 435-442.

O'Reilly, M. C.; Blackwell, H. E. ACS Infectious Diseases 2016, 2, 32.

Welsh, M. A. et al. (2016) "Chemical Genetics Reveals Environment-Specific Roles for Quorum Sensing Circuits in *Pseudomonas aeruginosa*," *Cell Chem Biol* 2016, 23 (3), 361-9.

M. A. Welsh, N. R. Eibergen, J. D. Moore, and H. E. Blackwell. "Small molecule disruption of quorum sensing cross-regulation in *Pseudomonas aeruginosa* causes major and unexpected alterations to virulence phenotypes." J. Am. Chem. Soc. 2015, 137, 1510-1519.

Starkey, M.; Lepine, F.; Maura, D.; Bandyopadhaya, A.; Lesic, B.; He, J.; Kitao, T.; Righi, V.; Milot, S.; Tzika, A.; Rahme, L., "Identification of anti-virulence compounds that disrupt quorum-sensing regulated acute and persistent pathogenicity." PLoS Pathog 2014, 10 (8), e1004321

The invention claimed is:

1. A compound of formula:

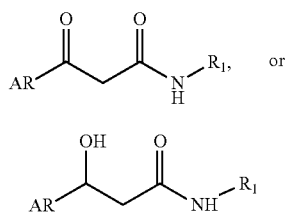

where:
AR is an optionally substituted phenyl, an optionally substituted cycloalkyl or cycloalkenyl or an optionally substituted heterocyclic group; and
$R_1$ is an optionally substituted straight-chain or branched alkyl group or alkenyl group having 3-18 carbon atoms or is an optionally substituted straight-chain or branched alkyl group having 2-18 carbon atoms wherein one or more non-adjacent —$CH_2$— moieties are replaced with —O— or —S—; or
$R_1$ is a C1-C4 alkyl group substituted with an optionally substituted phenyl, cyclohexyl or cyclohexenyl group; with the exception that for compounds of formula I, AR is not an unsubstituted phenyl and wherein optional substitution is substitution with one or more non-hydrogen substituents selected from halogen, hydroxyl, alkoxy, or $NH_2$.

2. The compound of claim 1, wherein $R_1$ is a straight-chain or branched alkyl group having 9-12 carbon atoms.

3. The compound of claim 1, wherein $R_1$ is a straight-chain alkyl group having 9-12 carbon atoms.

4. The compound of claim 1, wherein $R_1$ is selected from the group consisting of a straight-chain alkyl group having 9-12 carbon atoms, a straight-chain alkenyl group having 9-12 carbon atoms, an alkoxyalkyl group, and an alkylthioalkyl group.

5. The compound of claim 1, wherein AR is substituted phenyl.

6. The compound of claim 1, wherein AR is a hydroxyl-substituted or a halo-substituted phenyl.

7. The compound of claim 1, wherein AR is selected from the group consisting of substituted phenyl and furyl.

8. The compound of claim 1, wherein AR is fur-2-yl or fur-3-yl.

9. The compound of claim 1, wherein AR is selected from the group consisting of thiophenyl, thiazolyl, pyridyl, cyclohexyl and cyclohexenyl.

10. The compound of claim 1 of formula II.

11. A compound of claim 1 selected from the group consisting of compounds of formulae:

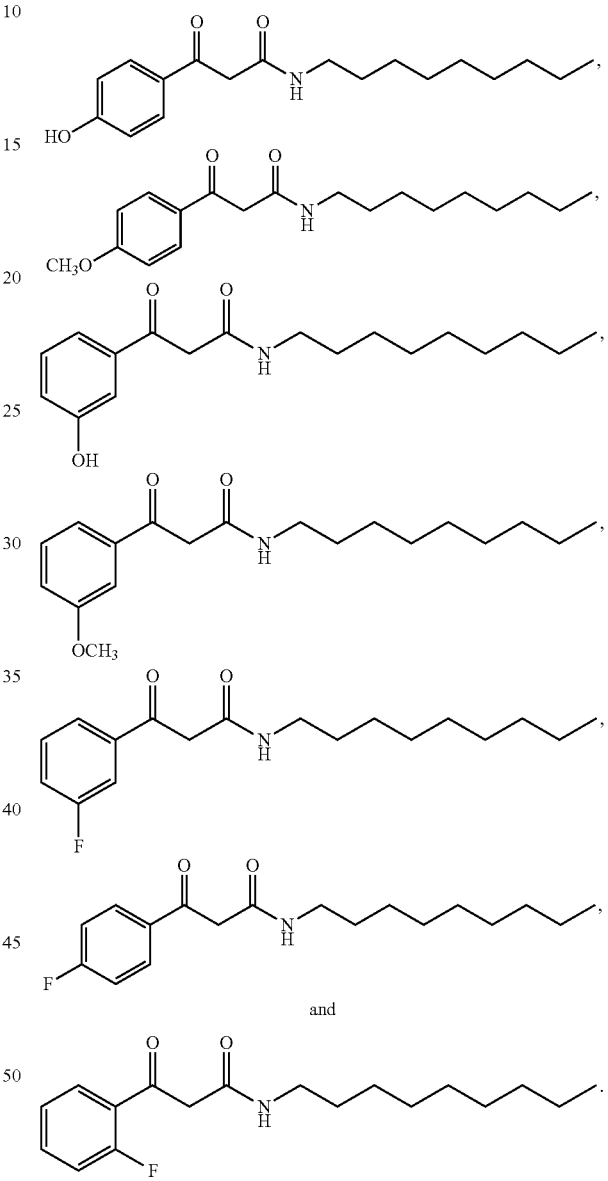

12. A pharmaceutical composition comprising a therapeutically effective amount of one or more compounds of claim 1 in combination with a pharmaceutically acceptable carrier.

13. A method for inhibiting quorum sensing in a Gram-negative bacterium which comprises the step of contacting the Gram-negative bacterium or an environment containing the bacterium with one or more compounds of claim 1.

14. A method for inhibiting biofilm formation by a Gram-negative bacterium which comprises the step of contacting the Gram-negative bacterium, the environment of the bacterium or a biofilm of the bacterium with one or more compounds of claim 1.

15. A method for treating an infection by a Gram-negative bacterium which comprises administering to a subject in need of such treatment a therapeutically effective amount of one or more compounds of claim 1.

16. The compound of claim 1 selected from the group consisting of compounds of formulae:

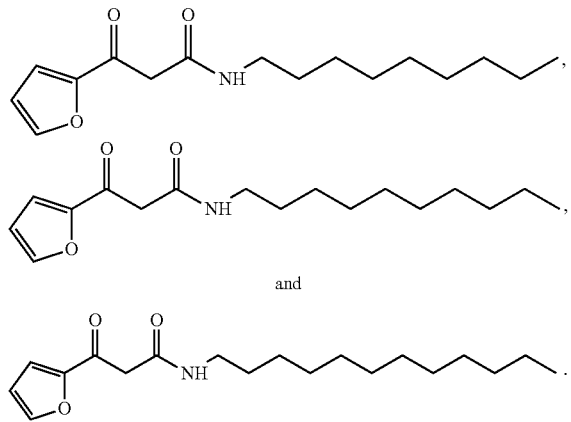

and

17. The compound of claim 1 of formula I.

18. The compound of claim 17, wherein:
AR is a phenyl group substituted with a hydroxyl, halogen or alkoxyl group or is a furyl group; and $R_1$ is a straight-chain alkyl group having 9-12 carbon atoms.

19. The compound of claim 1, wherein:
AR is a phenyl group substituted with a hydroxyl, halogen or alkoxyl group or is a furyl group; and $R_1$ is a straight-chain alkyl group having 9-12 carbon atoms.

20. Then compound of claim 1 having formula:

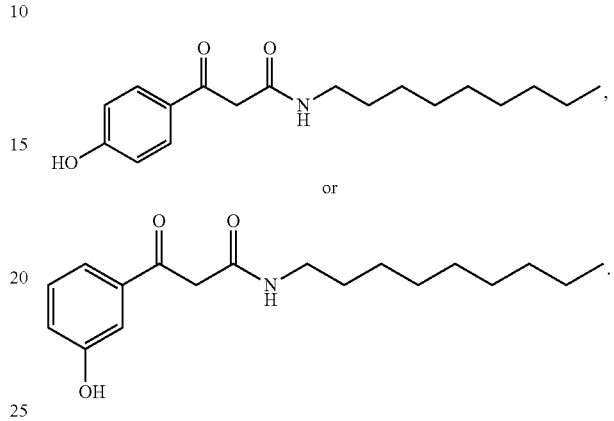

or

* * * * *